(12) United States Patent
Walters

(10) Patent No.: US 8,685,059 B2
(45) Date of Patent: Apr. 1, 2014

(54) SELF-LOCKING CLOSURE DEVICE FOR PERCUTANEOUSLY SEALING PUNCTURES

(75) Inventor: Greg Alan Walters, Exton, PA (US)

(73) Assignee: Essential Medical LLC, Malvern, PA (US)

(*) Notice: Subject to any disclaimer, the term of this patent is extended or adjusted under 35 U.S.C. 154(b) by 247 days.

(21) Appl. No.: 13/025,593

(22) Filed: Feb. 11, 2011

(65) Prior Publication Data
US 2011/0301638 A1    Dec. 8, 2011

Related U.S. Application Data

(60) Provisional application No. 61/352,807, filed on Jun. 8, 2010.

(51) Int. Cl.
*A61B 17/00* (2006.01)
*A61B 17/08* (2006.01)

(52) U.S. Cl.
USPC ................ 606/213; 606/215; 606/232

(58) Field of Classification Search
None
See application file for complete search history.

(56) References Cited

U.S. PATENT DOCUMENTS

| | | | | |
|---|---|---|---|---|
| 3,125,095 A * | 3/1964 | Kaufman et al. | ............ | 606/226 |
| 5,021,059 A | 6/1991 | Kensey et al. | | |
| 5,222,974 A * | 6/1993 | Kensey et al. | ............ | 606/213 |
| 5,282,827 A | 2/1994 | Kensey et al. | | |
| 5,411,520 A * | 5/1995 | Nash et al. | ............ | 606/213 |
| 5,531,759 A * | 7/1996 | Kensey et al. | ............ | 606/213 |
| 5,545,178 A * | 8/1996 | Kensey et al. | ............ | 606/213 |
| 5,662,681 A * | 9/1997 | Nash et al. | ............ | 606/213 |
| 5,700,277 A * | 12/1997 | Nash et al. | ............ | 606/213 |
| 5,702,421 A | 12/1997 | Schneidt | | |
| 7,905,902 B2 * | 3/2011 | Huitema et al. | ............ | 606/220 |
| 8,337,522 B2 * | 12/2012 | Ditter | ............ | 606/213 |
| 8,444,673 B2 * | 5/2013 | Thielen et al. | ............ | 606/232 |
| 2001/0003158 A1 | 6/2001 | Kensey et al. | | |
| 2001/0044639 A1 | 11/2001 | Levinson | | |
| 2006/0058844 A1 * | 3/2006 | White et al. | ............ | 606/232 |
| 2007/0123936 A1 | 5/2007 | Goldin et al. | | |
| 2008/0306509 A1 | 12/2008 | Osborne | | |
| 2009/0099598 A1 | 4/2009 | McDevitt et al. | | |
| 2011/0054456 A1 | 3/2011 | Thompson et al. | | |
| 2011/0301619 A1 * | 12/2011 | Walters | ............ | 606/144 |

OTHER PUBLICATIONS

PCT/US2012/061855, "International Search Report & Written Opinion" mailed Jan. 22, 2013.
PCT/US2011/039645, "Written Opinion and International Preliminary Report on Patentability", mailed Oct. 4, 2011.
PCT/US2011/039645, "International Search Report", mailed Oct. 4, 2011.

* cited by examiner

*Primary Examiner* — Melanie Tyson
*Assistant Examiner* — Todd J Scherbel
(74) *Attorney, Agent, or Firm* — Kilpatrick, Townsend & Stockton, LLP.

(57) ABSTRACT

A closure device for sealing a percutaneous puncture in a wall of a body passageway of a living being. In an exemplary embodiment, the closure device includes an anchor configured to be brought into engagement with an interior of the body passageway, a plug including a proximal portion and a distal portion, a filament coupled to the anchor and the plug. The filament may include a first extending section. The closure device further includes a lock attached to the first extending section, wherein the collar is positioned between the lock and the anchor, wherein the lock frictionally engages the first extending section of the filament so that the lock is movable along the filament only in response to application of a force on the lock that overcomes the frictional engagement.

17 Claims, 74 Drawing Sheets

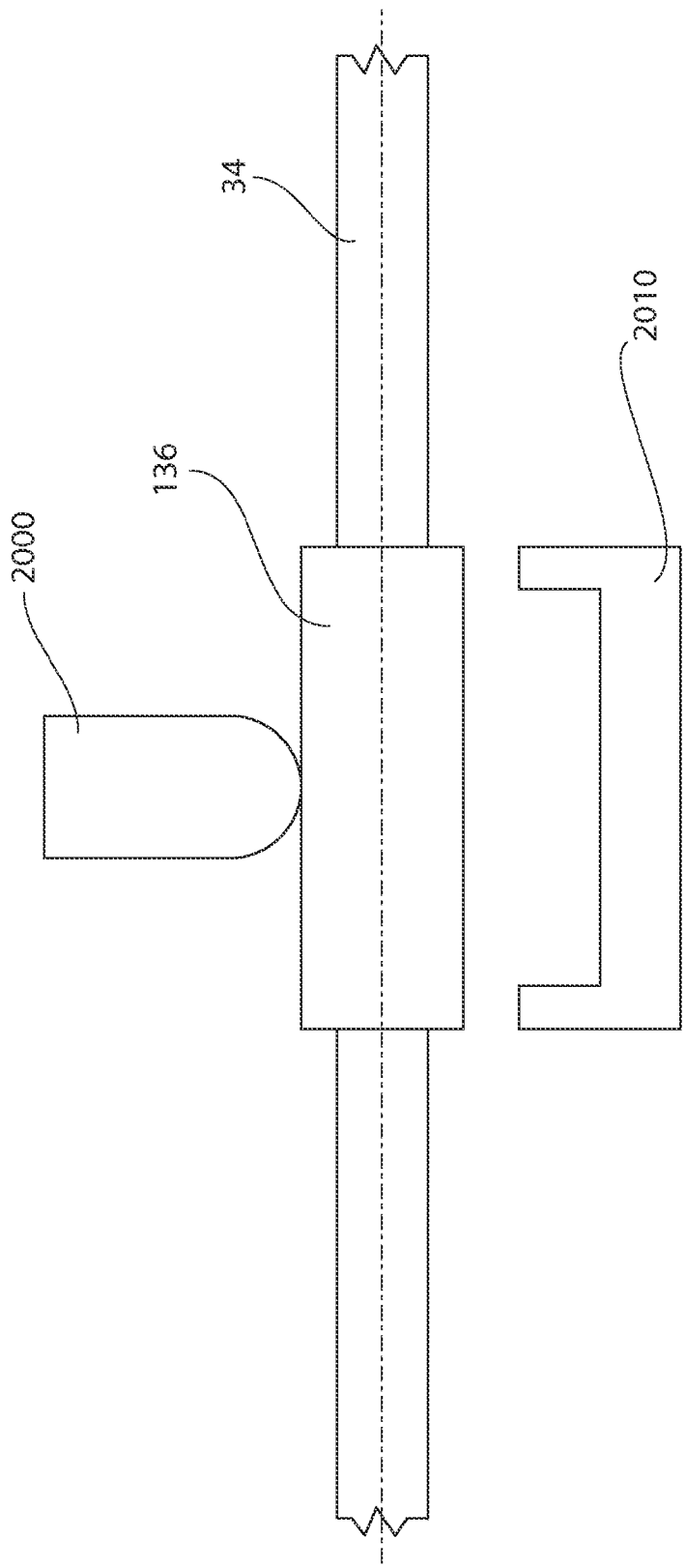

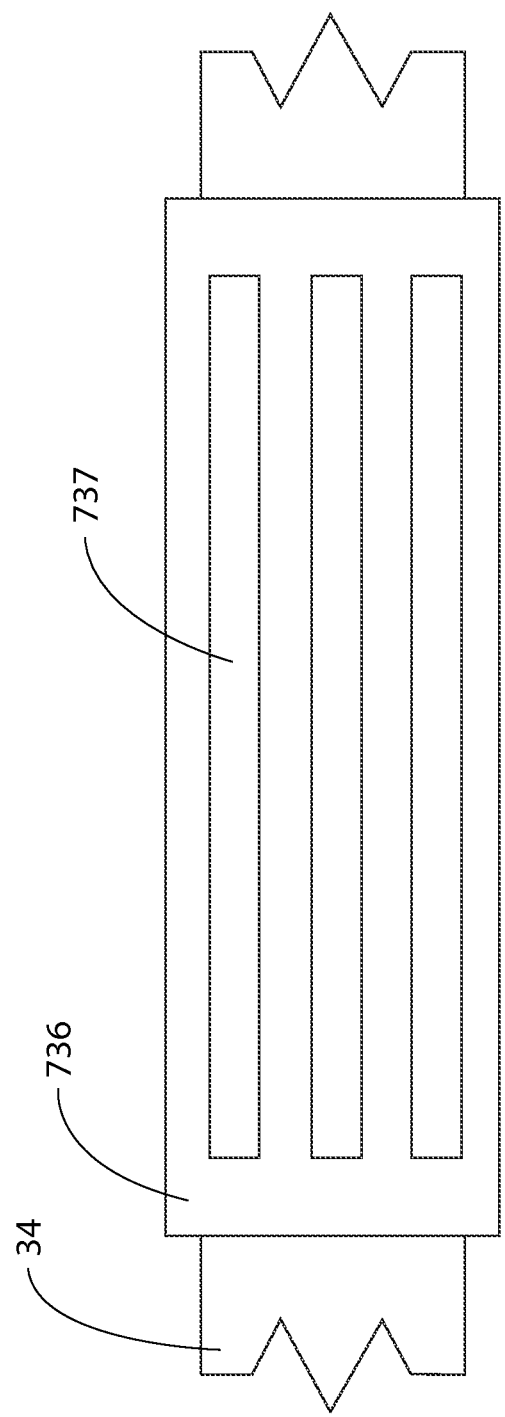

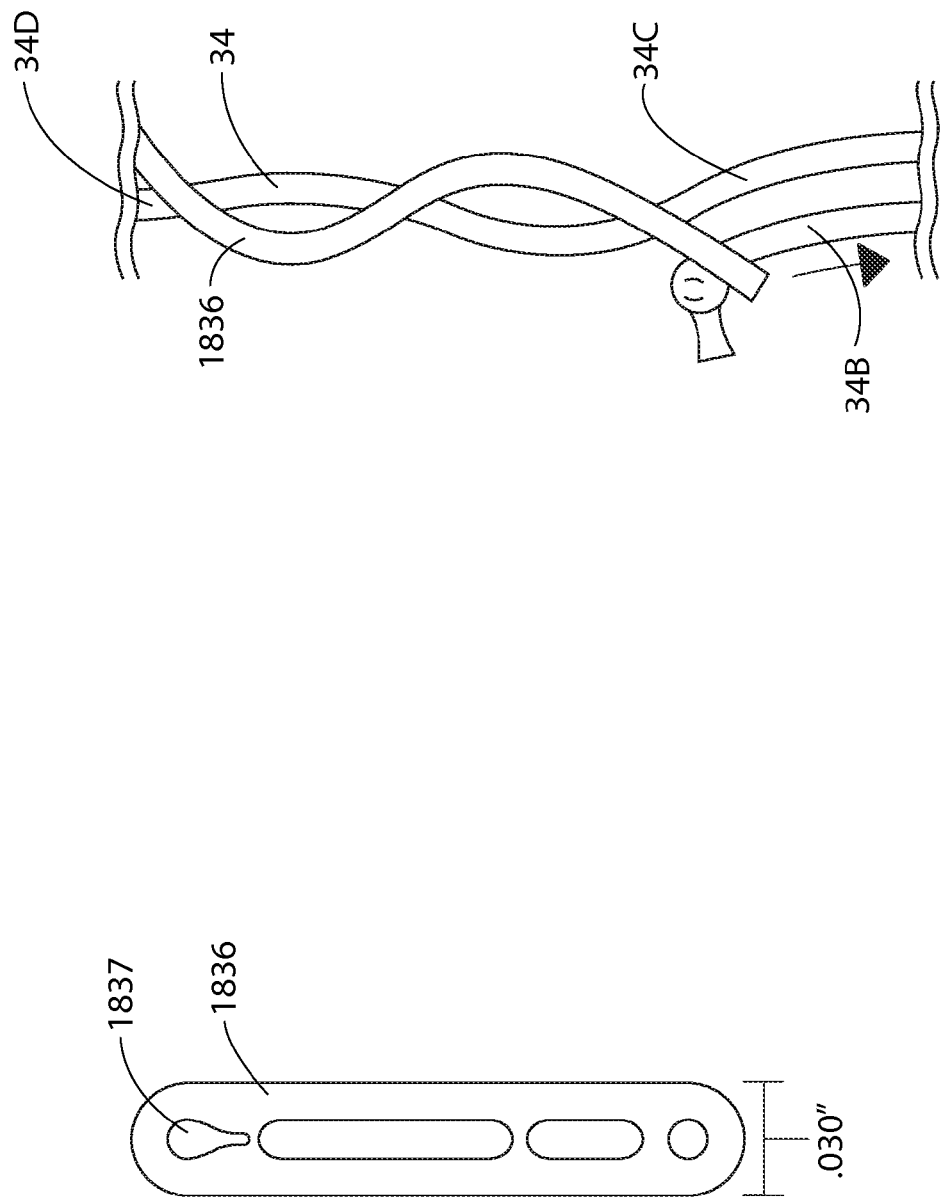

SELF-LOCKING CLOSURE DEVICE FOR PERCUTANEOUSLY SEALING PUNCTURES

CROSS-REFERENCE TO RELATED APPLICATION(S)

The present application claims priority to U.S. Provisional Patent Application No. 61/352,807, filed on Jun. 8, 2010, entitled "Closure Device," the contents of that application being incorporated herein by reference in its entirety.

BACKGROUND

1. Field of the Invention

The present invention relates generally to closing percutaneous punctures, and more particularly to a self-locking closure device for sealing percutaneous punctures.

2. Related Art

U.S. Pat. No. 5,282,827 (hereinafter, the '827 patent), entitled Hemostatic Puncture Closure System and Method of Use, teaches systems for sealing a percutaneous incision or puncture in a blood vessel. The systems of the '827 patent comprise a closure device, an introducer, and a deployment instrument including a carrier for the closure device. The closure device has three basic components, namely, a sealing member, an intra-arterial anchor, and a positioning member. The sealing member is in the form of an elongated rod-like plug, e.g., a compressed hemostatic, resorbable collagen sponge or foam. This plug member is arranged for sealing the puncture. The anchor is an elongated, stiff, low-profile member which is arranged to be seated inside the artery against the artery wall contiguous with the puncture. The anchor is molded of non-hemostatic resorbable polymer similar to resorbable suture. The positioning member comprises a filament, e.g., a resorbable suture. The filament connects the anchor and the collagen plug (sealing member) in a pulley-like arrangement, and includes a portion extending outside the patient's body. The outwardly located filament portion is arranged to be pulled, i.e., tension applied thereto, after the anchor is located within the interior of the artery and in engagement with the inner wall of the artery contiguous with the incision or puncture. The pulling on the filament causes its pulley arrangement to move the plug in the puncture tract toward the anchor. A tamper forming a portion of the deployment instrument is slid down the filament while the filament is maintained in tension to gently tamp the plug in the puncture tract to cause the plug to deform so that its diameter increases. Tension is maintained on the filament by use of an externally located spring during the tamping procedure. The expansion of the plug within the tract is enhanced by the fact that it is formed of a compressed collagen so that it expands in the presence of blood within the puncture tract. The expansion of the plug within the puncture tract serves to hold it in place. Moreover, the closure device quickly becomes locked in place through the clotting of the hemostatic collagen plug within the puncture tract. The spring serves to hold the plug in its deformed state until such time that the plug is locked in place by the hemostatic clotting action. Once this has occurred, so that the plug is effectively locked within the puncture tract, the externally located spring can be removed. This typically occurs after approximately 30 minutes. After the spring is removed, the filament is severed at the top of the tamper. The tamper is then removed and the remaining portion of the filament is cut subcutaneously prior to the discharge of the patient. The portion of the filament connecting the anchor to the plug remains in tension, thereby holding the closure device permanently in place until it is eventually absorbed by the patient's body.

U.S. Pat. No. 5,662,681 (hereinafter, the '681 patent), entitled Self-locking Closure for Sealing Percutaneous Punctures, also teaches systems for sealing a percutaneous incision or puncture in a blood vessel.

SUMMARY

In one aspect of the present invention, there is a closure device for sealing a percutaneous puncture in a wall of a body passageway, the closure device comprising an anchor configured to engage an interior surface of the body passageway, a plug, a contiguous elongate filament, coupled to the anchor and the plug, including first and second sections extending from the anchor with the first section extending through a collar connected to the second section such that a loop is formed by the first and second sections and the collar, wherein the loop extends through an orifice in the plug, and a lock frictionally engaged to a portion of the first section extending beyond said loop. The lock is movable along the filament only in response to application of a force on the lock that overcomes the frictional engagement, whereby as the lock is moved along the first section towards the anchor, the loop shrinks causing the plug to move toward the anchor, wherein the lock is configured to prevent the loop from expanding after said shrinkage of the loop.

The closure device further includes a lock, wherein the lock is attached to the first extending section, wherein the collar is positioned between the lock and the anchor, wherein the lock frictionally engages the first extending section of the filament so that the lock is movable along the filament only as a result of the application of a force onto the lock that overcomes the frictional engagement. The closure device is further configured to move the proximal portion of the plug toward the anchor as a result of a shrinkage of the loop. The lock is configured to prevent the loop from expanding after shrinkage of the loop once the lock is moved along the first extending section proximate the collar.

According to another aspect of the present invention, there is a method of making a closure device for sealing a percutaneous puncture in a wall of a body passageway of a living being. The method comprises coupling a filament to an anchor configured to be brought into engagement with an interior of the body passageway and to a plug such that the filament forms a loop extending through a portion of the anchor and a portion of the plug, slidably attaching an embryonic lock to the filament such that movement of the filament relative to the embryonic lock in a first direction reduces an interior diameter of the loop, thereby drawing the anchor closer to at least a portion of the plug, and crimping the embryonic lock to form a lock such that the lock frictionally engages the filament so that the lock is slidable along the filament only in response to application of a force on the lock that overcomes the frictional engagement.

According to another aspect of the present invention, there is a method of sealing a percutaneous puncture in a body passageway of a living being. The method comprises inserting an anchor coupled to a filament loop in the body passageway through the percutaneous puncture, bringing the anchor into engagement with an interior of the body passageway, applying a tension force to a portion of the filament so that a force is applied to the loop tending to decrease the circumference of the loop, wherein a lock is frictionally slidably engaged with a portion of the filament extending from the circumference of the loop, applying a tamping force to the lock in a direction towards the loop and in a direction away from the direction of the applied tension to the portion of the filament, wherein the tamping force is sufficient to overcome the frictional engagement forces so that the lock slides along the filament in a direction towards the anchor. The lock is configured to resist movement along the filament in a direction opposite the direction of the tamping force, thereby preventing the circumference of the loop from expanding relative to the circumference of the loop after application of the tamping force and the tension force.

BRIEF DESCRIPTION OF THE DRAWINGS

Embodiments of the present invention are described herein with reference to the attached drawing sheets in which:

FIGS. 30A-30B depict another exemplary embodiment in which the lock is twisted whereby the requisite friction force between the lock and the filament is controlled;

FIGS. 49-52 depict additional exemplary embodiments of a lock;

FIGS. 53-55 depict use of the lock of FIG. 52;

DETAILED DESCRIPTION

Figure 1A:
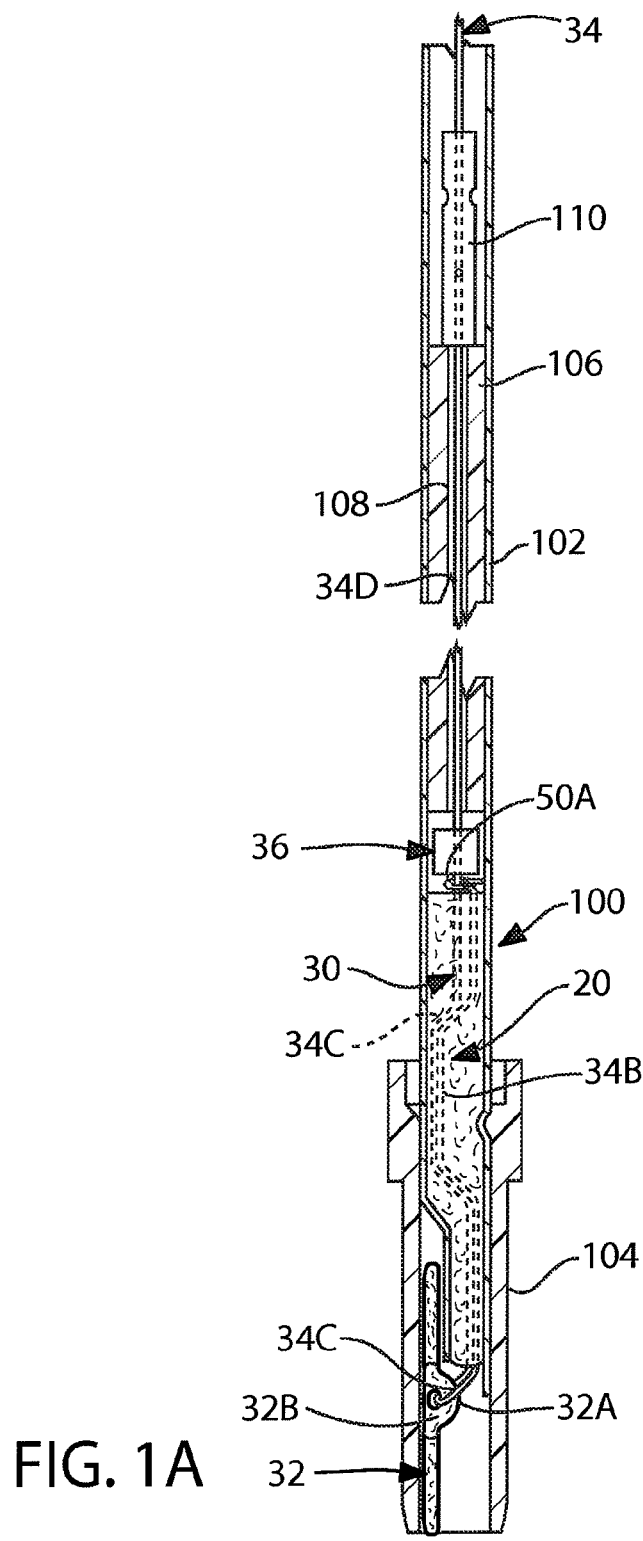
FIG. 1A is a longitudinal sectional view of the distal end of an introducing instrument holding one embodiment of the closure device of this invention prior to its deployment to plug a percutaneous incision or puncture in a body passageway, such as a blood vessel, duct, etc., of a living being.

Referring now in greater detail to the various figures of the drawings wherein like reference characters refer to like parts, here is shown at FIG. 1A a closure device 20 constructed in accordance with one embodiment and disposed within the distal end of a deployment instrument 100.

The closure device 20 is arranged for sealing a percutaneous puncture in any body passageway, such as, for example, a blood vessel, duct, etc., in the body of a living being after having been introduced therein by the deployment instrument 100. For the remainder of this application, the closure device 20 will be described with reference to sealing a percutaneous puncture in a blood vessel, e.g., the femoral artery.

Figure 1B:
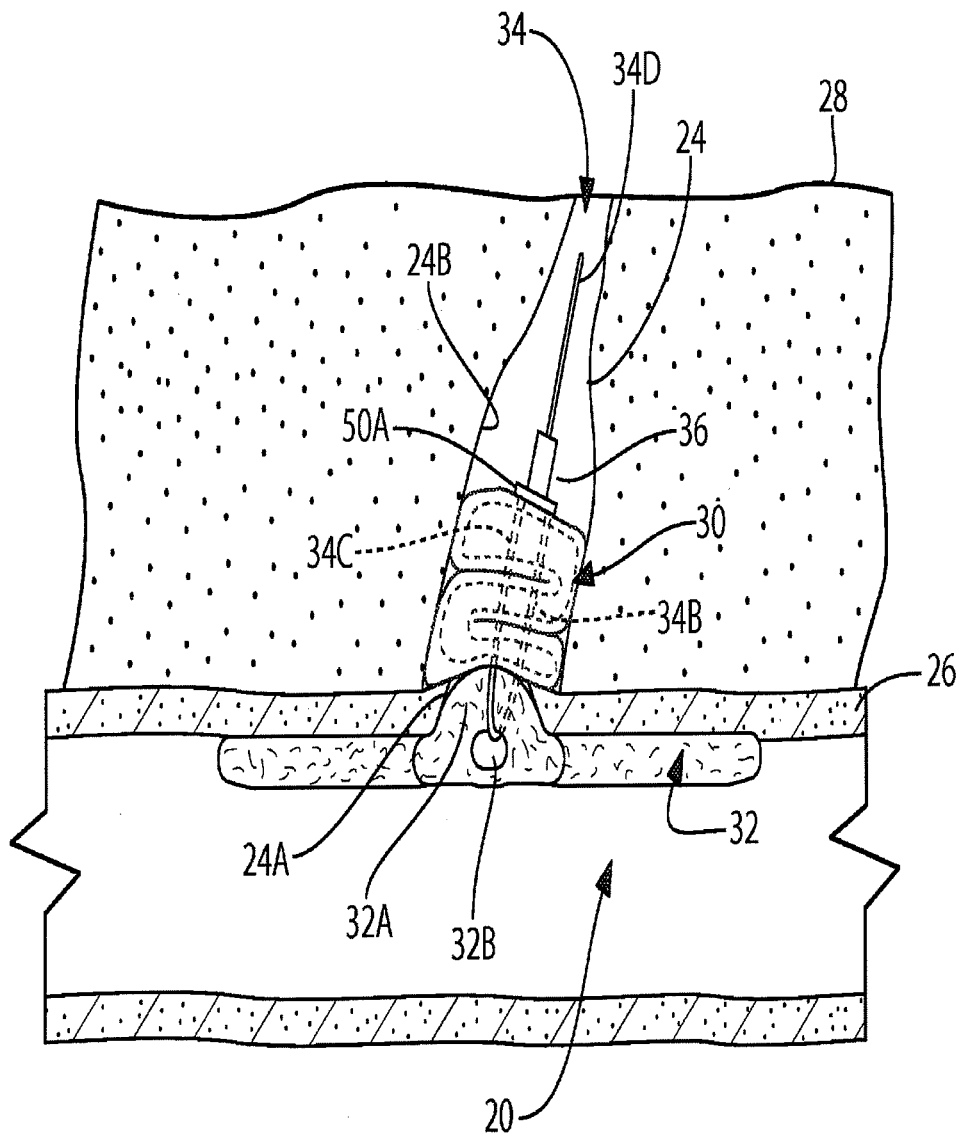
FIG. 1B is a partial sectional view showing a closure device according to an embodiment in its fully deployed state sealing a percutaneous puncture or incision in a body passageway of a living being.

In FIG. 1B the closure device 20 is shown in its fully deployed state sealing a percutaneous puncture 24 in the femoral artery 26. As can be seen therein the percutaneous puncture 24 includes an opening or a hole 24A in the artery 26 wall and a tract 24B leading up to the opening 24A. By tract it is meant the passageway in the tissue located between the artery 26 and the skin 28 of the being, and which is formed when the artery is punctured percutaneously.

Figure 2:
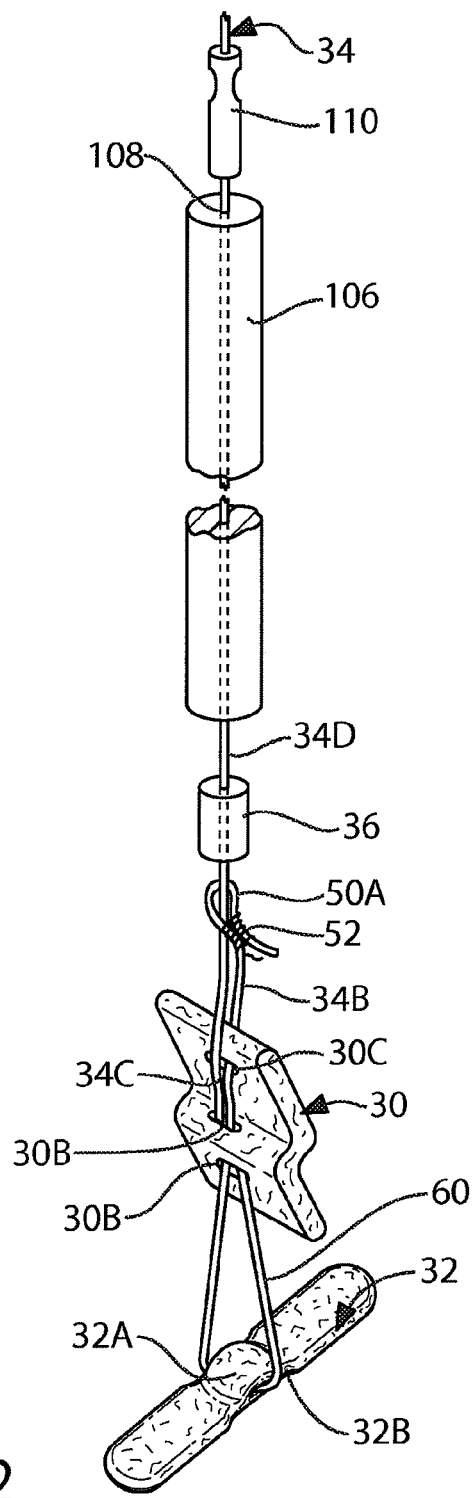
FIG. 2 is an exploded isometric view of a closure device according to an embodiment, shown after assembly of the components but prior to deployment in a living being.

To expedite the understanding of the construction and operation of this invention, the closure device 20 will first be described. Referring to FIG. 2, the closure device 20 has four basic components, namely, plug 30 (often referred to in the art as a sealing member or collagen pad), an intra-arterial anchor 32, a positioning filament 34, and a lock 36. In an embodiment, the anchor 32 and the filament 34 are each constructed in accordance with the teachings of the aforementioned '827 patent and/or the aforementioned '681 patent, the teachings of the '827 and '681 patents relating to the construction and features of the anchor and filament being incorporated for use in an embodiment herein.

In an embodiment, the filament 34 (also referred to as suture) is a braided multifilament size 2-0 PLLA suture. The filament 34 may be made from any synthetic absorbable plastic material that degrades as needed.

Further, in an embodiment, the anchor may be constructed of a 50/50 polylactic-cogycolic acid or other synthetic absorbable polymer that degrades in the presence of water into naturally occurring metabolites (e.g., water and $CO_2$). The anchor may be shaped like a small plank having dimensions of about 2 mm×10 mm×1 mm.

In an embodiment, the anchor 32 is a monolithic structure formed by a bio-absorbable polymer. In an embodiment, the shape of the plug 30 is constructed accordance with the teachings of the '827 patent, except for apertures (to be described later) in the plug and the manner that the filament 34 is coupled to plug 30. In an embodiment, the plug 30 is a collagen pad made of a fibrous collagen mix of insoluble and soluble collagen that is cross linked for strength. In an embodiment, the collagen may be obtained from the connective tissue of animals. The collagen may be purified from the subdermal layer of cowhide. In an embodiment, prior to use in the closure device 30, the plug 30 has dimensions of about 10 mm×30 mm×2 mm.

As with the closure devices of the '827 patent, the closure device 20 is arranged to be deployed into the percutaneous puncture 24 via the same basic introducing instrument as described in that patent. Referring to FIG. 1A, that instrument is designated by the reference number 100, and only the distal portion of it is shown herein in the interest of drawing simplicity. Thus, the deployment instrument 100 basically comprises a tubular carrier 102 formed of a somewhat flexible material to enable the carrier tube to freely pass through any conventional introducer sheath (not shown) into an operative position within the patient's artery. The distal end of the carrier tube includes a stiff sleeve or tube 104 to enable the carrier tube to be inserted through a hemostasis valve (not shown) of the introducer sheath, through the sheath, and out the distal end thereof into the artery. The proximal end of the deployment instrument 100 includes a filament tensioning assembly (not shown). An elongated tamper 106 is located within the carrier tube. The tamper member 106 is constructed in accordance with the teachings of the '827 patent and includes a central passageway 108 extending longitudinally therethrough. The teachings of the '827 patent and the '681 patent relating to the tamper member and its use are incorporated by reference for inclusion in an embodiment herein.

The closure device 20 is arranged to be disposed within the distal end of the tubular carrier 102 such that it is ready for deployment into the puncture 24 in a similar manner to that described in the '827 patent. In particular, the anchor 32 is disposed longitudinally within the tube 104 laterally of the central longitudinal axis of the carrier tube 102. The plug 30 is located within the carrier tube just behind (proximally) of the anchor 32 and on the opposite side of the central longitudinal axis. The lock 36 is located proximally of the plug 30, while the tamper is located proximally of the lock in the carrier tube.

In an embodiment, the anchor 32 is similar to the anchor of the '827 patent. Thus, it basically comprises a thin, narrow, strip or bar of material which is sufficiently stiff such that once it is in position within the artery, it is resistant to deformation to preclude it from bending to pass back through the puncture through which it was first introduced. In an embodiment, the surface of the anchor 32 abutting the artery wall 26 has a slight curve across the transverse axis (i.e., the axis normal to the view of FIG. 1B). In an embodiment, this curve better conforms the surface of the anchor to the curved interior surface of the artery wall 26. As can be seen in FIG. 1B, the dome-like projection 32A is arranged to extend into the opening 24A in the artery wall 26 when the anchor 32 is properly deployed within that artery, i.e., when the top surface of the anchor is in engagement with the interior of the artery contiguous with the opening 24A. The top of the projection 32A as depicted in the FIGs. is slightly flat, but in an alternate embodiment, the top is rounded. In an embodiment, the projection 32A may form a hemisphere extending from the surface of the anchor 32 that abuts the artery wall 26.

A passageway 32B of generally oval or trapezoidal cross section, but with slightly rounded corners, extends transversely across the anchor 32 below the projection 32A and close to the bottom surface of the anchor. A portion of the filament 34 is arranged to be threaded through this passageway to couple the anchor 32 and loop 50A (described in greater detail below) together in a pulley-like arrangement with at least a portion of the plug 30 interposed between the loop 50A and the anchor.

The pulley-like arrangement of the filament effect the movement and deformation of the plug 30 within the tract 24B once the anchor 32 is in its desired position in the artery (i.e., against the inner surface of the artery wall). This action occurs by applying tension to the filament, as will be described later.

The plug 30 basically comprises a strip of a compressible, resorbable, collagen foam, which is arranged to be straightened and compressed transversely to its longitudinal axis when it is loaded in the carrier tube 102 of the deployment instrument 100. Prior to loading into the deployment instrument, the closure device 20 looks somewhat like that shown in FIG. 2. Thus, as can be seen, the plug 30 includes three apertures, 30A, 30B, and 30C through which portions of the filament 34 extend. When the plug 30 is compressed and linearized for location within the distal end of the carrier tube of the deployment instrument, the apertures 30A-30C are oriented to extend substantially transversely to the longitudinal axis of the plug and parallel to one another. As will be discussed in greater detail below, other configurations of the plug 30 may be utilized, with fewer or additional apertures.

The aperture 30C is located closest, out of the three apertures, to the proximal end of the plug. The aperture 30A is located closest, out of the three apertures, to the distal end of the plug. The aperture 30B is located approximately midway between the apertures 30A and 30B. The apertures 30A-30C variously serve as passageways through which the filament sections 34B and 34C pass to couple the anchor 32 to the lock 36, with the plug and the loop 50A interposed therebetween, as will be described in greater detail below.

Figure 10:
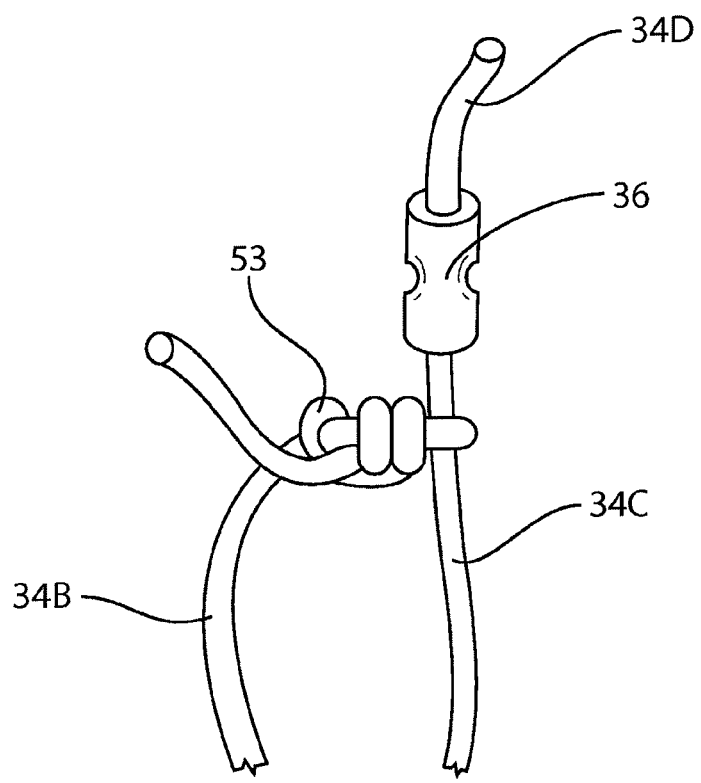
FIG. 10 depicts a loop according to an alternate embodiment.

The filament 34 is identical in construction to that of the aforementioned '827 patent, except for the path through which it extends. In particular, and as will be described in detail later, the filament is an elongated flexible resorbable member, e.g., a suture, of a single strand or multiple strands, and which is defined by a plurality of sequentially located portions or sections. As can be seen in FIG. 2, starting from one end of filament 34, the filament 34 is formed into a loop 50A located between lock 36 and plug 30. The loop 50A is configured and dimensioned to easily move along filament section 34C, which is the portion of filament 34 extending through loop 50A. Loop 50A is configured so that it may easily move along filament section 34C. Thus, loop 50A may be loosely wrapped around filament section 34C. Loop 50A is configured so as to not further tighten about filament section 34C, after it is initially wrapped around section 34C, especially during insertion of the closure device 20. Loop 50A may be formed by looping sections of the filament 34 as shown, and securing those sections by using a winding 52, as depicted in FIG. 2. In other embodiments, the loop 50A may be formed by the use of a knot 53 formed by filament 34, as may be seen in FIG. 10, and also may secure the proximal end of the collagen plug. Filament section 34B of the filament 34 extends from loop 50A to the anchor 32. Between the loop 50A and the anchor 32, filament section 34B passes through apertures 30A, 30B and 30C in plug 30, in a serpentine-like manner. Filament section 34B extends through passageway 32B in anchor 32 to join filament section 34C. Filament section 34C of filament 34 extends from the passageway 32B in the anchor 32 to the plug 30, where it passes through apertures 30A and 30B in the plug 30, and bypasses aperture 30C. In an embodiment, filament section 34C may bypass two or more apertures. Section 34C extends through loop 50A and through lock 36 to join filament section 34D. Filament section 34D extends from the lock 36 through the passageway 108 in the tamper 106, and, in some embodiments, through a tensioning mechanism (which may be a silicon tensioner as is used commercially, or a spring tensioner as is disclosed in U.S. Pat. No. 6,179,863) from whence it terminates in another free end (not shown). A holding sleeve or tag 110, e.g., a stainless steel tube; like that of the '827 patent, is crimped onto the filament section 34D so that it engages the proximal end of the tamper 106 to hold that member in place. The holding sleeve/tag 110 causes the tamper 106 to be removed during deployment of the closure device 20 in the recipient.

As is illustrated in FIG. 2, filament sections 34B and 34C form a loop 60. The inner diameter of loop 60 is variable and loop 60 is easily tightened because filament section 34C easily slides through loop 50A. This aspect is described in greater detail below.

In another embodiment, filament 34 may be attached to a ring (collectively referred to as a collar, as will be detailed below) in place of loop 50A. As with the loop 50A, the ring is dimensioned and configured to permit filament section 34C to easily slide through the ring. Any system that will permit the interior of loop 60 to be tightened may be utilized in some embodiments.

Herein, the term collar includes the loop 50A, a ring, or any other component that slides along filament section 34C/that permits filament section 34C to be slid through the collar to tighten loop 60.

Figure 3:
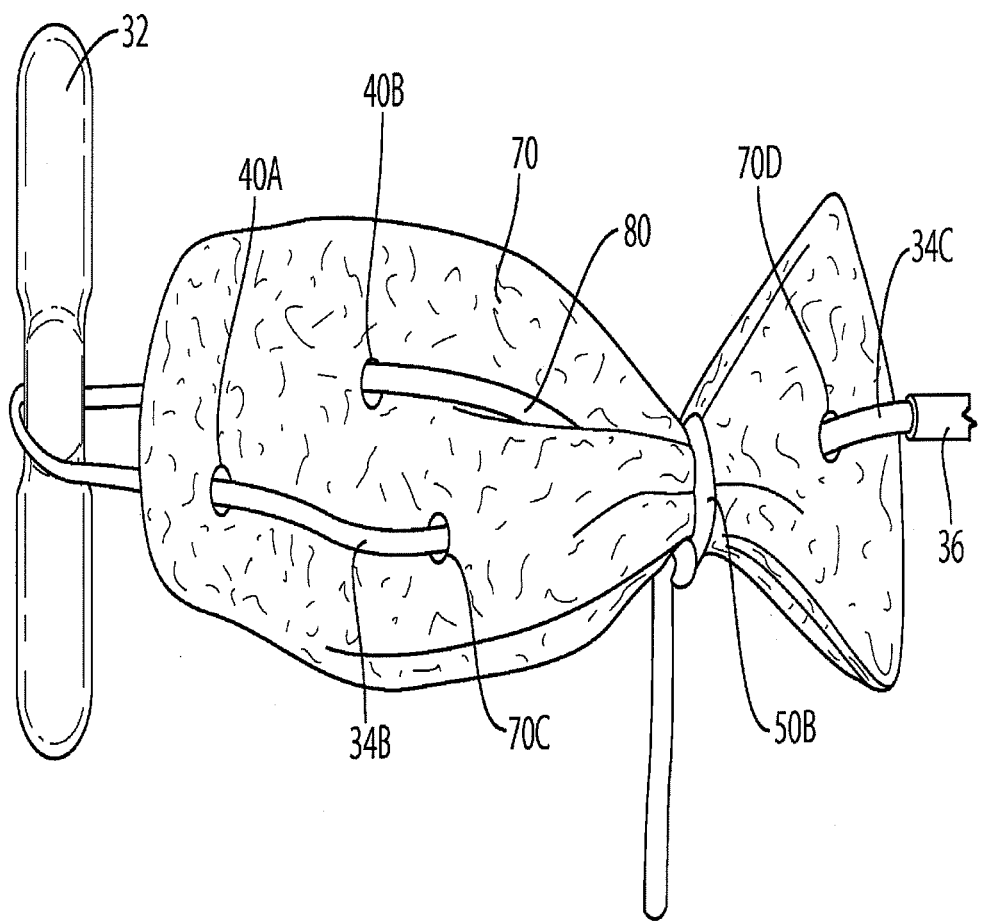
FIG. 3 depicts a closure device according to another embodiment.

FIG. 3 depicts an alternate embodiment, where one end of filament 34 is tied in a knot around plug 70. Plug 70 may be made of the same material as plug 30 described above, and may have the same exterior dimensions as plug 30. As can be seen in FIG. 3, starting from one end of filament 34, the filament 34 is formed into a loop 50B located between lock 36 and anchor 32. As compared to loop 50A, loop 50B surrounds both filament section 34C and plug 70. Plug 70 is positioned between loop 50B and filament section 34C. In an embodiment, plug 70 may be partially or fully wrapped around filament section 34C at the location proximate loop 50B, or may not be even partially wrapped around filament section 34C at the location proximate loop 50B. Loop 50B is configured so that loop 50B, along with the portion of plug 70 proximate the loop 50B, may easily move along filament section 34C. Thus, loop 50B may be loosely tied around filament section 34C and plug 70. Loop 50B is configured so as to not further tighten about filament section 34C and plug 70 (after it is initially wrapped around section 34C). Loop 50B may be formed according to any of the methods used to form loop 50A detailed above, and, in an embodiment, functions in the same manner as loop 50A, except for the fact that it is wrapped around the plug 70 and filament section 34C, as opposed to just filament section 34C.

In the embodiment of FIG. 3, filament section 34B of the filament 34 extends from loop 50B to the anchor 32. Between loop 50B and the anchor 32, filament section 34B passes through apertures 70A and 70C in plug 30. Filament section 34B extends through passageway 32B in anchor 32 to join filament section 34C. Filament section 34C of filament 34 extends from the passageway 32B in the anchor 32 to the plug 30, where it passes through apertures 70B and 70D and an intermediary aperture (not shown in FIG. 3) in the plug 30. Section 34C extends, along with a portion of plug 70, through loop 50A. In an embodiment, section 34C may extend through one, two or three or more apertures, or may not extend through any apertures, in plug 70. Section 34C further extends through lock 36 to join filament section 34D. Filament section 34D extends as described above with respect to FIG. 2.

As is illustrated in FIG. 3, filament sections 34B and 34C form a loop 80. The inner diameter of loop 80 is variable and loop 80 is easily tightened because filament section 34C easily slides through loop 50A. This aspect of the embodiment of FIG. 3 is described in greater detail below.

Figure 4:
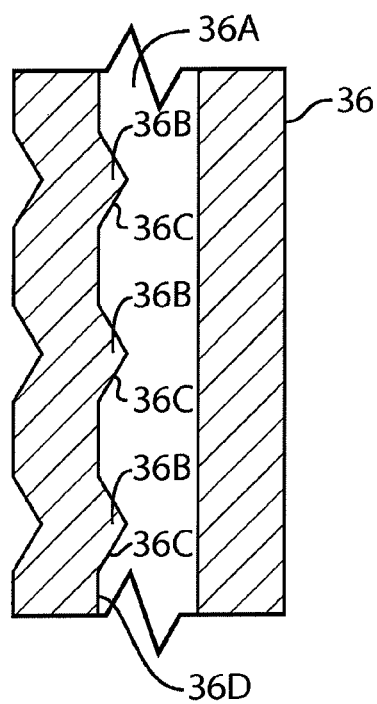
FIG. 4 depicts a lock according to an embodiment.

Referring to FIG. 4, the lock 36 comprises a cylinder including a bore 36 through the longitudinal axis of the cylinder, extending from its proximal side to its distal side. The filament 34 extends through bore 36, as may be seen in FIG. 5. In an alternate embodiment, the lock 36 may be a disk or washer-like member. In an exemplary embodiment, the lock 36 is formed of (i.e., it substantially comprises) a resorbable material, such as members of the PLLA or PGA family of synthetic polymers, or a bio-corrodible material such as iron or magnesium or another type of metal. In an alternate embodiment, the lock 36 is made from (i.e., it substantially comprises) a non-resorbable material such as, for example, stainless steel, titanium, etc.

Figure 5:
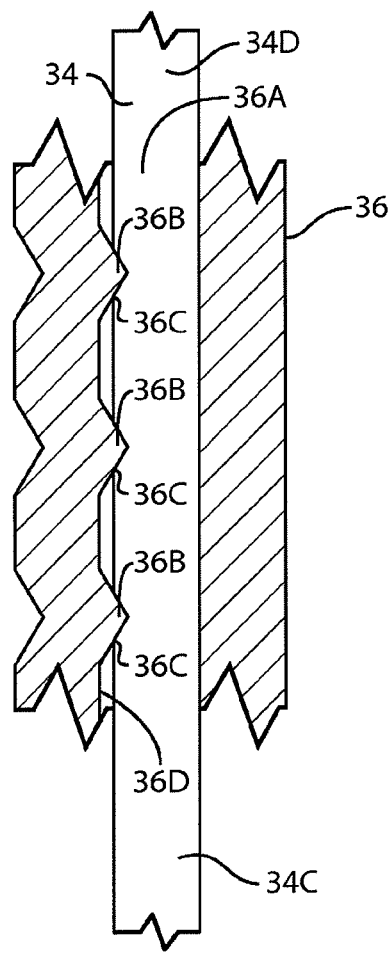
FIG. 5 depicts the lock of FIG. 4 in application.

In the embodiment illustrated in FIGS. 4 and 5, the lock 36 is configured to slide, with resistance, along filament 34. In an embodiment, this resistance is a result of friction between lock 36 and filament 34 created by an interference between the filament 34 and the lock 36. In the embodiment illustrated in FIGS. 3 and 4, this interference is achieved due to protrusions 36B protruding into the bore 36A.

According to the embodiments presented herein, the lock 36 has an outer diameter, when measured normal to the longitudinal axis of the lock 36, which is greater than the corresponding interior diameter of loops 50A and 50B. This permits the lock 36 to lock the closure device 20 in place, as the loops 50A and 50B cannot slip past the lock 36, as will be described in greater detail below.

In an embodiment, filament section 34B is directly attached to the lock 36 instead of to the loop 50A (or collar). The lock 36 may include an orifice through which loop 50A may be looped, thus connecting filament section 34B to the lock 36. In an embodiment, the lock 36 may include a flange or the like including the orifice. In such embodiments, movement of the filament section 34C through/along lock 36 reduces the diameter of the loop 60, just as moving the filament section 34C through loop 50A reduces the diameter of the loop 60.

Still referring to FIGS. 4 and 5, as may be seen, the protrusions 36B protrude into the bore 36A. The protrusions 36B are shaped such that, with respect to the longitudinal axis of the bore 36, surfaces 36C of the protrusions 36B taper from an interior surface 36D of the bore 36, away from the interior surface 36D, and then taper back to the interior surface 36D.

As illustrated in FIG. 5, the protrusions 36B locally reduce the interior diameter of bore 36A to a diameter that is less than a corresponding local diameter of filament 34. Filament 34 is formed of a pliable material that may be locally compressed (e.g., by the protrusions 36B) but also provides resistance to that local compression by the protrusions 36B when lock 36 is moved downward along filament 34 from filament section 36D to filament section 36C. This permits the lock 36 to be moved downward but only upon application of a force to the lock. That is, the resistance to the local compression means that a force must be applied to lock 36 to move lock 36 along filament 34. This force is sufficiently high enough for lock 36 to be used to lock the plug 30 in place, as will be described in greater detail below.

In an embodiment, the lock 36 is crimped such that, with respect to the filament 34 with which it is used, to move the lock 36 along the filament 34, a force of about 0.25 to 0.5 pounds must be applied to the lock 36. In some embodiments, a force of about 0.75 pounds or about 1 pound must be applied to the lock 36 to move the lock. This force is measured as applied in the direction of the longitudinal axis of the lock 36, and is necessary to overcome the friction between the lock 36 and the filament 34. These measurements are taken when filament 34 is prevented from moving in the direction of the force.

Figure 6:
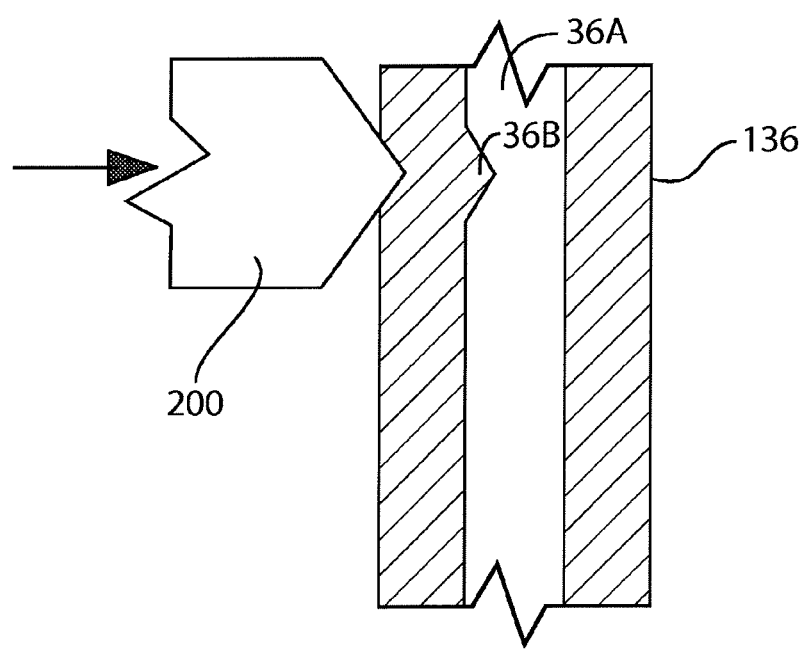
FIG. 6 depicts a method of making the lock of FIG. 4.

In an exemplary embodiment, as illustrated in FIG. 6, the protrusions 36B are formed by crimping a cylinder of an embryonic lock 136 from the outside longitudinal surface of the cylinder of the embryonic lock utilizing a crimping tool 200. In an embodiment, a press-crimp as depicted in FIG. 6 is utilized. As may be seen, a force is applied to embryonic lock 136 via crimping tool 200 sufficient to locally collapse a portion of the embryonic lock 136 so that the protrusions 36B are formed in the bore 36A. In an embodiment, the crimping tool 200 is configured to apply counter-pressure on the embryonic lock 136 so that other portions of the embryonic lock 136A do not collapse.

In the embodiment depicted in FIG. 6, the protrusions are provided in the embryonic lock 136 one at a time. However, in another embodiment, a crimping operation includes providing the protrusions in pairs, in triplets, etc., or all at the same time.

Figure 19B:
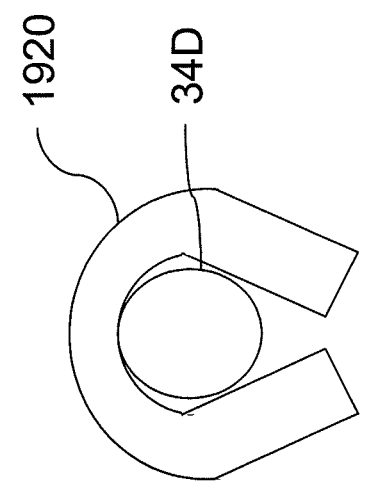
FIG. 19B depicts a lock made from the embryonic lock of FIG. 19A
Figure 19A:
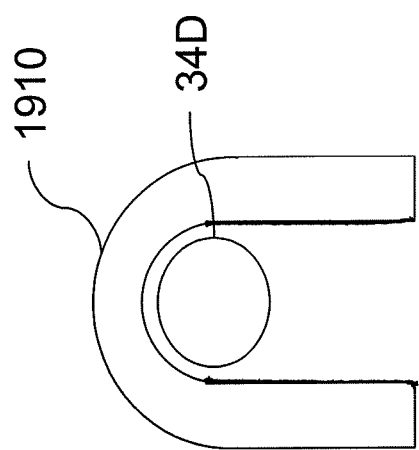
FIG. 19A depicts an alternate embodiment of an embryonic lock.

FIGS. 19A and 19B present an alternate embodiment of a lock usable in some embodiments of the present invention. As may be seen, embryonic lock 1910 is in the form of a U shape instead of a cylinder with a bore. The legs of the U may be crimped as seen in FIG. 19B such that the interior of the embryonic lock 1910 collapses about filament 34D, thereby creating a friction fit between lock 1920 and filament 34. In an embodiment, the interior surface of the lock 1920 may be perforated or the like to enhance the friction fit between lock 1920 and filament 34.

Figure 17:
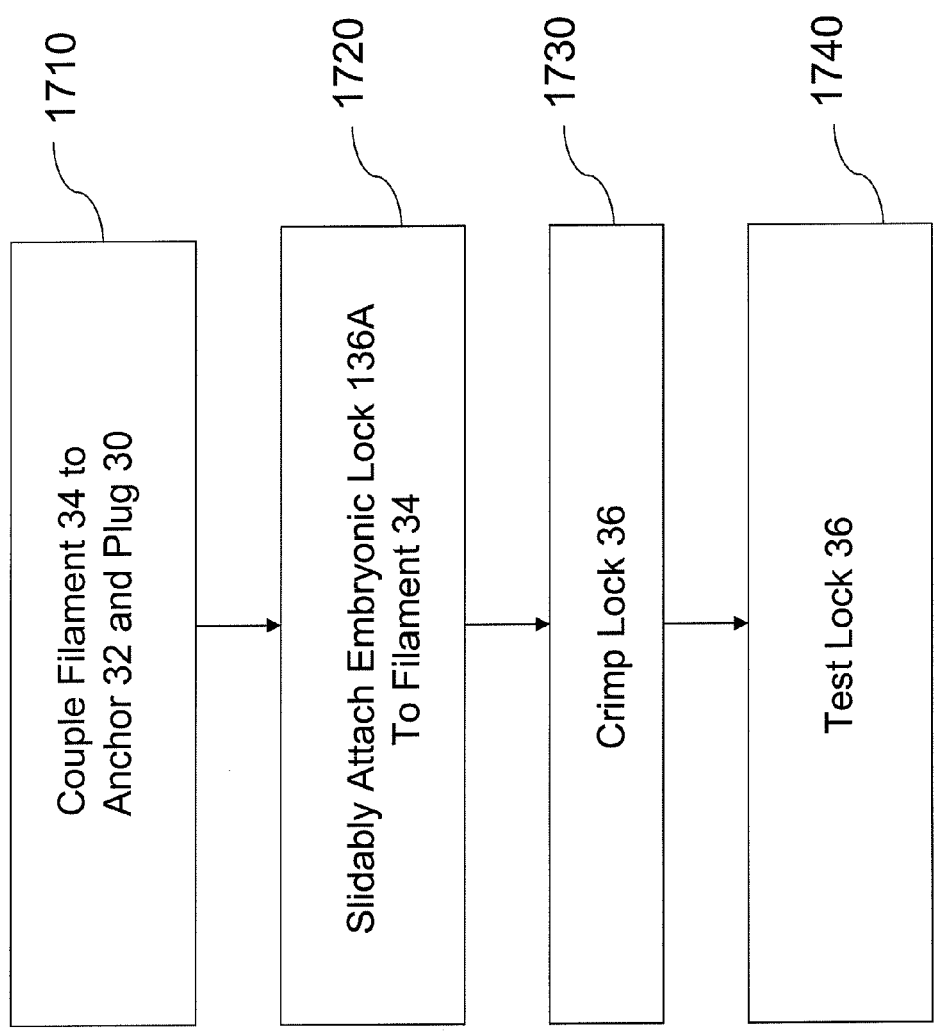
FIG. 17 depicts a flowchart for a method of assembling a closure device according to an embodiment of the present invention.

An embodiment of the present invention includes a method of making a closure device for sealing a percutaneous puncture in a wall of a body passageway of a living being, such as artery 26. By way of example, with reference to the flowchart of FIG. 17, the method comprises, as applied to the closure device detailed herein, at step 1710, coupling filament 34 to anchor 32 and to plug 30 such that the filament forms loop 60 extending through a portion of the anchor 32 and a portion of the plug 30. Proceeding to step 1720, embryonic lock 136A is slidably attached to filament 34 such that movement of filament 34 relative to embryonic lock 136A in a first direction reduces an interior diameter of the loop 60, thereby drawing anchor 32 closer to at least a portion of the plug 30. It is noted that in some embodiments, an end of filament 34 is threaded through bore 36A to slidably attach embryonic lock 136A to filament 34. In other embodiments, where embryonic lock 136A is a U shaped component as detailed above, the legs of the U straddle the filament 34.

Proceeding to step 1730, embryonic lock 136A is crimped to form lock 36 such that lock 36 frictionally engages filament 34 so that lock 36 is slidable along filament 34 only in response to application of a force on lock 36 that overcomes the frictional engagement.

The method optionally includes step 1740, which entails testing lock 36. Specifically, an embodiment of the present invention includes testing and/or evaluating the crimped embryonic lock 136 (or lock 36) to determine or otherwise verify the acceptability of the force that will be required to move the resulting lock 36 along the filament 34 after crimping, or, more precisely, after a first crimping operation. The force may be measured as detailed above. If it is determined that an unacceptably low force may be applied to move the lock 36 along filament 34 (i.e., the lock 36 does not sufficiently lock in place), after a first crimping operation, a second crimping operation may be performed. This second crimping operation may be performed either at the location of the first crimping operation on the embryonic lock 136/lock 36 (thus further driving the protrusion into the bore) or at another location on the embryonic lock 136/lock 36 (thus resulting in an additional protrusion in the bore). After this second crimping operation, a second test may be performed to determine or otherwise verify the acceptability of the force that will be required to move the resulting lock 36 along the filament 34 after this second crimping operation. These steps may be continued until an acceptable lock 36 is obtained. Further, in an embodiment, this method ensures that each closure device operates as desired, regardless of variation in the features of the component parts (e.g., out of tolerance embryonic locks 136, etc.). Further, if the testing determines/reveals that an unacceptably high force must be applied to move the lock 36 along the filament, the tested closure device may be rejected. Embodiments of the present invention include manufacturing the device whereby the amount of frictional engagement between the lock and filament may be precisely controlled during manufacture.

Figure 11:
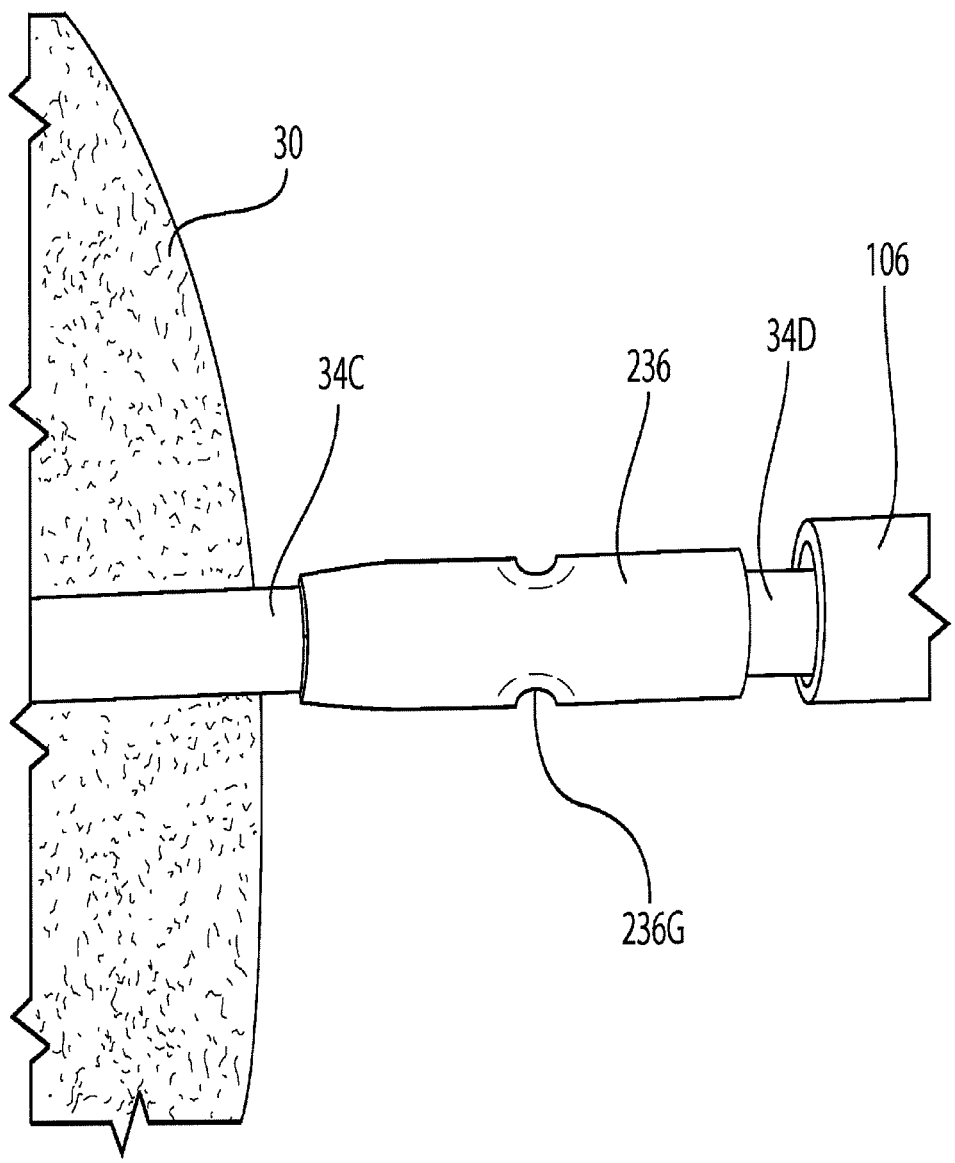
FIG. 11 depicts a lock according to an alternate embodiment.

FIG. 11 depicts an exemplary embodiment of a lock 236 manufactured according to a crimping operation just described. FIG. 11 depicts crimp locations 236G formed by crimping tool 200, where corresponding protrusions (not shown) may be found on the interior of lock 236.

In an embodiment, the crimping operation includes utilizing a machine that manually and/or automatically crimps the embryonic lock 136 and/or that provides automatic feedback with respect to the features of the crimp. By way of example, the machine could gauge the depth to which the protrusions enter the bore 36A. The machine may gauge the force applied during the crimping operation. Further by way of example, the machine could gauge the force that is necessary to apply to the lock 36 to move the lock along the filament 34. These features may be used to help assure the quality of the closure devices 20 and to help assure that the closure devices 20 will work as desired. For example, the gauged depths, forces, etc., may be compared to predetermined depths, forces, etc., to determine whether the quality is acceptable. In an exemplary embodiment, all of these actions may be performed automatically.

While filament 34 is not depicted in FIG. 6, in most embodiments, filament 34 will be located within bore 36A of embryonic lock 136 during the crimping operation. Because the filament 34 is pliable, the filament 34 will not be damaged during the crimping operation.

Figure 12A:
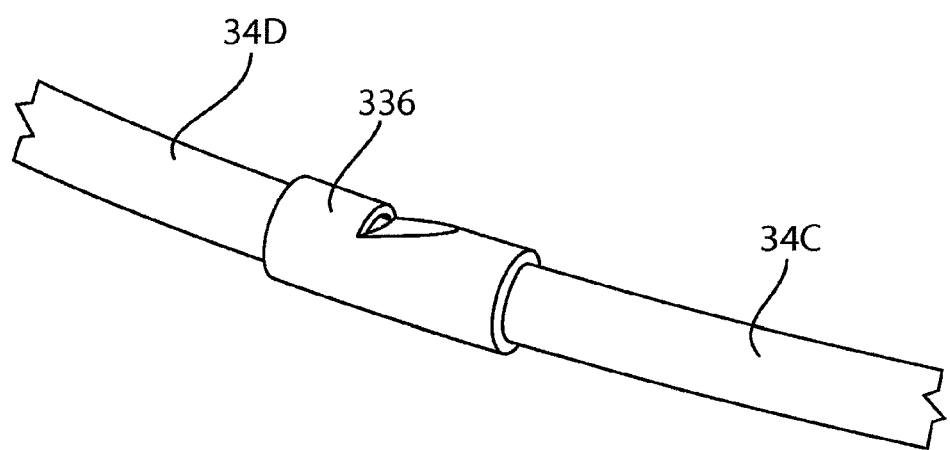
FIG. 12A depicts a lock according to an alternate embodiment.
Figure 12B:
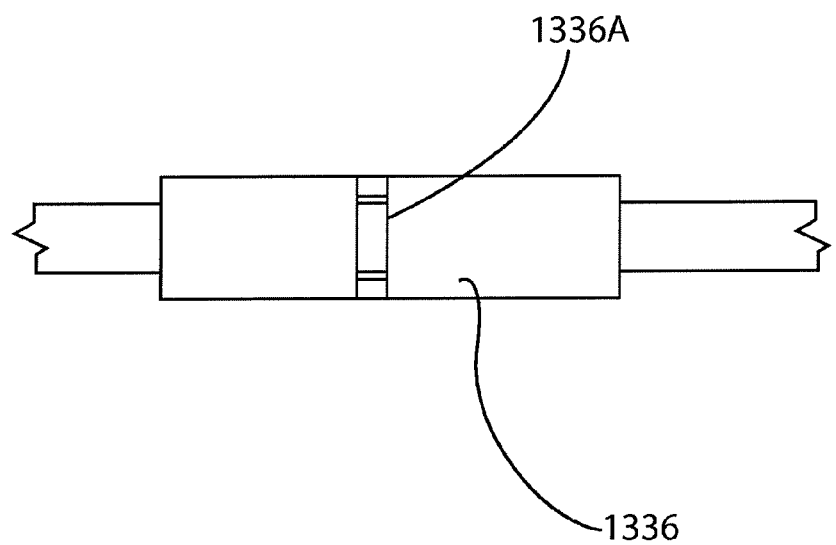
FIG. 12B depicts an embryonic lock used to make the lock of FIG. 12A.

Sections of the embryonic lock 136 may be removed prior to crimping to permit the crimping operation to be more easily performed. By way of example, laser cut slots may be formed in an embryonic lock to make the embryonic lock more bendable at those locations. In this regard, FIG. 12A depicts an exemplary embodiment of a lock 336 after crimping. Lock 336 is formed from an embryonic lock 1336, as may be seen in FIG. 12B, where slot 1336A is present in the surface of embryonic lock 1336.

Figure 13A:
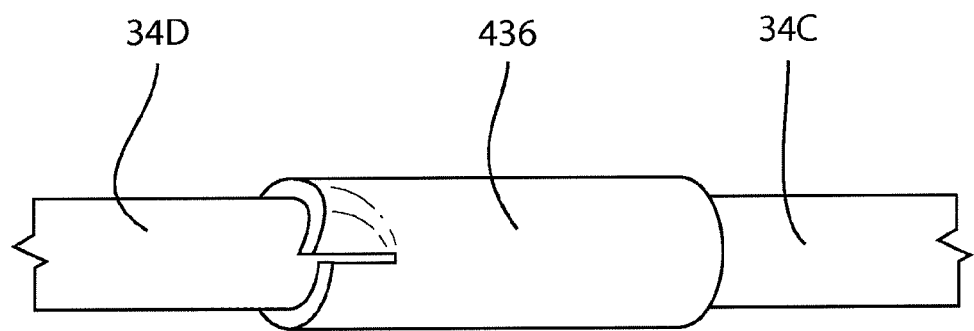
FIG. 13A depicts a lock according to an alternate embodiment.
Figure 13B:
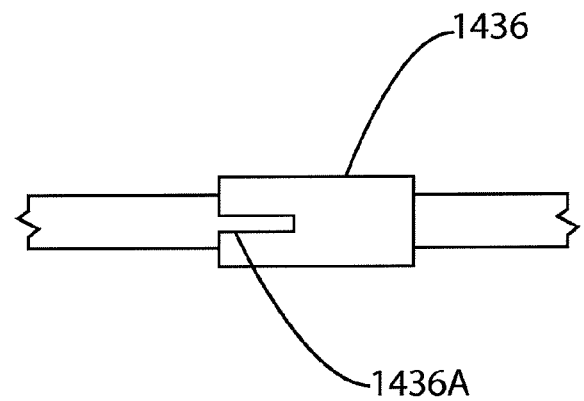
FIG. 13B depicts an embryonic lock used to make the lock of FIG. 13A.
Figure 13C:
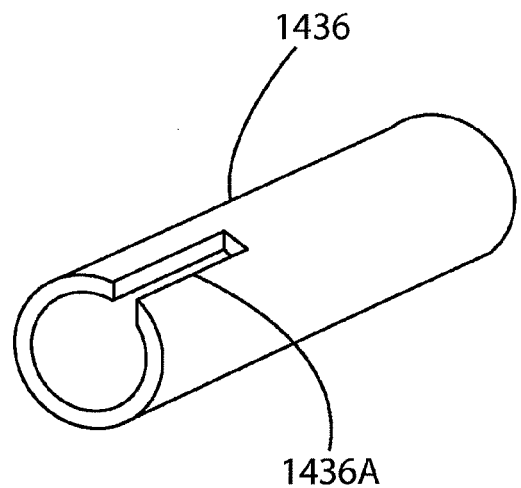
FIG. 13C depicts an isometric view of the embryonic lock of FIG. 13B.
Figure 14A:
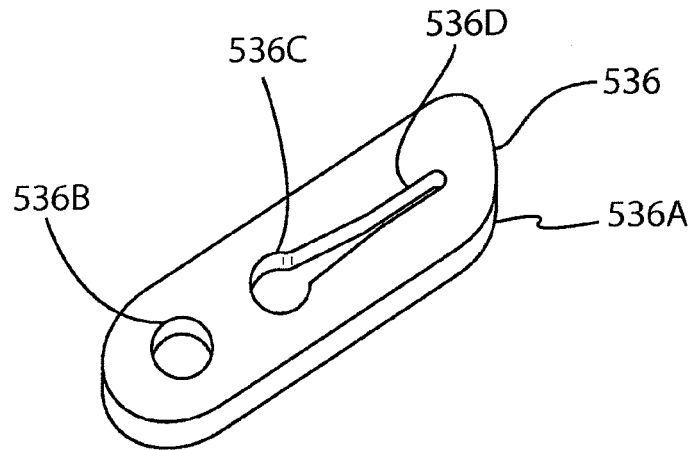
FIGS. 14A-14E depict a lock according to an alternate embodiment.
Figure 14B:
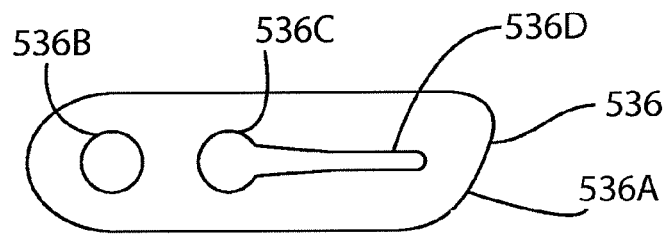
Figure 14C:
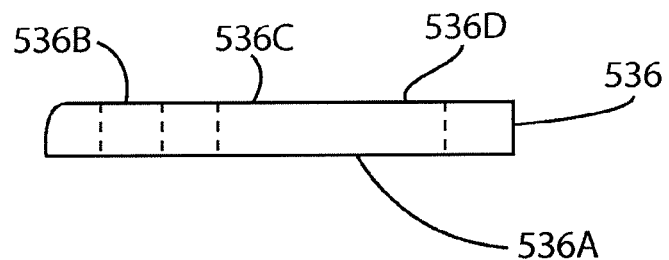
Figure 14D:
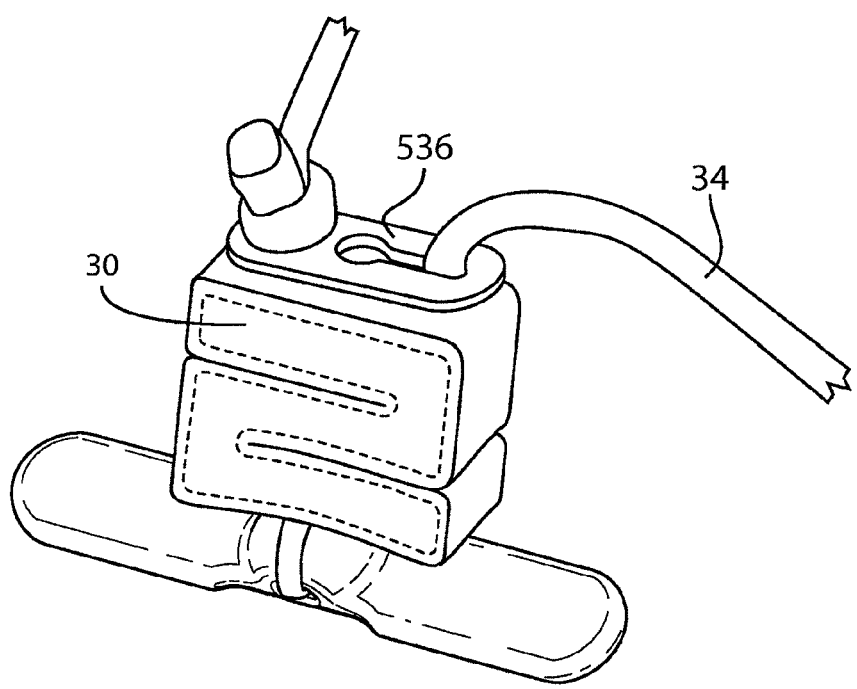
Figure 14E:
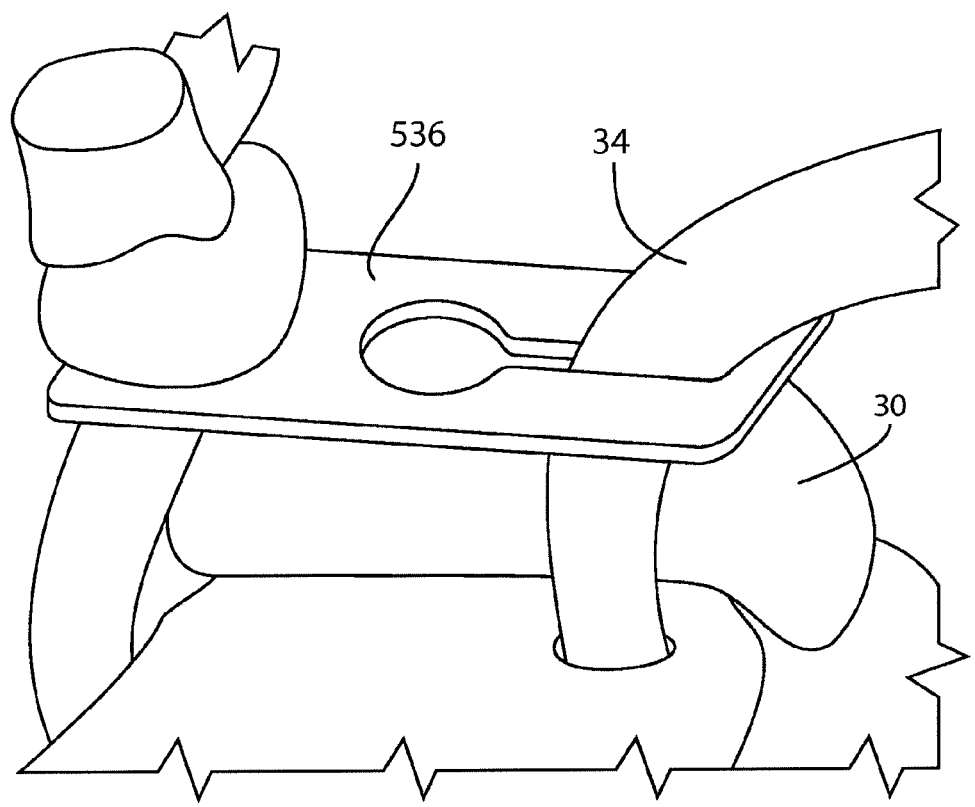

Still further, FIG. 13A depicts an exemplary embodiment of a lock 436 after crimping. Lock 436 is formed from an embryonic lock 1436, as may be seen in FIG. 13B, where slot 1436A is present in the surface of embryonic lock 1436. FIG. 13C presents an isometric view of embryonic lock 1436 of FIG. 13B. In an embodiment, the slot 1436A may be angled with respect to the longitudinal axis of the embryonic lock 2436. As will be understood, the locks depicted herein may be used in place of lock 36 as described herein.

Figure 20:
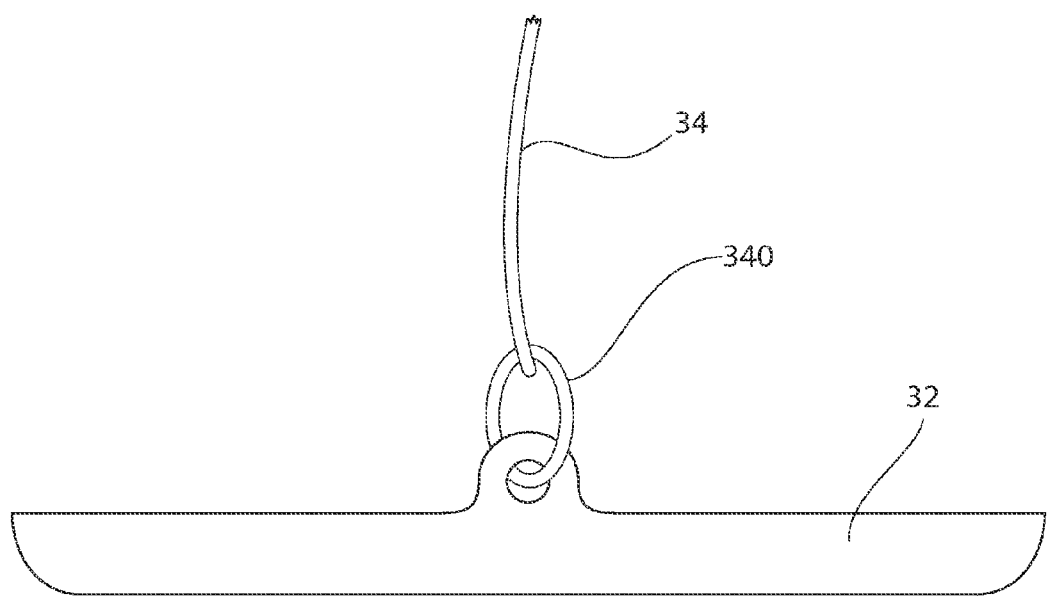
FIGS. 20 and 21 depict exemplary embodiments of components of the closure device including radio opaque components.
Figure 21:
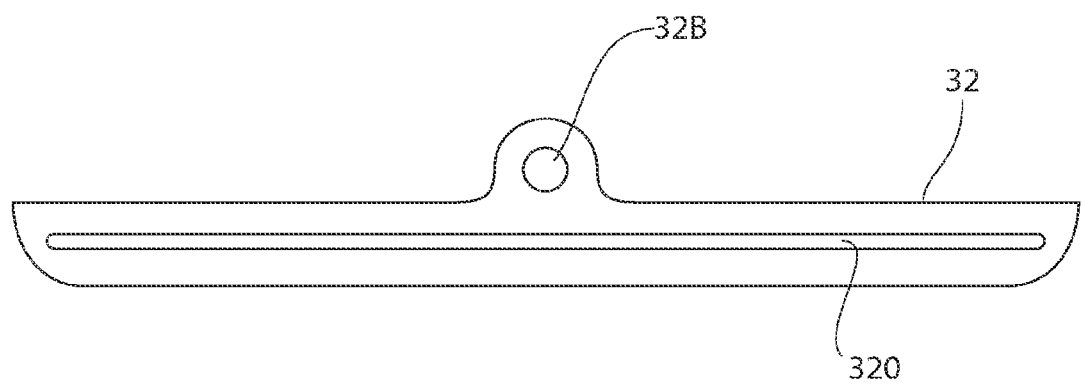

In an exemplary embodiment, the locks, such as lock 36, used with the closure device 20 may be made from iron or other appropriate resorbable material. In an exemplary embodiment, the lock may be made of a bio-absorbable polymer. Any material may be utilized so long as it is compatible with a human and can provide sufficient resistance to movement along the filament while also permitting movement along the filament and retaining loops 50A/50B in place as disclosed herein. In an embodiment, PLLA might be used to make at least some of the components of the device. Further, in an embodiment, pure or substantially pure iron is used to make the lock. In an embodiment, a radio opaque material (e.g., iron, stainless steel, and possibly magnesium, etc.) is utilized to form the lock. This permits fluoroscopy or other non-invasive inspection regimes to be performed during and after insertion of the device to validate that the closure device has been properly inserted. In an alternate embodiment, the collar 50A is also made from a radio opaque material (e.g., iron, stainless steel, and possibly magnesium, etc.) is utilized to form the lock. In yet other alternative embodiments, a radio opaque material (e.g., iron, stainless steel, and possibly magnesium, etc.) may be added into or proximate to the anchor 32. For example, the anchor 32 may be formed around at least part of a radio opaque component and/or the filament 34 may extend through a radio opaque component located between dome 32A of anchor 32 and plug 30, etc. FIG. 20 depicts an iron ring 340 fitted thorough dome 32A, through which filament 32 extends (in other embodiments, filament 34 extends through the anchor 32 as detailed above with respect to FIG. 1B above, and the iron ring 340 also extends as shown in FIG. 20. FIG. 21 depicts an iron component 320 embedded in anchor 32. This component 320 may be molded into the anchor 32 during the molding process that may be used to form anchor 32. In this embodiment, the iron component 320 provides little, if any, structural support to the anchor 320.

Such embodiments utilizing radio opaque material as detailed herein permit a method of verifying that the lock 36 is properly positioned relative to the collar 50A using a non-invasive inspection regime. By way of example, after the closure device 20 is fully deployed (e.g., as shown in FIG. 1B), a radiological image such as an X-Ray image taken of the recipient can be analyzed to determine the relative positions of the collar 50A and/or the lock 36 and/or the anchor 32, if the respective components include radio opaque material in sufficient quantities. This will indicate the quality of the deployment of the closure device 20 in the recipient. For example, if the X-Ray image reveals that the collar 50A is adjacent lock 36 in an embodiment where the collar 50A is positioned at the proximal end of the plug 34, it can be assumed that the closure device has been properly applied. It is noted that any radio opaque material located at any appropriate location may be utilized in some embodiments of the present invention. In some embodiments, instead of iron, the radio opaque components may be stainless steel. Foil patches may be utilized, providing that the foil patch is sufficiently radio opaque. These may be "patched" over various components of the closure device 20. For example, in the case of a collar made of PLA material or the like, the radio opaque foil may be patched over or around the collar.

As disclosed herein, the locks, such as lock 36, are made from embryonic locks in the form of elongated cylinders, and the locks retain the general characteristics of an elongated cylinder once formed. Other embodiments may include locks of different shapes. For example, locks in the general forms of rings, circular plates (with dimensions analogous to a hockey puck), balls, boxes, rectangles, etc., may be used. Any shape may be utilized so long as it is compatible with a human and can provide sufficient resistance to movement along the filament while permitting movement along the filament and retaining the loops 50A/50B in place as disclosed herein.

FIGS. 14A-14E depict a lock 536 which may be used as an alternate to lock 36. As may be seen in these figures, lock 536 includes an elongated plate 536A with holes 536B and 536C extending therethrough. Holes 536B and 536C are dimensioned to permit filament 34 to easily slide therethrough. Hole 536C includes slot 536D which is configured to act in an analogous manner to the protrusions of lock 36 described above. Specifically, the slot 536D is narrower than the natural outer diameter of filament 34, and thus provides a limited resistance to movement of filament 34 through the slot. Lock 536 may function by taking advantage of the fact that when the loop 60 is relatively large, the filament 34B is essentially parallel to the filament 34C. As the loop 60 is reduced in interior diameter, the angle between filament 34B and 34C increases, and thus the filament 34B is driven further into slot 536D away from hole 536C. In an embodiment, slot 536D becomes gradually narrower with movement away from hole 536C, thus locking the filament 34b in place. In another embodiment, slot 536D has a relatively constant width and does not substantially taper and/or the width is relatively constant beyond the portions proximal of hole 536C.

Deployment of the closure device 20 by the deployment instrument 100 with respect to the embodiment of FIG. 2 will now be described. It will be appreciated, however, that the deployment methods disclosed herein are applicable to deploying the embodiment of FIG. 3.

The deployment instrument is inserted into introducer sheath (which had been previously positioned in the same manner as described in the '827 patent), so that the tube 104 of the carrier tube 102 passes through the hemostasis valve (not shown) of the introducer sheath (not shown). The deployment instrument is then pushed fully down the introducer sheath, whereupon the tube remains in the sheath and the anchor 32 is deposited in the artery 26 beyond the distal end of the introducer sheath. The deployment instrument is then operated to determine if the anchor 32 has been properly deployed. To that end, the introducer sheath is held by the user to prevent axial movement and the instrument is carefully withdrawn from it. This action causes the anchor 32 to engage or catch on to the distal end of the introducer sheath. As the anchor catches on the distal end of the introducer, resistance will be felt by the user to indicate appropriate deployment of the anchor as described in the '827 patent.

Once the anchor 32 has been properly deployed, the plug 30 (or plug 70) is deployed into the puncture tract. To that end, the introducer sheath and the deployment instrument are held together and withdrawn as a unit from the puncture. This action causes the anchor 32 to engage or catch onto the inner surface of the artery 26 wall contiguous with the opening 24A. The introducer sheath and the instrument are then pulled further outward. Inasmuch as the anchor is trapped against the interior of the artery wall, the continued retraction of the introducer sheath and deployment instrument causes the filament 34 to pull the plug 30 (or plug 70) out of the carrier tube 102 of the deployment instrument and into the puncture tract 24B. As the introducer and deployment instrument come out of the puncture tract, continuous steady resistance will be felt as the tensioner assembly of the deployment instrument controls the force on the filament 34 during the retraction procedure.

Continued retraction of the introducer and the instrument brings the tamper 106 out of the free end of the instrument because the tag 110, which is fixed to the filament 34, pushes the tamper out of the introducer.

The retraction of the introducer sheath and the deployment instrument carries the plug 30 into engagement with the exterior of the artery wall immediately adjacent the opening 24A. Continued retraction causes the filament 34 to deform the plug 30 (or plug 70), i.e., cause it to deform radially outward. In an embodiment, the collagen is forced to fold down after exiting the carrier 102 (in some embodiments, it begins to fold down immediately upon exiting the carrier 102). The existence of blood within the puncture tract further contributes to the deformation of the plug 30 (or plug 70), since its collagen foam expands in the presence of blood. The retraction procedure continues to pull the introducer and instrument up the filament until the tag 110 is exposed. At this point the plug 30 will be located in the puncture tract contiguous with the opening in the artery, and the lock located proximally of the plug. Put another way, to achieve the compaction of the collagen of the plug 30 (or plug 70), the user gently tensions the filament 34 by, for example, pulling on the introducer sheath and instrument in the proximal direction with one hand. This moves loop 50A (or loop 50B) down along filament section 34C as a result of tension on filament section 34B in reaction to the tension on filament 34C. Here, anchor 32 acts in an analogous manner to a pulley as described above. This has the effect of tightening loop 60 (or loop 80). As loop 50A (or loop 50B) moves down filament section 34C to tighten loop 60, it compacts plug 30 (or plug 70). This forces plug 30 (plug 70) to conform to the artery contiguous with the opening 24A.

Next, the tamper 106 is manually slid down the filament section 34D by the user's other hand so that it enters the puncture tract 24B and engages the proximal side of the lock 36. A force is applied to tamper 106 sufficient to overcome the resistance to movement of the lock 36 relative to the filament 34 due to the protrusions 36B. This causes the lock 36 to slide down filament section 34D and onto filament section 34C until it abuts loop 50A. As noted above, the lock 36 is configured, when used in conjunction with filament 34, to provide a certain amount of resistance to movement along filament 34. This locks loop 50A (or loop 50B) in place, as the outer diameter of lock 36 is greater than the inner diameter of loop 50A, thus preventing loop 60 from expanding, because, as noted above, the lock 36 has an outer diameter, when measured normal to the longitudinal axis of the lock 36, that is greater than the corresponding interior diameter of loop 50A. This feature causes the plug 30 to be secured in the compact position until hemostasis occurs. That is, because the plug 30 is compressed between the anchor 32 and the lock 36, plug 30 is retained or locked in position within the puncture tract and cannot move away from the anchor, even before the blood clots in the plug.

With respect to the embodiment of FIG. 3, when the force is applied to tamper 106, lock 36 slides down filament section 34D and onto filament section 34C. In an embodiment, lock 36 may enter aperture 70D and continue to slide along filament section 34C unit it reaches loop 50B, where it either may directly contact loop 50B or contact a portion of plug 70 interposed between loop 50B and lock 36. In an alternate embodiment, lock 36 may not enter aperture 70D, and instead push plug 70 along filament section 34C until reaching loop 50B. In this embodiment, the lock 36 will bunch/compress plug 70 as lock 36 moves towards loop 50B.

It should be noted that in an embodiment, during the tamping action, tension on the filament section 34D may be maintained at a load greater than that used on the tamper 106 to ensure that the tamping action does not propel the plug 30 into the interior of the artery.

The locking of the closure device 20 in place is also aided by virtue of the clotting of the hemostatic collagen plug. In this regard within a few hours after deployment, the anchor 32 will be coated with fibrin and thus attached firmly to the arterial wall, thereby eliminating the possibility of distal embolization. After approximately thirty days, only a small deposit of anchor material will remain. Moreover, because the plug 30 is formed of compressed collagen or other hydrophilic material it also expands automatically in the presence of blood within the puncture tract 24A when deployed, thereby further contributing to the plug's enlargement.

As should be appreciated from the foregoing, the deployment of the closure devices of this invention is easy, quick and reliable and anchoring or locking of the closure device in place against accidental displacement is automatic upon tensioning of the filament.

An alternate embodiment of a lock 360 usable in the same manner as lock 36 detailed above will now be described with respect to FIGS. 7-9. In the embodiment illustrated in FIGS. 7 and 8, the lock 360 is configured to more easily slide downward than upward along filament 34. In the embodiment illustrated in FIGS. 7 and 8, this functionality of the lock 360 is achieved due to protrusions 360B protruding into the bore 360A. In an exemplary embodiment, as illustrated in FIG. 9, the protrusions 360B are formed by crimping a cylinder of an embryonic lock 1360 from the outside longitudinal surface of the cylinder of the embryonic lock utilizing a crimping tool 300.

Figure 7:
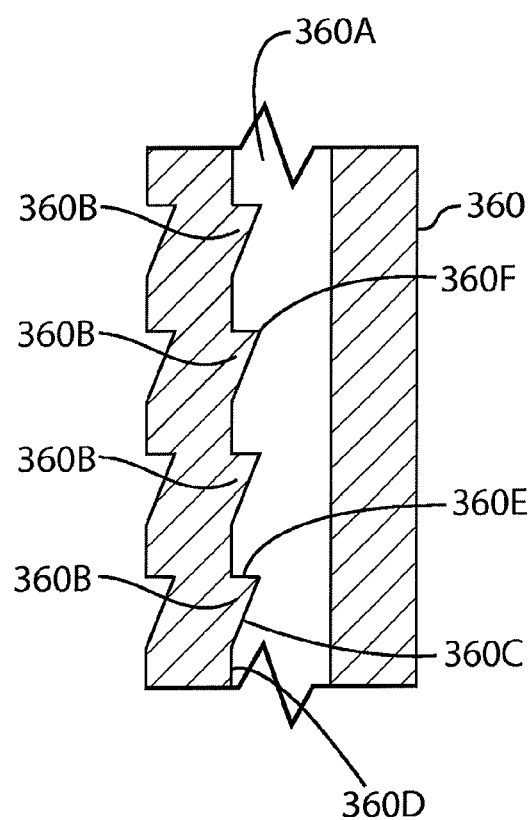
FIG. 7 depicts a lock according to an alternate embodiment.
Figure 8:
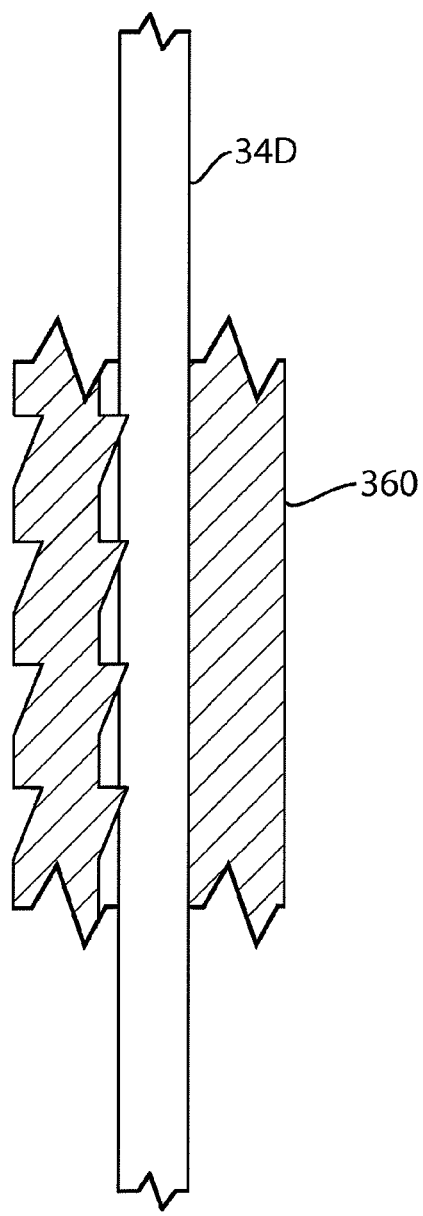
FIG. 8 depicts the lock of FIG. 7 in application.
Figure 9:
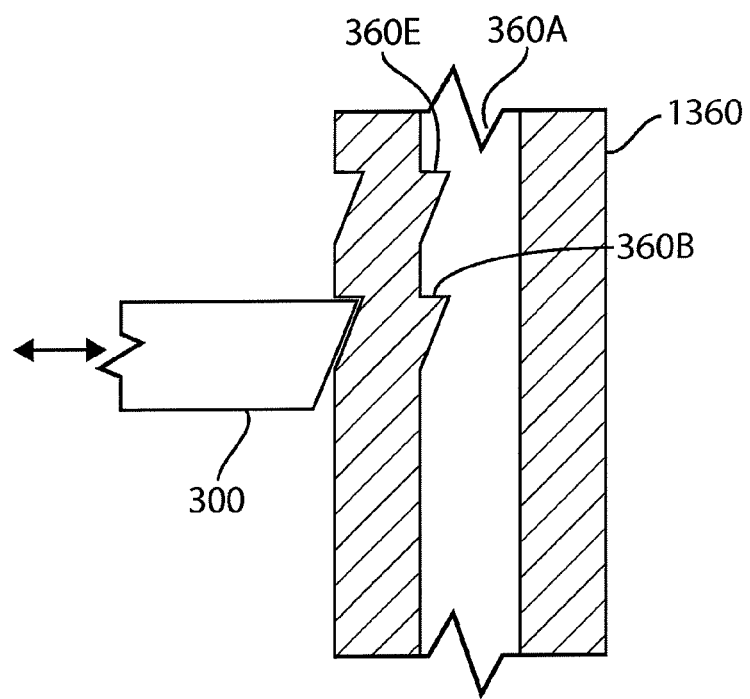
FIG. 9 depicts a method of making the lock of FIG. 7.

As may be seen in FIGS. 7 and 8, the protrusions 360B protrude into the bore 36A. The protrusions 360B are shaped such that, with respect to the longitudinal axis of the bore 360A, one surface 360C of the protrusions 360B tapers from an interior surface 360D of the bore 36. Further, another surface 360E of the protrusions 360B abruptly extend from the interior surface 360D of the bore 360A. The surfaces 360C and 360E meet to form a point at 360F.

As illustrated in FIGS. 7 and 8, the protrusions 360B locally reduce the interior diameter of bore 360A to a diameter that is less than a corresponding local diameter of filament 34. Owing to the gentle taper of surface 360C from interior surface 360D of the bore 36, and point 360F, the lock 36 may more easily slide downward than upward along filament 34. Specifically, as detailed above, filament 34 is formed of a pliable material that may be locally compressed by the gentle taper of surface 360C when lock 360 is moved downward along filament section 360D, thus permitting the lock 36 to be moved downward. However, when an upward force is applied to lock 360, the point 360F will "hook" onto filament section 34D, and will resist upward movement of the lock 36. That is, when this configuration is used, it is analogous to sliding a needle along a cloth, where the needle is held at an acute angle relative to the direction of movement of the needle. The needle will not catch on the cloth when held at the acute angle. However, if the needle is moved in the opposite direction, the needle will catch the cloth, and prevent movement of the needle in that direction. Thus, in the embodiment depicted in FIGS. 7 and 8, the lock 360 is a one-way lock.

Figure 15A:
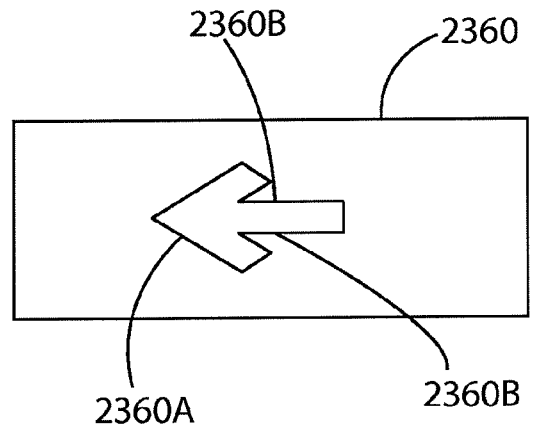
FIG. 15A depicts an alternate embodiment of an embryonic lock.
Figure 15B:
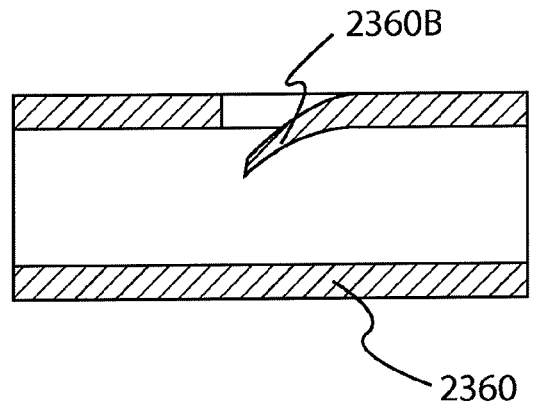
FIG. 15B depicts a lock made from the embryonic lock of FIG. 15A.
Figure 15C:
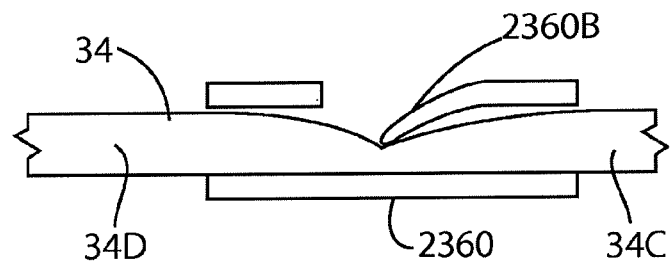
FIG. 15C depicts the lock of FIG. 15B with a filament extending through the lock.

As noted above, sections of the embryonic lock may be removed prior to crimping to permit the crimping operation to be more easily performed. This operation may also be used to make a one-way lock. Referring to FIG. 15A, in an embodiment, an arrow shape 2360A (or a wedge shape or the like) is cut into the exterior of an embryonic lock 2360 such that the "point" of the arrow (or wedge) is generally aligned with the longitudinal axis of the embryonic lock 2360. The area on the "inside" of the arrow, elements 2369B, may be bent inward into the bore of the embryonic lock, as depicted in FIGS. 15B and 15C, thus forming a one-way lock.

Note that in an embodiment, locks 336 and 436 may also be one-way locks, owing to their geometry. The cut slot in the locks may be angled with respect to the transverse axis of the locks to make the edge of the slot more likely to grip into the filament, thus making it easier for the lock to be moved in one direction along the filament as opposed to the opposite direction.

Figure 16A:
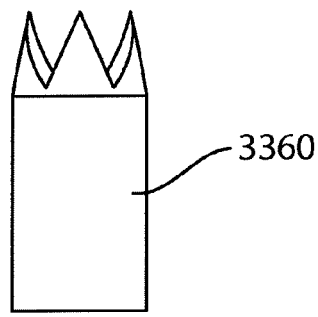
FIG. 16A depicts an alternate embodiment of an embryonic lock.
Figure 16B:
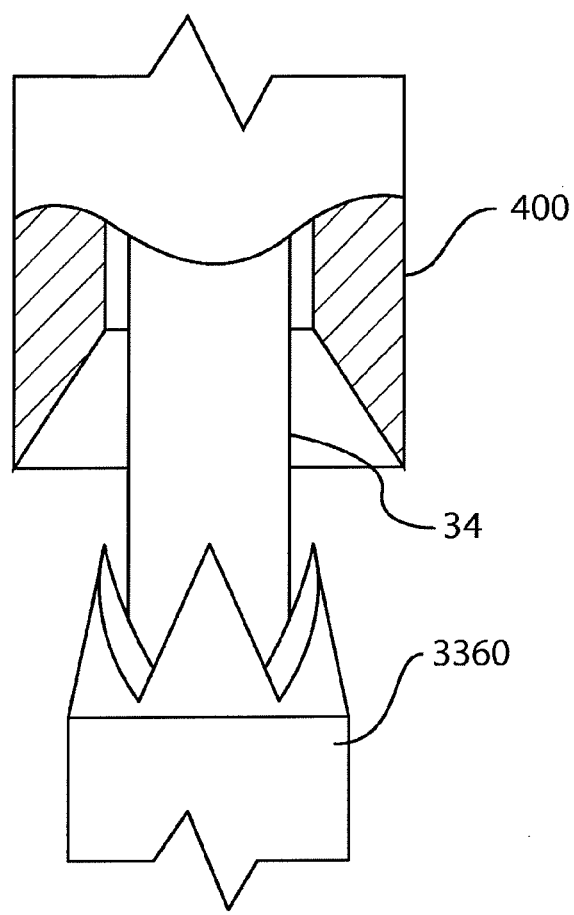
FIG. 16B depicts a method of making a lock from the embryonic lock of FIG. 16A.
Figure 16C:
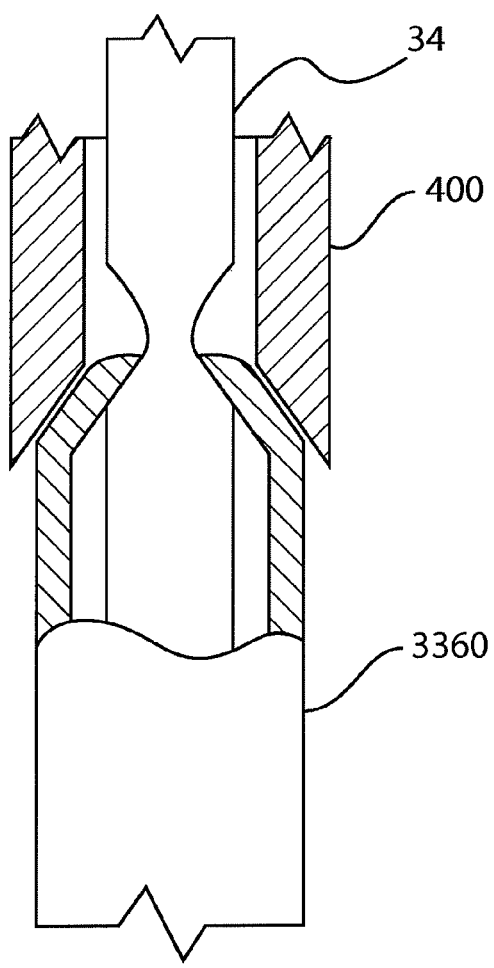
FIG. 16C depicts a lock made from the embryonic lock of FIG. 16A.

Referring to FIG. 16A, an embryonic lock 3360 that has a crown-shape at one end is utilized in an embodiment. Filament 34 is placed through the bore through embryonic lock 3360, and crimping tool 400 is forced downward onto the crown of embryonic lock 3360. Tool 400 has a tapered interior as may be seen, which forces the points of the crown inward towards filament 34, as is depicted in FIG. 16C. In an embodiment, this provides a one-way lock.

In an embodiment, tool 400 is utilized as a tamper used during application of the closure device 20. That is, in an embodiment, tool 400 is substituted for tamper 106, and embryonic lock 3360 is crimped when tool 400 is used as a tamper during application. Thus, embryonic lock 3360 is crimped at the same time that the closure device 20 is locked in place.

Figure 18:
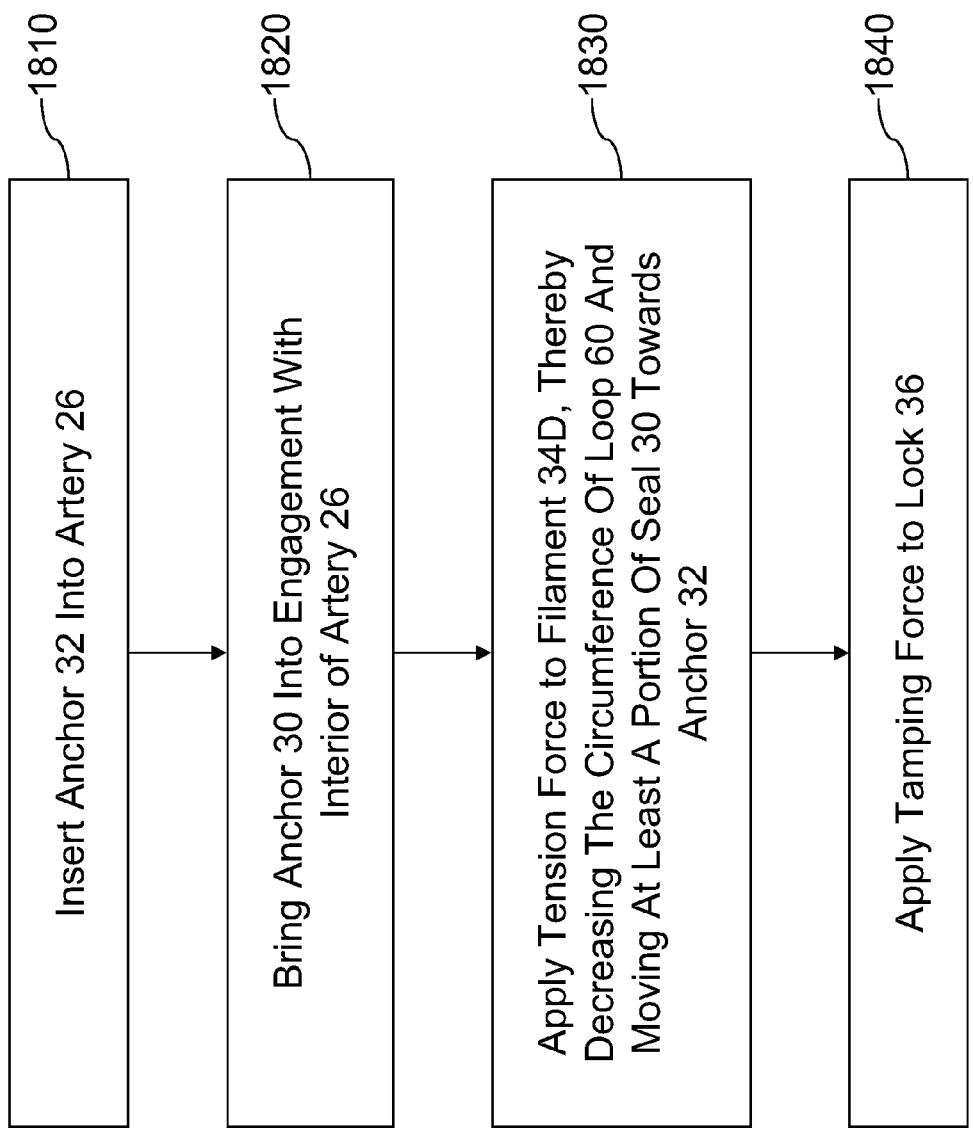
FIG. 18 depicts a flow chart for a method of sealing a percutaneous puncture in a wall of an artery according to an embodiment of the present invention.

In an exemplary embodiment, there is a method of sealing a percutaneous puncture in a body passageway, such as, for example, artery 26, of a living being. Referring by way of example to the flow chart of FIG. 18, at step 1810, anchor 32, coupled to filament loop 60, is inserted in the artery 60 through percutaneous puncture 24. At step 1820, the anchor 32 is brought into engagement with an interior of the artery 26, such as depicted by way of example in FIG. 1B. At step 1830, a tension force is applied to a portion of the filament (e.g., filament 34D) so that a force is applied to the loop 60 tending to decrease the circumference of the loop. The result of step 1830 is to reduce the circumference of the loop 60, thereby moving at least a portion of the seal 30 towards the anchor 32. At step 1840, a tamping force is applied to the lock 36 in a direction towards the loop 60 and in a direction away from the direction of the applied tension to filament portion 34D. The tension applied during step 1830 is maintained during application of the tamping force. This tamping force may be applied by tamper 106 as detailed above, or by any other device, system or method applicable. The applied tamping force is sufficient to overcome the frictional engagement forces so that the lock 60 slides along filament 34D in a direction towards anchor 32. In embodiments of the method utilizing the exemplary closure device detailed herein, the lock 60 resists movement along filament 34D in a direction opposite the direction of the tamping force. This has the effect of preventing the circumference of the loop 60 from expanding relative to the circumference of the loop 60 after application of the tamping force and the tension force.

In an embodiment, the plugs, locks and/or filament configurations disclosed herein may be substituted for the plugs, locks and/or filament configurations of the '827 and/or the '681 patent. Further, the installation methods disclosed in those two patents may be utilized to install the closure devices disclosed herein (in a modified form as necessary to accommodate the closure devices disclosed herein). In this regard, the teachings of the '827 patent and the '681 patent are hereby incorporated by reference for combination with the closure devices disclosed herein.

Figure 22A:
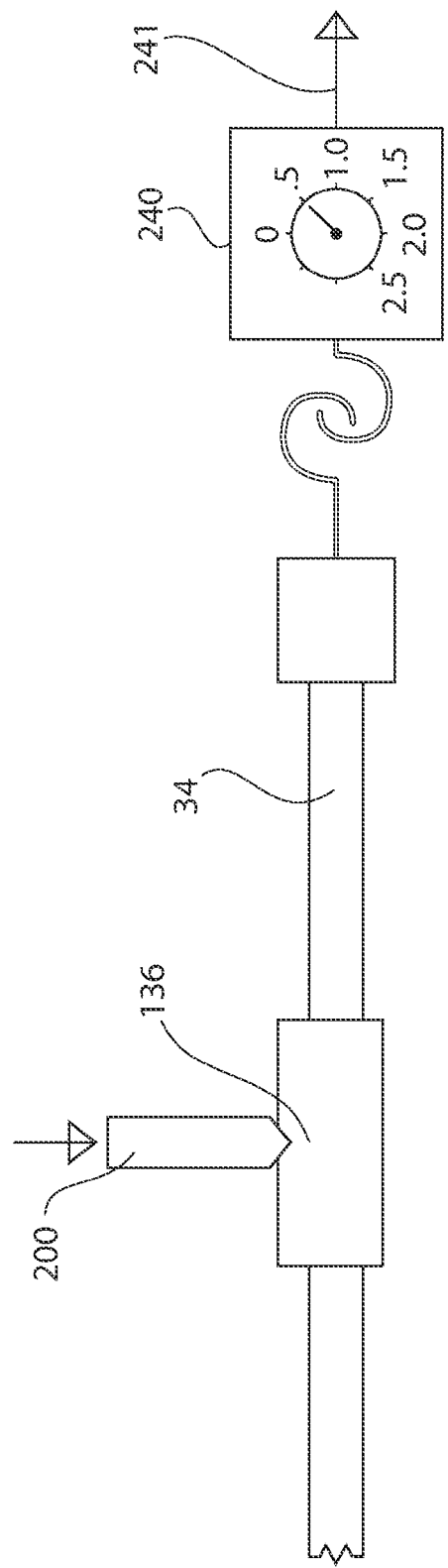
FIGS. 22A-22B depict an exemplary embodiment in which the lock is crimped whereby the requisite friction force between the lock and the filament is controlled.
Figure 22B:
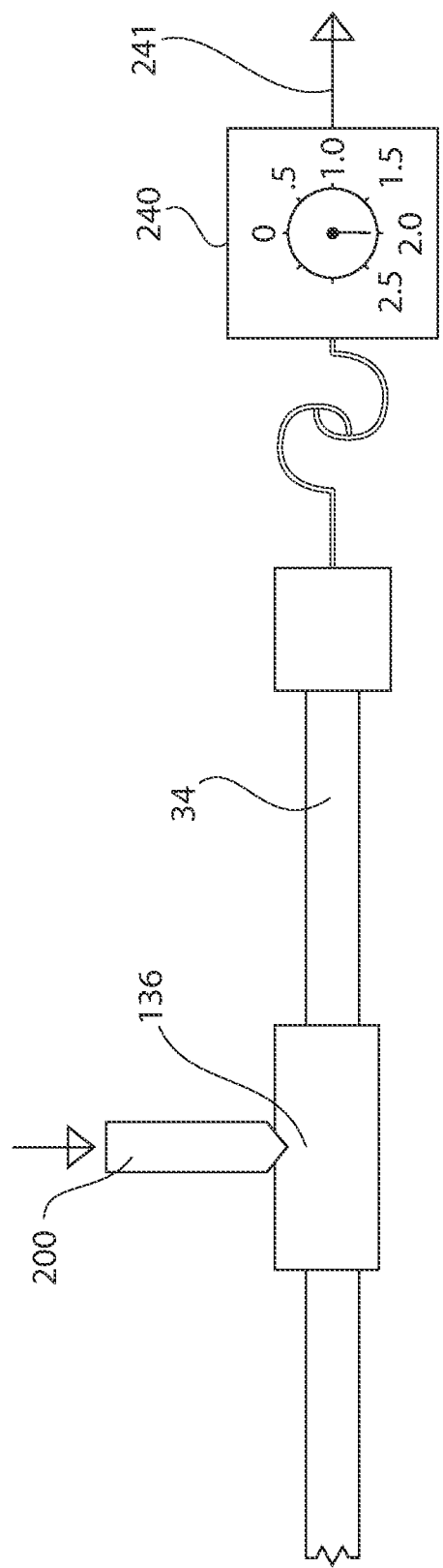

In an exemplary embodiment, there is a method of applying a crimp to an embryonic lock so that the resulting friction force necessary to be overcome to move the resulting lock relative to the filament may be controlled. In an exemplary method, the filament 34 is linked to a force gage as shown in FIG. 22A. A force is applied to the force gage 240 and thus the filament 34 in the direction of the horizontal arrow 241 while the embryonic lock 136 is crimped with variable crimp depths (i.e., distance crimp 200 is driven into embryonic lock 136). Increasing crimp depth increases the friction force between the filament 34 and the resulting lock 36 that must be overcome to move the components relative to one another. Thus, by gradually increasing the crimp depth during the crimping process, the friction force required to be overcome is also gradually increased, as may be seen by comparing FIG. 22A to FIG. 22B. As may be seen, the force gage 240 registers a higher force in FIG. 22B to move the two components relative to one another because the crimp 200 has been driven further into the embryonic lock 136. By testing/measuring the friction force as the crimp 200 is driven into the embryonic lock 136 (either continuously or in a crimp/test/crimp/test/regime) for various crimp depths and halting further crimping upon a determination that the friction force has fallen with in an acceptable range, a consistent requisite friction force may be established for each closure device 20, ensuring quality control if this method is executed for each closure device 20. This alleviates tolerancing issues because the testing is performed on each individual component.

Figure 23:
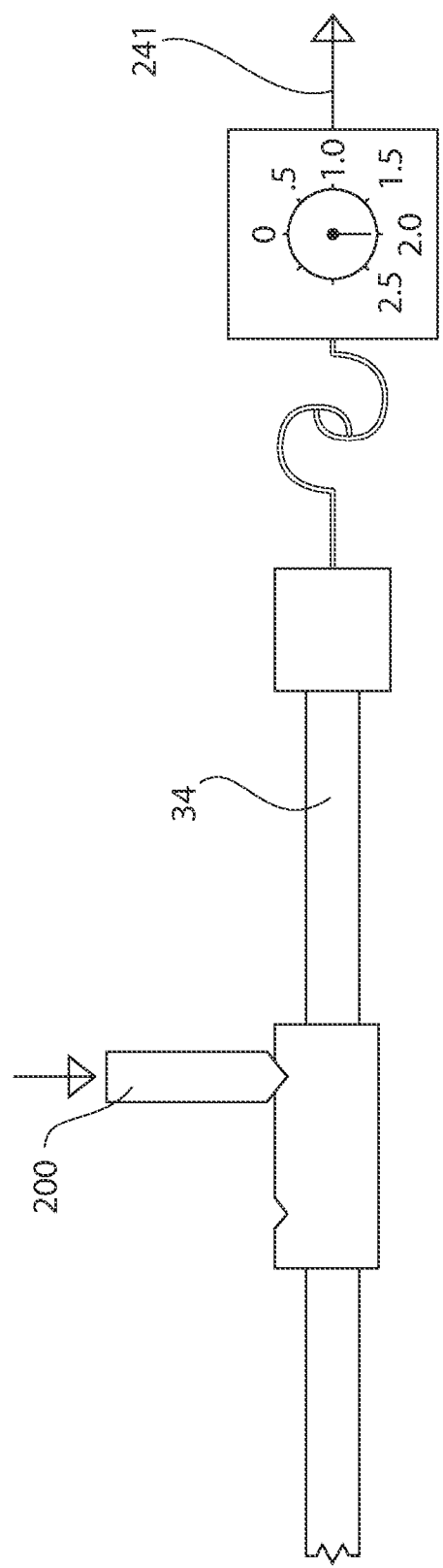
FIG. 23 depicts another exemplary embodiment in which the lock is crimped whereby the requisite friction force between the lock and the filament is controlled.

In an alternate method, instead of varying crimp depth as just detailed, additional crimps are added to the embryonic lock 136 to increase the friction force as may be seen by way of example in FIG. 23. Using a force gage 240, the friction force may be measured in the same way as detailed above. By testing/measuring the friction force as the crimp 200 is driven into the embryonic lock 136 at a new location and halting further crimping upon a determination that the friction force has fallen with in an acceptable range, a consistent requisite friction force may be established for each closure device 20, ensuring quality control if this method is executed for each closure device 20.

Figure 24B:
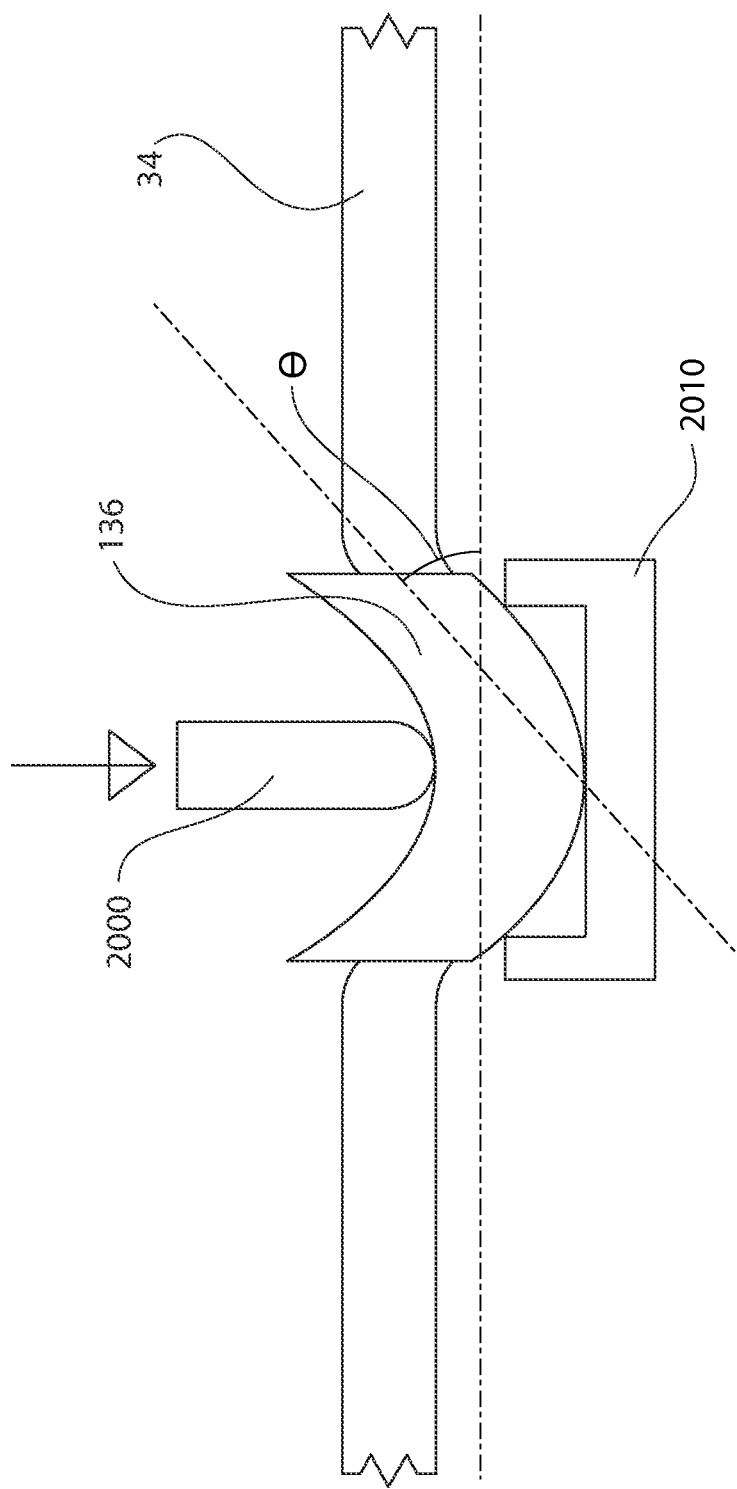
FIGS. 24A-25B depict another exemplary embodiment in which the lock is bent whereby the requisite friction force between the lock and the filament is controlled.
Figure 25A:
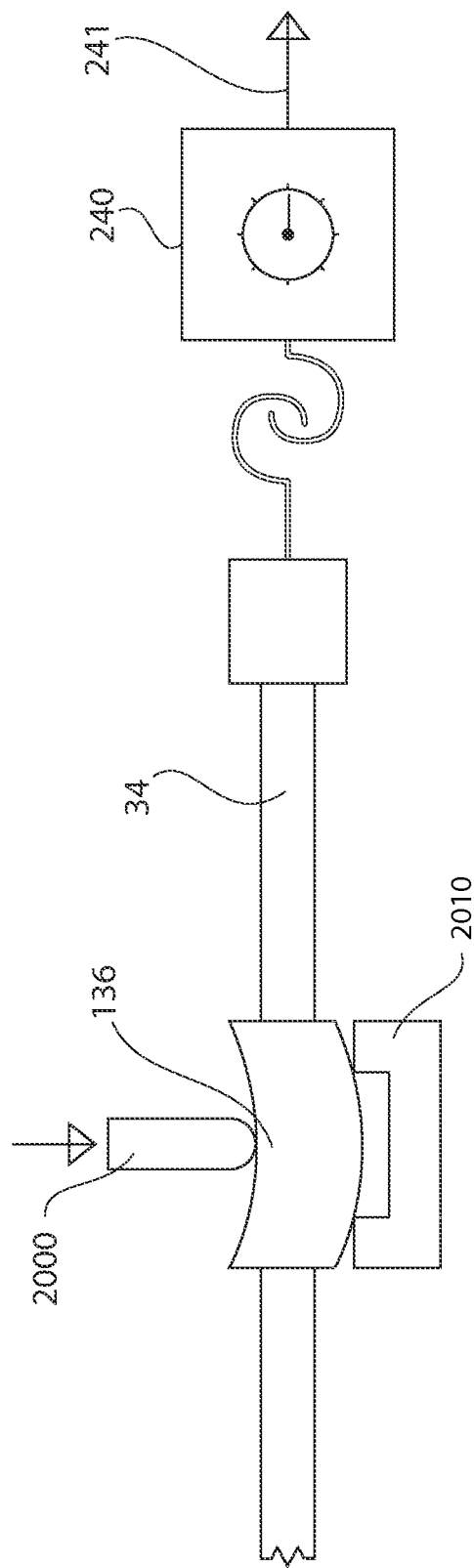
Figure 25B:
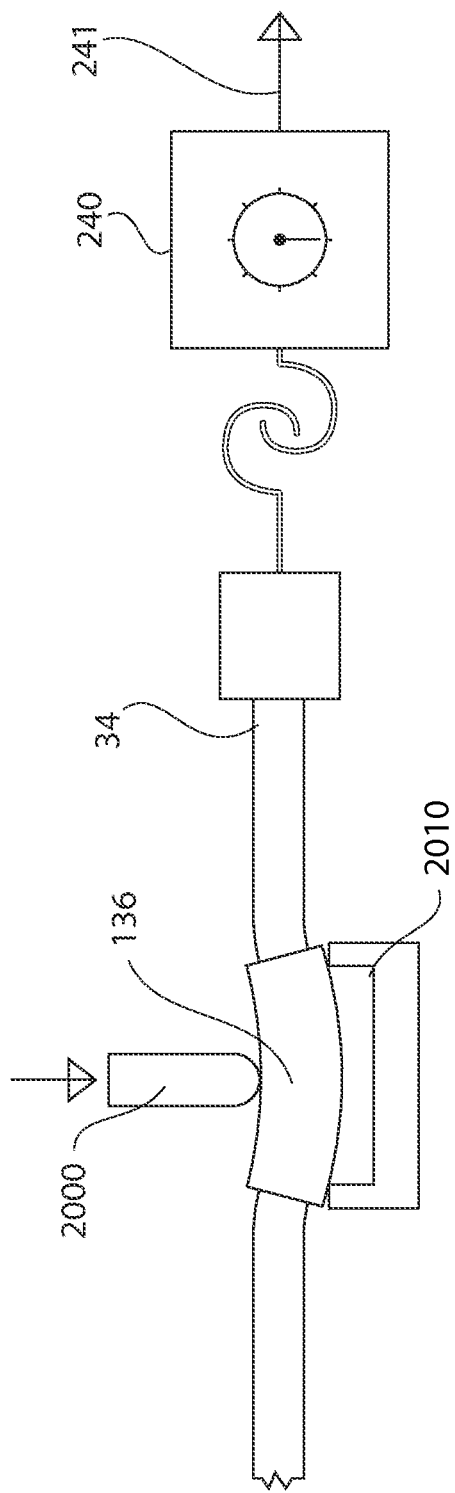

In yet another alternative embodiment, as depicted in FIGS. 24A and 24B, the embryonic lock 136 is bent to increase the friction force between the lock and the filament. FIG. 24A depicts a bending rack 2010 and a bending mandrel 2000. A downward force is applied on the bending mandrel 2000, which force is reacted against by the bending rack 2010, to bend the embryonic lock 136, as is depicted by way of example in FIG. 24B. As the angle θ of the bend increases (as seen by comparing FIG. 24A to FIG. 24B) the friction force between the lock and the filament also increases. In an exemplary method, the filament 34 is linked to a force gage as shown in FIG. 25A. A force is applied to the force gage 240 and thus the filament 34 in the direction of the horizontal arrow 241 while the embryonic lock 136 is crimped to produce a varying bend angle θ. Increasing the bend angle θ increases the friction force that must be overcome to move filament 34 relative to the resulting lock 36. Thus, by gradually increasing the bend angle θ during the bending process, the requisite friction force is also gradually increased, as may be seen by comparing FIG. 25A to FIG. 25B. As may be seen, the force gage 240 registers a higher force in FIG. 25B because the embryonic lock 136 has been bent more. By testing/measuring the friction force as the embryonic lock 136 is bent (either continuously or in a bend/test/bend/test regime) for various bend angles and halting further bending upon a determination that the requisite friction force has fallen with in an acceptable range, a consistent friction force may be created for each closure device 20, ensuring quality control if this method is executed for each closure device 20. This alleviates tolerancing issues because the testing is performed on each individual component.

Figure 26A:
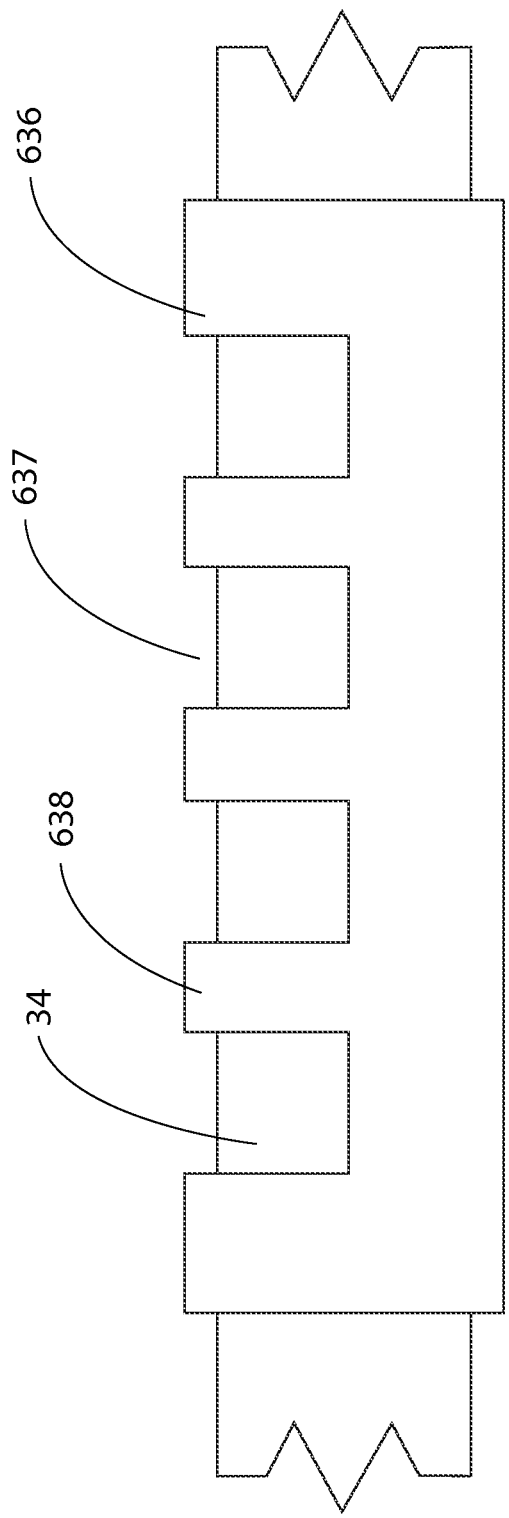
FIGS. 26A-27B depict another exemplary embodiment in which the lock is deformed whereby the requisite friction force between the lock and the filament is controlled.
Figure 26B:
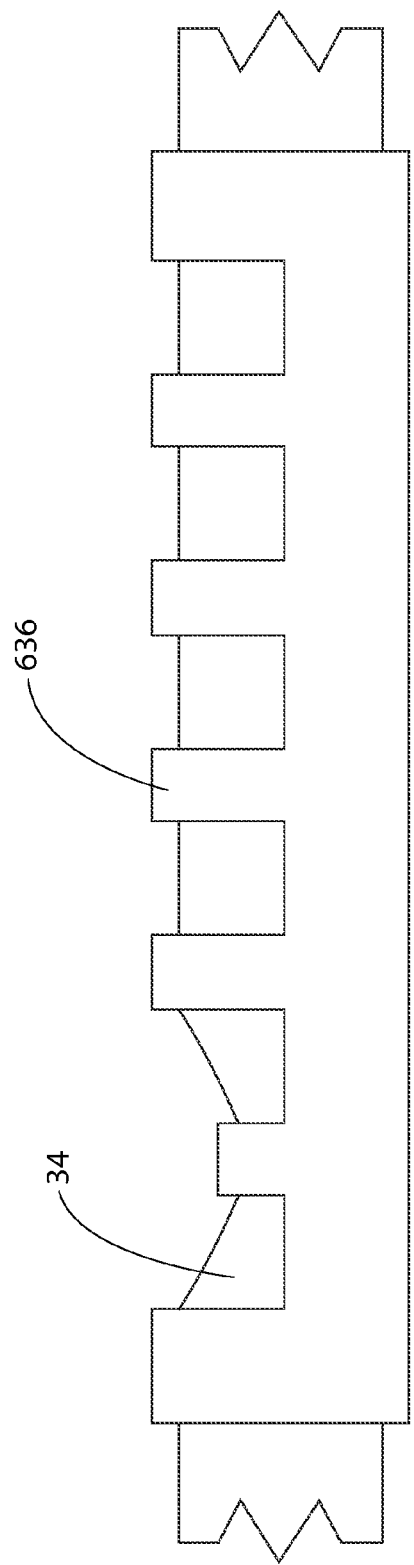
Figure 26C:
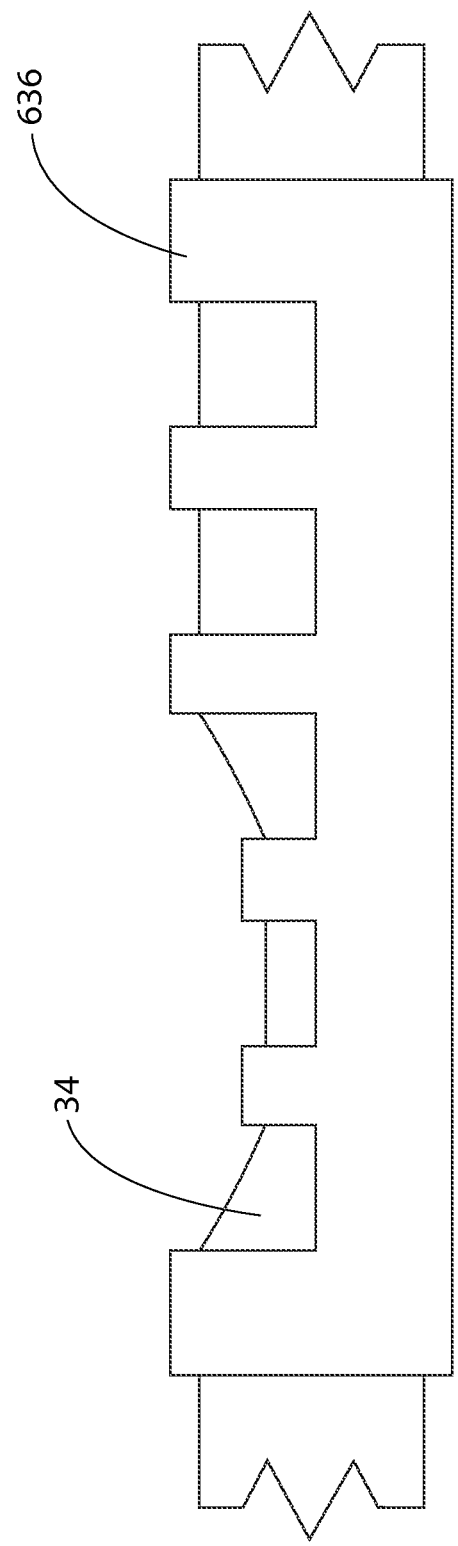
Figure 27A:
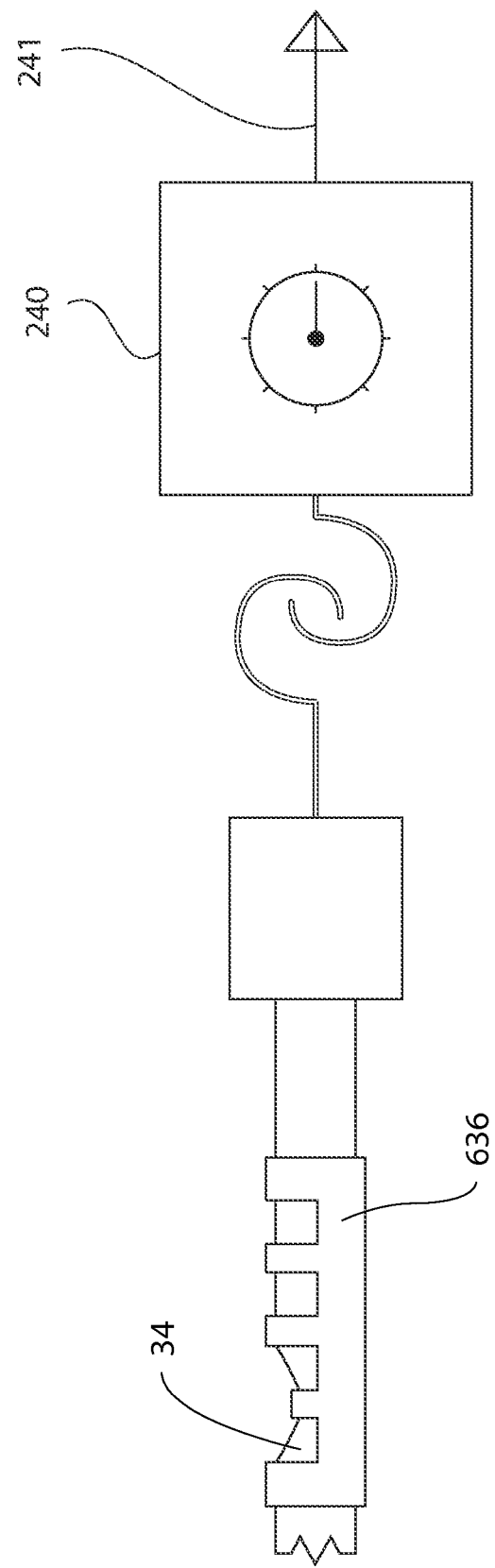
Figure 27B:
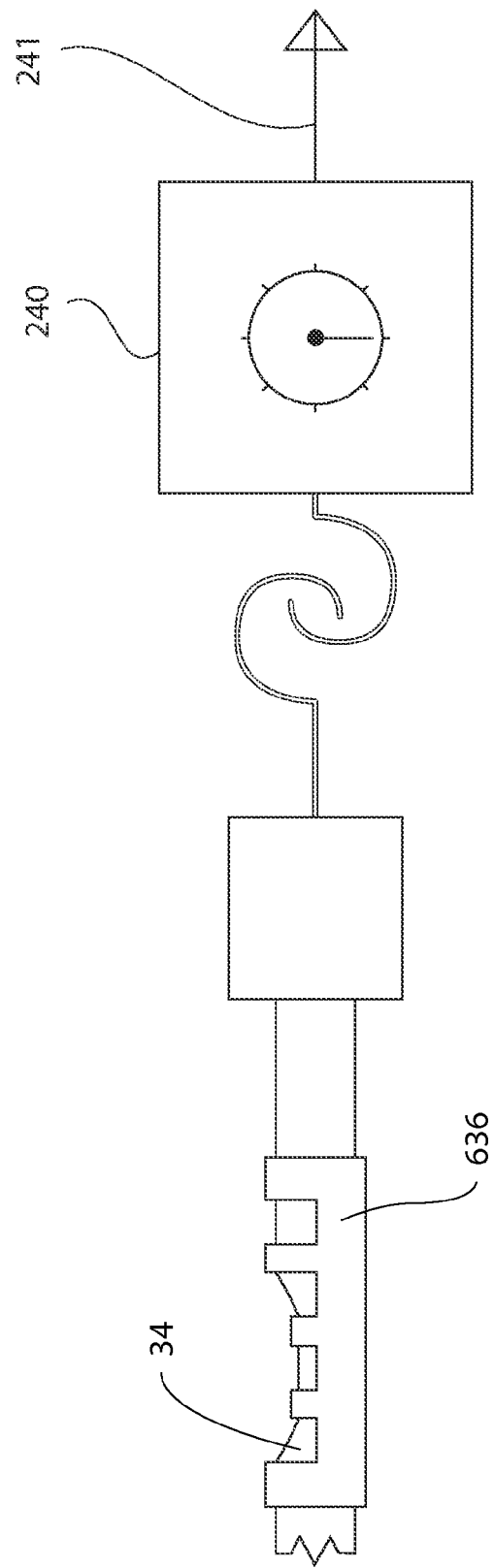

In a variation of a crimping method includes crimping discrete, preprepared portions of an embryonic lock so that the resulting friction force upon movement of the resulting lock and the filament may be controlled. In an exemplary method, an embryonic lock 636 is prepared with slots 637 cut into the embryonic lock 636 as is exemplary depicted in FIG. 26A. Then, one or more of the resulting arches 638 is crimped or otherwise compressed, one, two, three, four, etc., at a time. For example, in a method that includes crimping/compressing one arch at a time, after a first crimping/compressing operation, the embryonic lock 636 takes on the form as shown in FIG. 26B. Next, a second arch is crimped/compressed, resulting in an embryonic lock 636 taking on the form as shown in FIG. 26C. As each arch 638 is crimped or compressed, the friction force between the resulting lock and the filament 34 is increased. As with some other embodiments detailed herein, the filament 34 is linked to a force gage as shown in FIG. 27A. A force is applied to the force gage 240 and thus the filament 34 in the direction of the horizontal arrow while the arches of the embryonic lock 636 are compressed. Increasing the number of arches crimped/compressed increases the friction force between the filament 34 and the resulting lock. Thus, by gradually increasing the number of arches crimped/compressed, the friction force is also gradually increased, as may be seen by comparing FIG. 27A to FIG. 27B. As may be seen, the force gage 240 registers a higher force in FIG. 27B because more arches have been crimped/compressed in the embryonic lock 636. By testing/measuring the friction force as the arches are compressed (either continuously or in a compress/test/compress/test regime) for various arch compressions and halting further crimping upon a determination that the friction force has fallen with in an acceptable range, a consistent requisite friction force may be created for each closure device 20, ensuring quality control if this method is executed for each closure device 20. This alleviates tolerancing issues because the testing is performed on each individual component. It is noted in other embodiments, the depth of crimping/compression of the arches may be controlled. By measuring the resulting force for various depths in an analogous manner as detailed above with respect to FIGS. 22A and 22B, quality control can be further enhanced.

Figure 28:
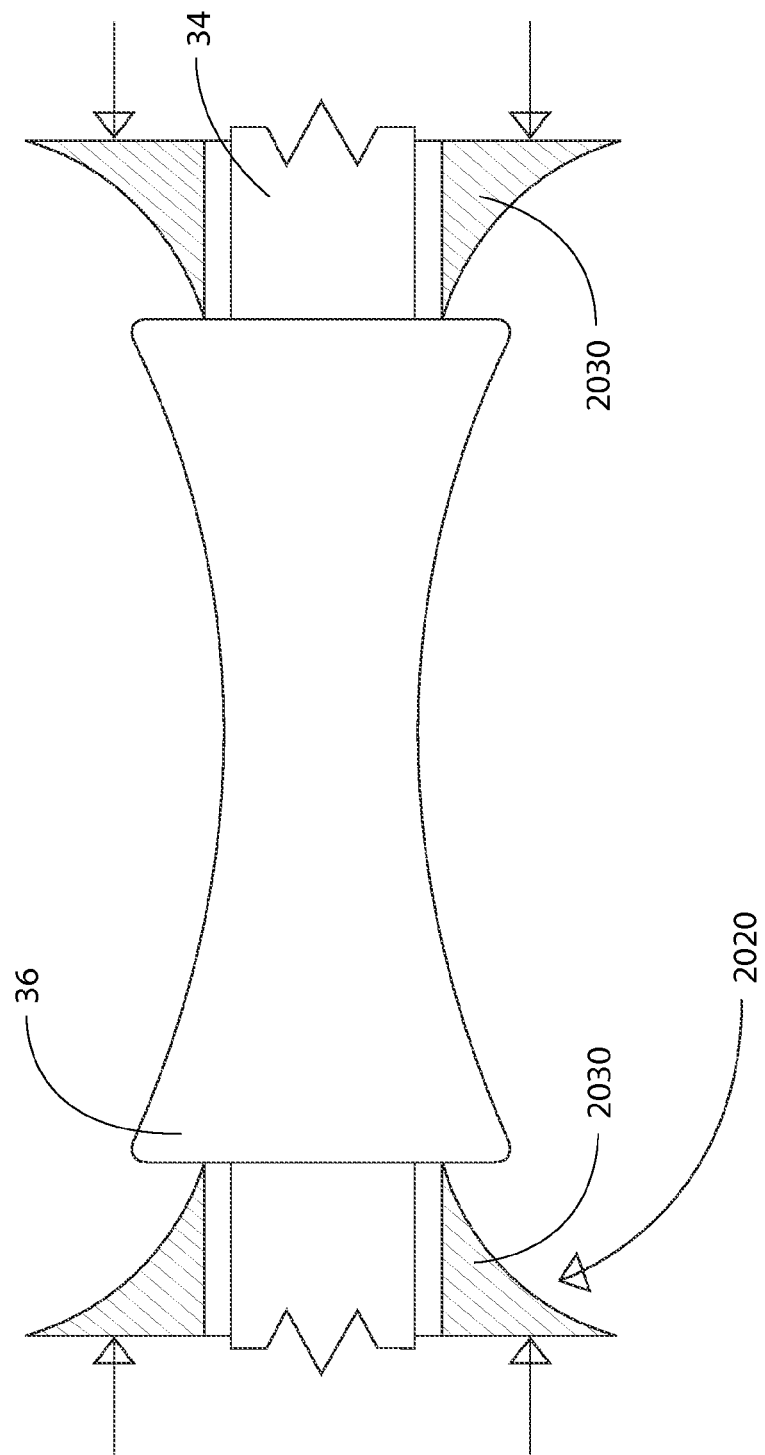
FIGS. 28-29B depict another exemplary embodiment in which the lock is deformed whereby the requisite friction force between the lock and the filament is controlled.
Figure 29A:
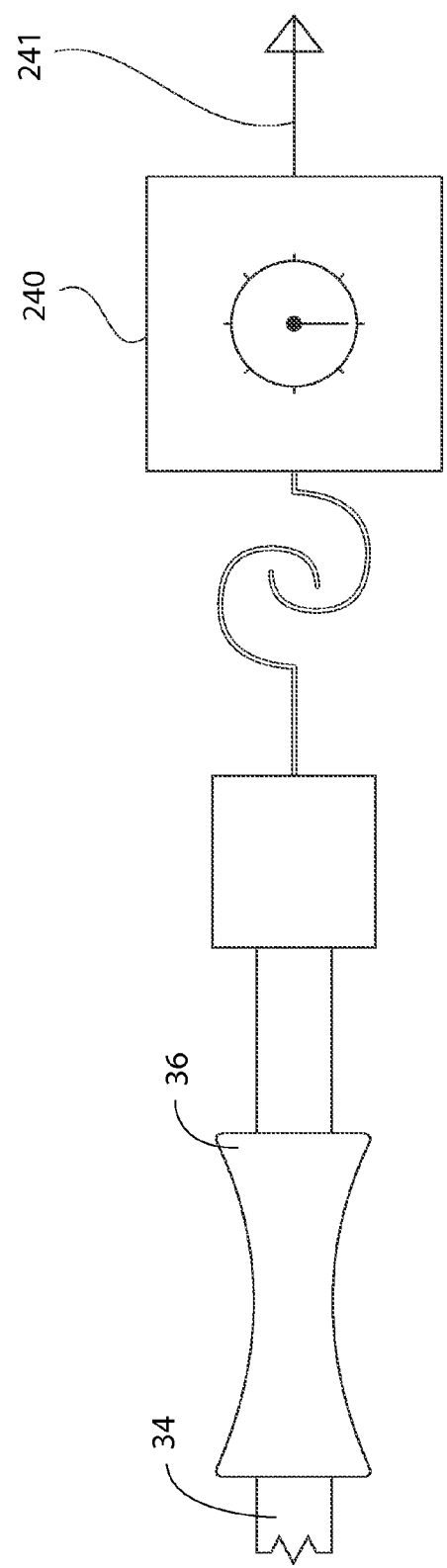
Figure 29B:
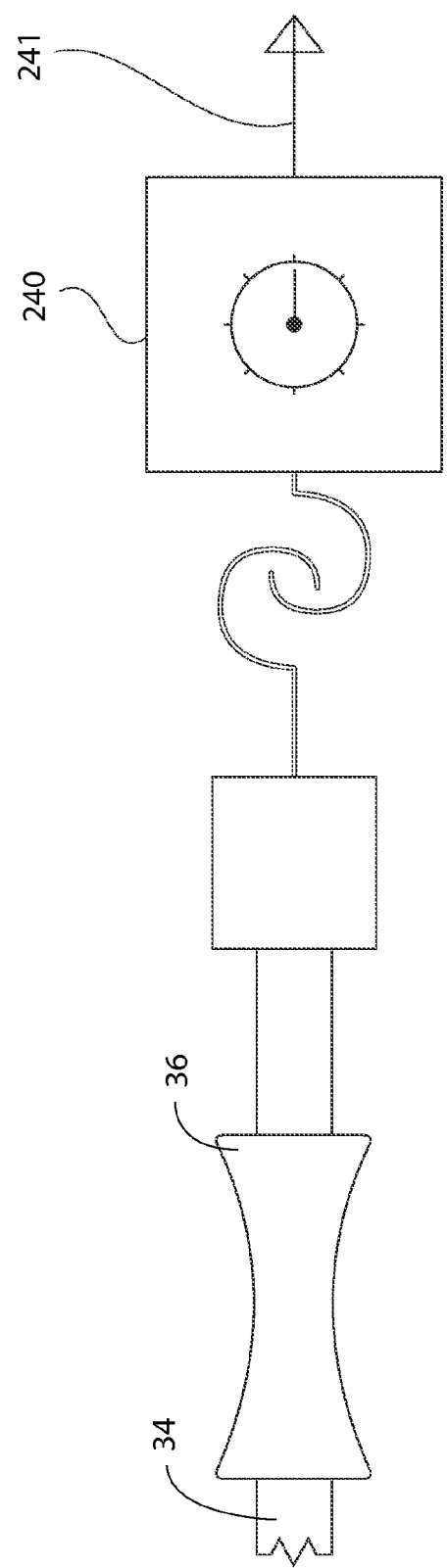

Another embodiment of the present invention includes a method and a device for unduing a crimping operation. As may be seen in FIG. 28, a decrimping device 2020 includes jaws 2030 that fit around filament 34. The jaws are driven towards each other (or in embodiments where jaws 2030 are only located on one side of the lock 36, the jaws 2030 are driven towards a reaction plate or the like. The jaws decrimp, at least partially, the crimp applied to the lock 36. This has the effect of reducing the friction force that must be overcome to move the lock 36 relative to the filament 34 as the crimp on the lock 36 is undone. In an exemplary method, the filament 34 is linked to a force gage as shown in FIG. 29A during the decrimping operation. A force is applied to the force gage 240 and thus the filament 34 in the direction of the horizontal arrow while the lock 36 is decrimped with variable decrimping (i.e., the amount that the jaws 2030 are driven towards each other is varied). Increasing the amount that the jaws 2030 are driven towards each other increases the bore diameter of the lock 36 and thus decreases the friction force required to be overcome to move the filament 34 relative to the resulting lock 36. Thus, by gradually increasing the depth that the jaws 2030 are inserted during the decrimping process the friction force is also gradually decreased, as may be seen by comparing FIG. 29A to FIG. 29B. As may be seen, the force gage 240 registers a lower force in FIG. 29B because the jaws 2030 have been driven further towards each other than in FIG. 29A, thereby increasing the bore diameter of the lock 36 relative to that of FIG. 29A. By testing/measuring the friction force as the jaws 2030 are driven towards each other (either continuously or in a decrimp/test/decrimp/test regime) for various depths and halting further driving upon a determination that the friction force has fallen with in an acceptable range, a consistent requisite friction force may be created for each closure device 20, ensuring quality control if this method is executed for each closure device 20. This alleviates tolerancing issues because the testing is performed on each individual component.

It is noted that the method just described may be used to rehabilitate a lock that was crimped too much (i.e., bring it back into specifications) and/or as a standard part of the process of manufacturing the closure device 20. That is, it could be standard procedure to "over crimp" the lock 36 and then decrimp the lock so that the friction force falls within the desired range. It is further noted that the decrimping device 2020 may be combined with the crimping device detailed above with respect to FIG. 22 for manufacturing efficiency purposes.

Figure 30B:
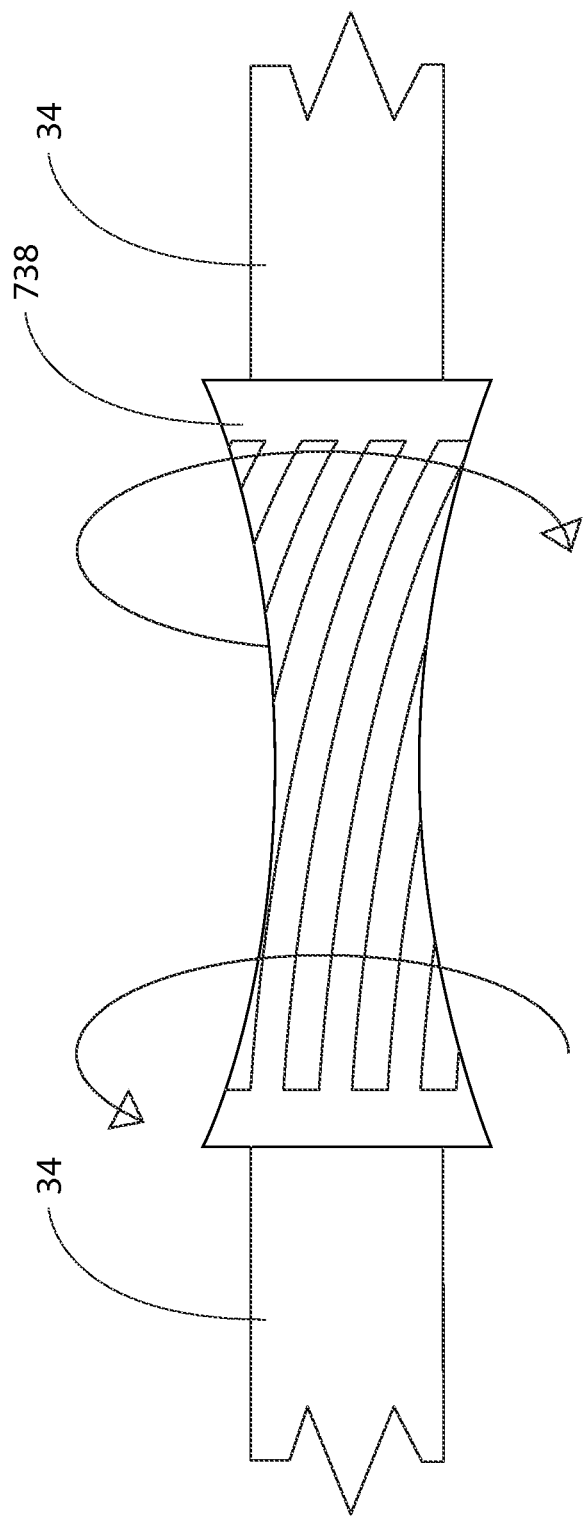

An alternate embodiment includes twisting an embryonic lock to reduce the interior bore diameter so that the resulting friction force required to be overcome to move the resulting lock relative to the filament may be controllably increased. In an exemplary method, an embryonic lock 736 is prepared with slots 737 cut into the embryonic lock 736 as is exemplary depicted in FIG. 30A. Then, the embryonic lock 736 is twisted to reduce the interior diameter, thereby compressing the filament 34, as may be seen in FIG. 30B. As with some other embodiments detailed herein, the filament 34 may be linked to a force gage. A force is applied to the force gage as detailed herein while the embryonic lock 736 is twisted. Increasing the twist angle of the embryonic lock 736 increases the friction force between the filament 34 and the resulting lock. Thus, by gradually increasing the twist angle, the friction force is also gradually increased. As will be understood, the force gage will register a higher force the more that the embryonic lock 736 is twisted. By testing/measuring the friction force as the embryonic lock 736 is twisted (either continuously or in a twist/test/twist/test regime) and halting further twisting upon a determination that the friction force has fallen with in an acceptable range, a consistent requisite friction force may be created for each closure device 20, ensuring quality control if this method is executed for each closure device 20. This alleviates tolerancing issues because the testing is performed on each individual component. It is noted in other embodiments, the embryonic lock 736 may be over twisted and then dewisted to arrive at the desired friction force. Thus, this embodiment is analogous to that detailed above with respect to the decrimping device. It is noted that in some embodiments, the embryonic lock 736 will be twisted 20 degrees, then the friction force will be tested, followed by an another 20 degrees of twisting, etc. This process will be repeated until the friction force that must be overcome to move the components relative to one another falls within a range of about 0.4 to 0.6 pounds.

In an embodiment, the lock 736 may be twisted such that the interior diameter of the lock 736 is reduced from 0.015 inches to 0.013 inches to result in one pound of force being required to overcome the friction force between the filament and the lock. Further, the interior diameter of the lock 736 may be reduced to 0.012 inches to result in five pounds of force being required to overcome the friction force between the filament and the lock.

Figure 31A:
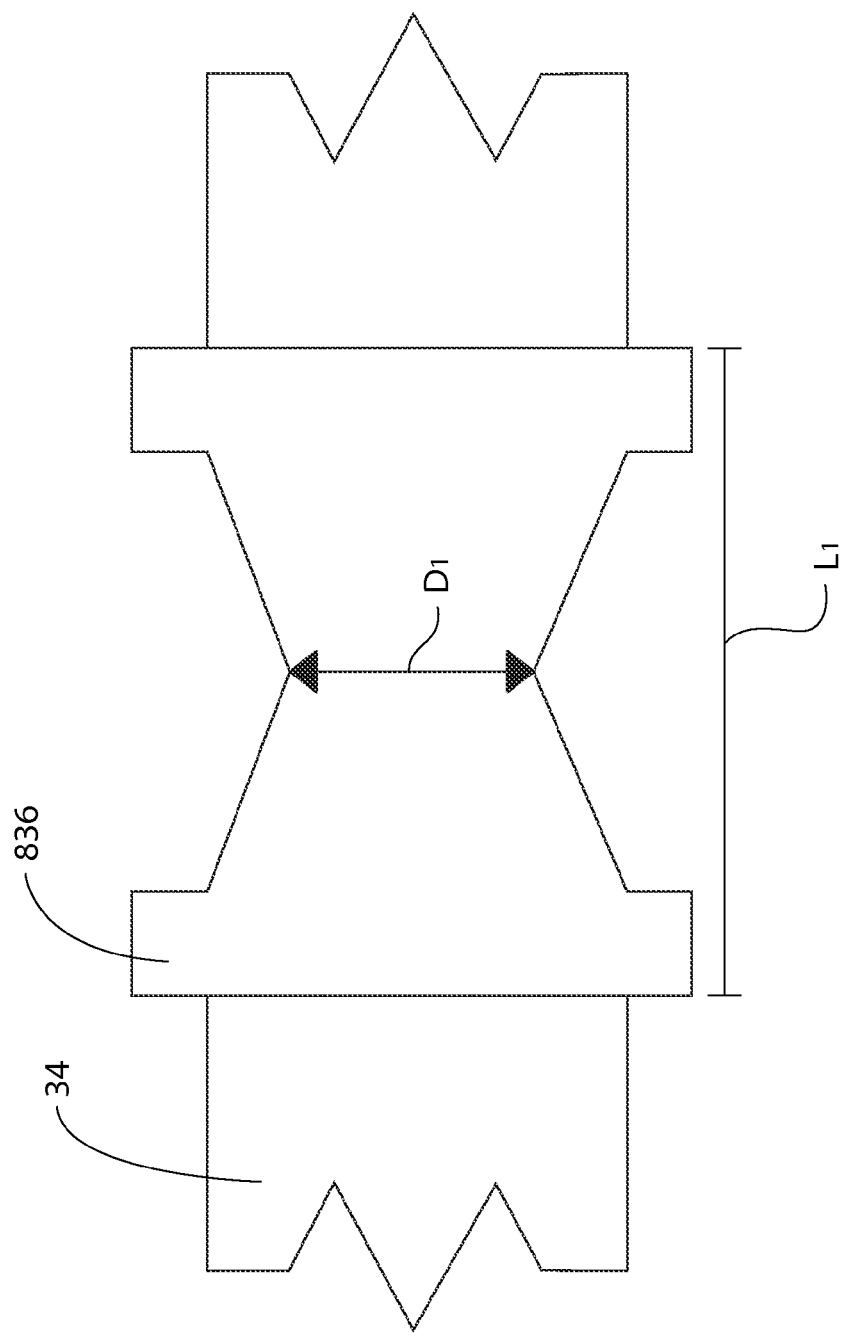
FIGS. 31A-31B depict another exemplary embodiment in which the lock is compressed whereby the requisite friction force between the lock and the filament is controlled.
Figure 31B:
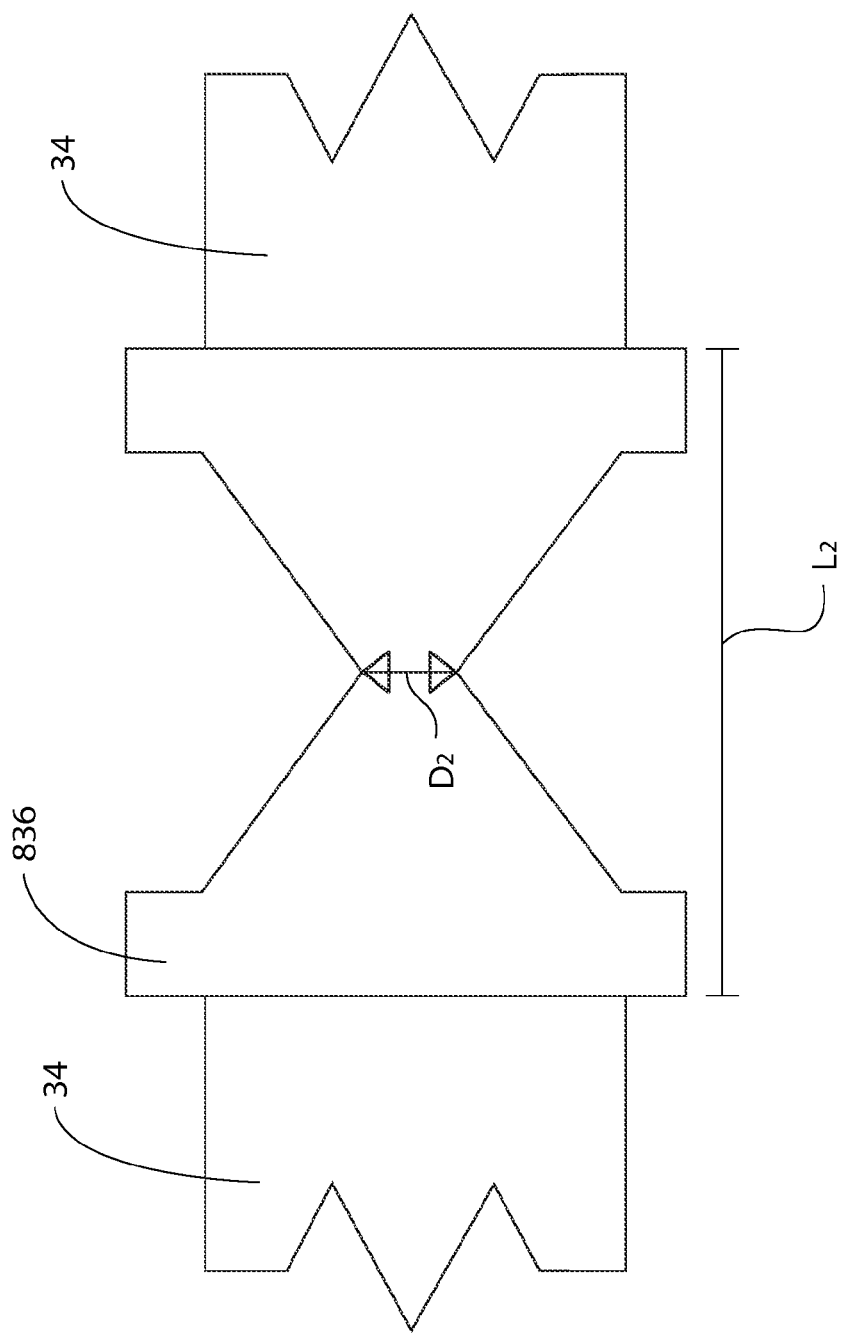

Yet another alternate embodiment includes compressing an embryonic lock in the longitudinal direction to reduce the interior bore diameter so that the resulting friction force upon movement of the resulting lock and the filament may controllably increased. In an exemplary method, an embryonic lock 836 as may be seen in FIGS. 31A and 31B having a configuration that lends itself to relatively easy longitudinal compression coupled with a corresponding reduction in the interior diameter of the bore is compressed from a length $L_1$ (where the embryonic lock 836 has an interior bore diameter of $D_1$) ultimately to a length $L_2$, which is less than $L_1$ (where the embryonic lock 836 has an interior bore diameter of $D_2$, which is less than $D_1$). As with some other embodiments detailed herein, the filament 34 may be linked to a force gage. A force is applied to the force gage as detailed herein while the embryonic lock 836 is compressed. Increasing the compression of the embryonic lock 836 increases the friction force between the filament 34 and the resulting lock because the interior bore diameter is reduced. Thus, by gradually compressing the embryonic lock, the friction force is also gradually increased. As will be understood, the force gage will register a higher force the more that the embryonic lock 836 is compressed. By testing/measuring the friction force as the embryonic lock 836 is compressed (either continuously or in a compress/test/compress/test regime) and halting further compression upon a determination that the friction force has fallen with in an acceptable range, a consistent requisite friction force may be created for each closure device 20, ensuring quality control if this method is executed for each closure device 20. This alleviates tolerancing issues because the testing is performed on each individual component. It is noted in other embodiments, the embryonic lock 836 may be over compressed and then decompressed to arrive at the desired friction force. Thus, this embodiment is analogous to that detailed above with respect to the decrimping device.

It is noted that in some embodiments, the locks disclosed herein may be made of titanium or a titanium alloy, iron or an iron alloy (e.g., an iron-magnesium alloy), stainless steel 302, 307, 316 and 316L or other types of stainless steel, a cobalt chromium alloy, PLLA/PLG, or any other material that provides acceptable results when configured as a lock as detailed herein.

Figure 32A:
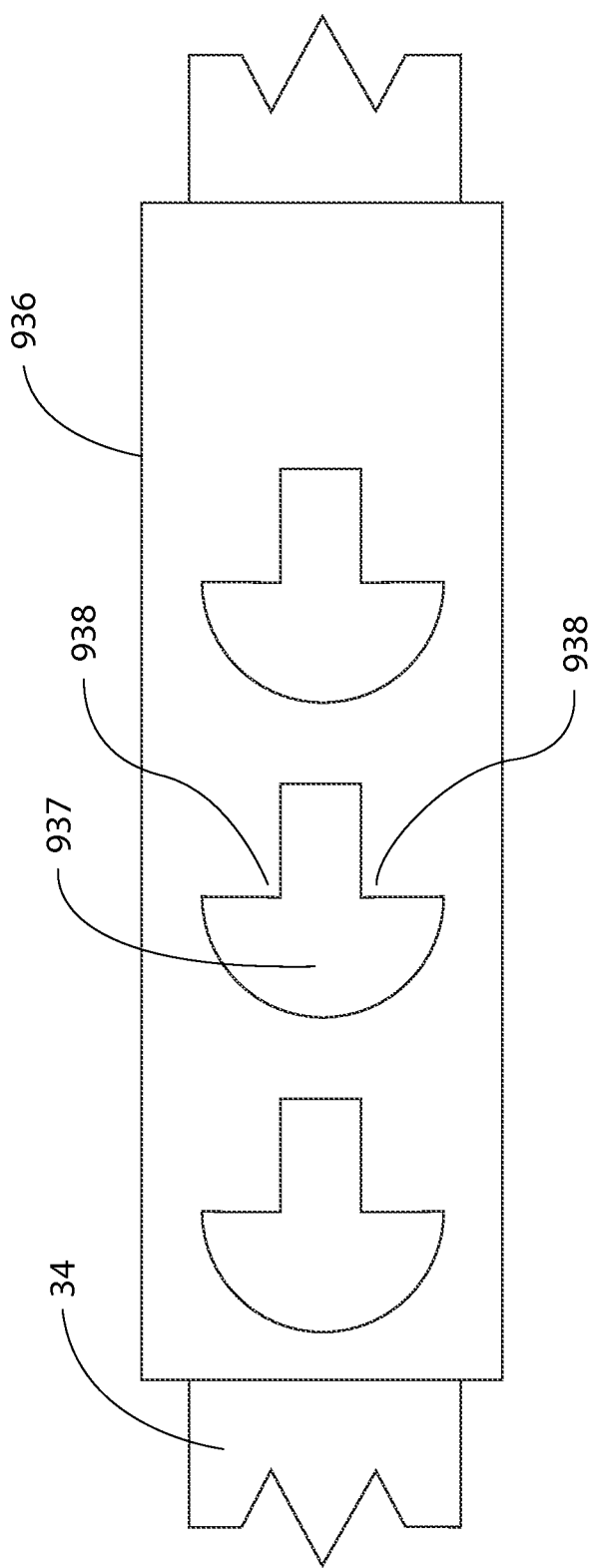
FIGS. 32A-33 depict another exemplary embodiment in which the lock is deformed whereby the requisite friction force between the lock and the filament is controlled.
Figure 32B:
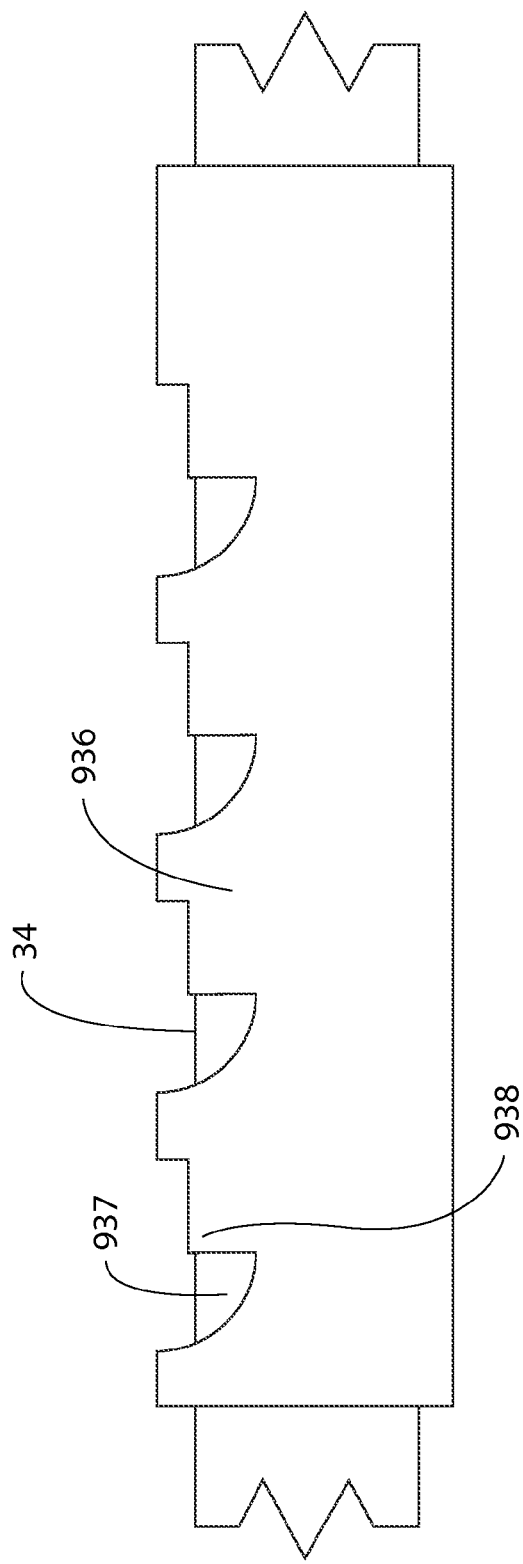
Figure 33:
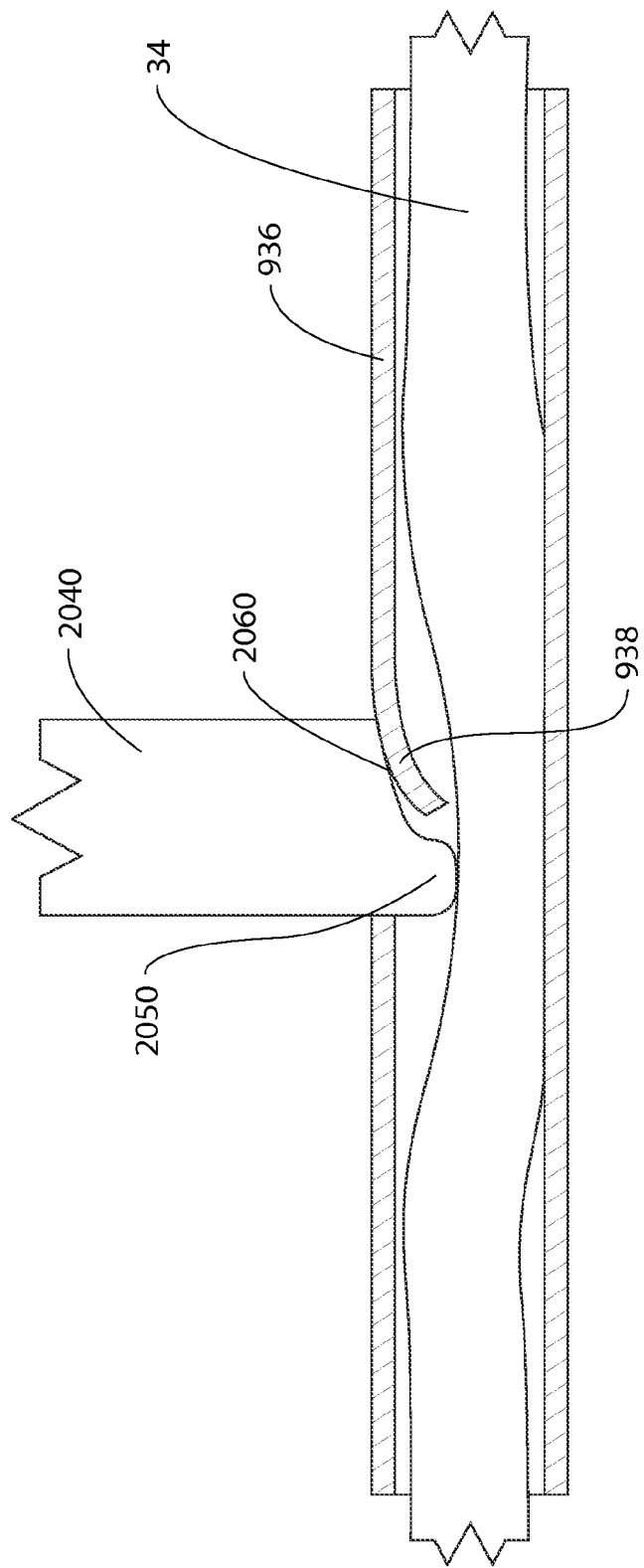

Another variation of a crimping method includes crimping discrete, preprepared portions of an embryonic lock so that the resulting friction force required to move the resulting lock relative to the filament may be controlled. In an exemplary method, an embryonic lock 936 is prepared with holes 937 cut (e.g., laser cut) into the embryonic lock 936 as is exemplary depicted in FIGS. 32A and 32B (FIG. 32B being a side-view of FIG. 32A). Then, the corners 938 of one or more of the resulting holes 937 are crimped or otherwise compressed, one, two, three, four, etc., at a time using a crimping mandrel 2040 as seen in FIG. 33. FIG. 33 depicts a crimping mandrel 2040 including a head 2050 and a wedge 2060. The lateral dimensions of the crimping mandrel 2040 are configured such that the area around the head 2050 slidably fits into the hole 937 such that the hole 937 aligns the crimping mandrel 2040 (more particularly, the semi-circle section aligns the crimping mandrel 2040). Driving the crimping mandrel 2040 into the hole 937 causes the wedge 2060 to crimp down the corners 938 as may be seen in FIG. 33.

In a method that includes crimping/compressing the corners 938 of one hole 936 one at a time, after a first set of corners 938 are crimped, if necessary a second set of corners are crimped, followed by a third, etc., as necessary. As each set of corners 938 is crimped, the requisite friction force required to be overcome to move the resulting lock relative to the filament 34 is increased. As with some other embodiments detailed herein, the filament 34 is linked to a force gage. A force is applied to the force gage 240 and thus the filament 34 while the sets of corners of the embryonic lock 636 are crimped. Increasing the number of corners crimped increases the friction force between the filament 34 and the resulting lock. Thus, by gradually increasing the number of corners compressed, the friction force is also gradually increased. By testing/measuring the friction force as the corners are crimped (either continuously or in a crimp/test/crimp/test regime) for various crimping actions and halting further crimping upon a determination that the friction force has fallen with in an acceptable range, a consistent friction force may be created for each closure device 20, ensuring quality control if this method is executed for each closure device 20. This alleviates tolerancing issues because the testing is performed on each individual component.

Further, an embodiment of the method just detailed includes fully bottoming out the head 2050 of the crimping mandrel 2040 on the filament 34 (i.e., driving the crimping mandrel 2040 downward onto the filament 34 until the filament 34 is substantially fully compressed) during each crimping action. By properly dimensioning the crimping mandrel 2040, tolerancing of the filament and/or the embryonic lock can be discounted, at least with respect to a braded filament 34. That is, if the head 2050 substantially fully compresses the filament, the amount that the corners 938 will be crimped relative to the filament will correspond to a sufficient amount of crimping of the corners to establish a requisite friction force for each individual closure device without testing. That is, in some exemplary embodiments, by bottoming out the head of the crimping mandrel 2040, the depth of crimping is controlled because the amount that the filament 34 can be ultimately compressed relative to the crimping should be about the same regardless of tolerancing of the filament 34 and/or the embryonic lock. Also, in some embodiments, the "D" shape allow the head to have sufficient strength and, as noted above, permits guiding/alignment of the crimping mandrel 2040 with the embryonic lock 936. In some exemplary embodiments using such a method, the crimping mandrel 2040 can be calibrated to establish various requisite friction forces by varying the head to wedge distance and/or varying the angle of the wedge of the mandrel 2040.

It is noted in other embodiments, the depth of crimping of the corners may be controlled. By measuring the resulting force for various depths in an analogous manner as detailed above with respect to FIGS. 22A and 22B, quality control can be further enhanced.

Figure 34:
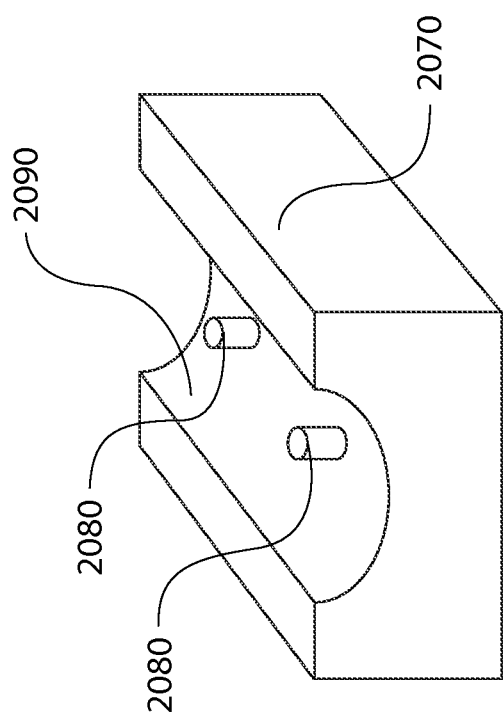
FIG. 34 depict a fixture used during crimping of some exemplary locks.
Figure 35:
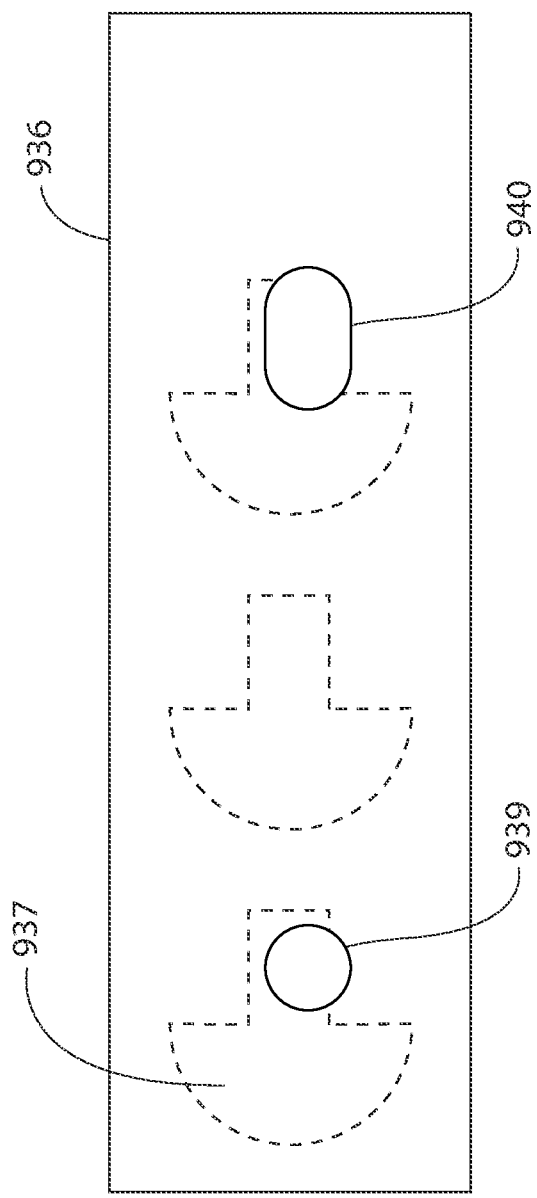
FIG. 35 depicts a lock that interfaces with the fixture of FIG. 34.

FIG. 34 depicts a holding fixture 2070 that may be used to hold the embryonic lock 936 in place during crimping. However, in other embodiments, the fixture 207 may be used with other embryonic locks. As may be seen in FIG. 34, the fixture 2070 includes two studs 2080 that protrude from the curved surface 2090 of the fixture 2070. These studs 2080 fit into corresponding holes in the embryonic lock 936 (or other embryonic lock as detailed herein and variations thereof) as depicted in FIG. 35. Specifically, opposite the holes 937, holes 939 and 940 are positioned in the embryonic lock 936. Hole 939 is a circular hole while hole 940 is a slotted hole to relieve the tolerancing in the longitudinal direction. Any size and/or shape hole may be used providing that the embryonic lock 936 is held in place. Alternatively, the holes in the embryonic lock 936 may be circular and one of the studs 2080 may be a square or rectangle pin or the like.

Figure 36:
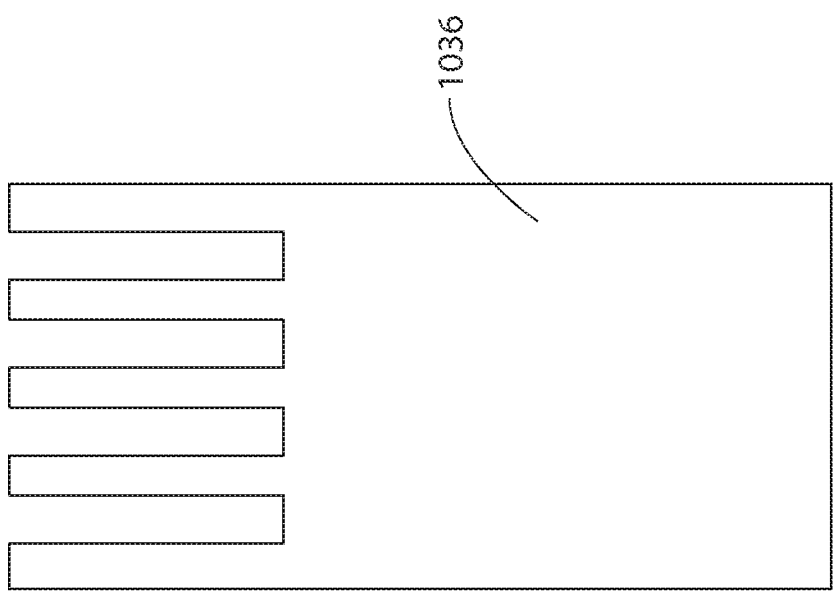
FIG. 36-37 depict alternate embodiments of a lock.

With respect to the embodiment depicted above with respect to FIG. 16A, it is noted that the end portions of the embryonic lock 3360 need not be pointed. That is, in some embodiments, the ends may be blunt (flat). Along these lines, FIG. 36 depicts an alternate embodiment of an embryonic lock 1036. Embryonic lock 1036 may be substituted for embryonic lock 3360 referenced herein in FIGS. 16A and 16B and 16C.

Figure 37:
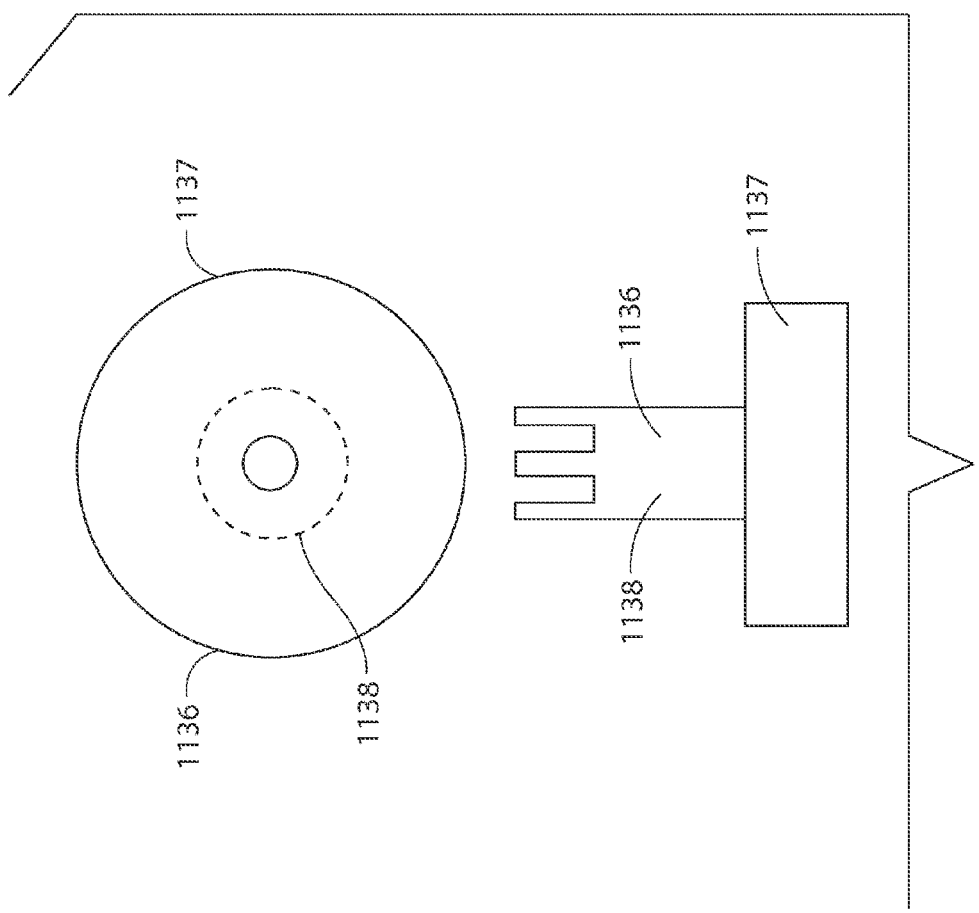
Figure 38:
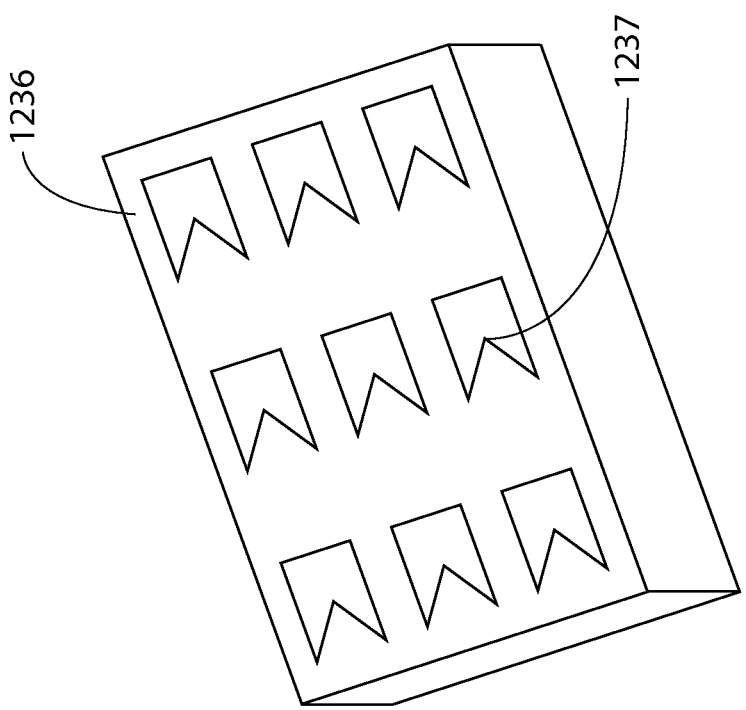
FIGS. 38-42 depict exemplary embodiments of embryonic locks.

FIG. 37 depicts an alternate embodiment of an embryonic lock 1136 with a protruding side 1137. In an exemplary embodiment, the protruding side 1137 is in the form of a cylinder that extends from the main body 1138 of the embryonic lock 1136.

FIGs. 38-42 depict an alternate embryonic lock that may be used in some embodiments of the present invention. As may be seen from these figures, initially, the embryonic lock 1236 is in the form of a rectangular plate including pointed tabs 1237 etched therein. In other embodiments, the pointed tabs 1237 may be stamped therein or the embryonic lock 1236 may be formed through lithography to include the pointed taps 1237. The embryonic lock 1236 depicted in FIG. 38. may be 2 mm by 2 mm square.

Figure 39:
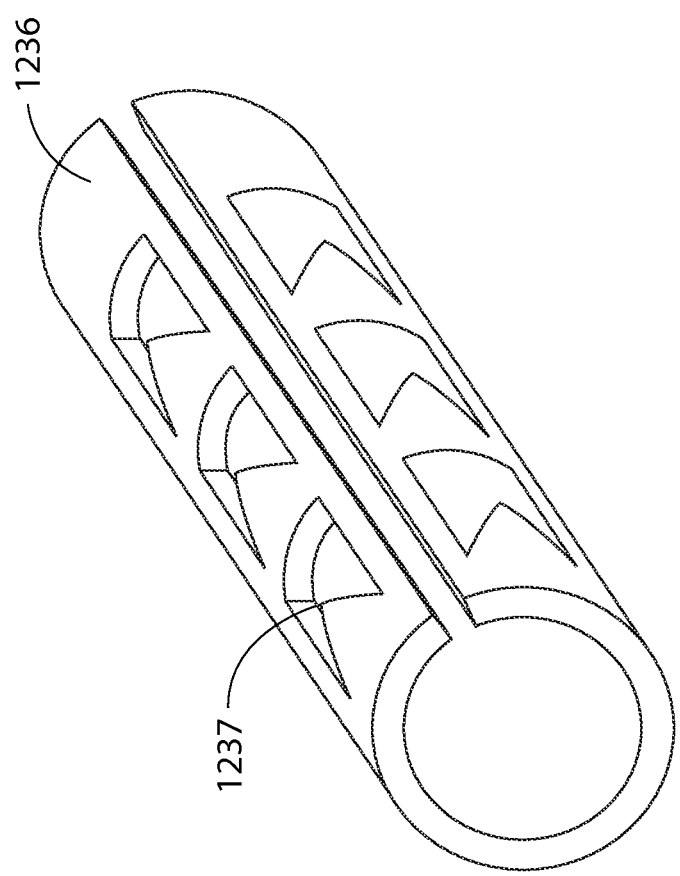
Figure 40:
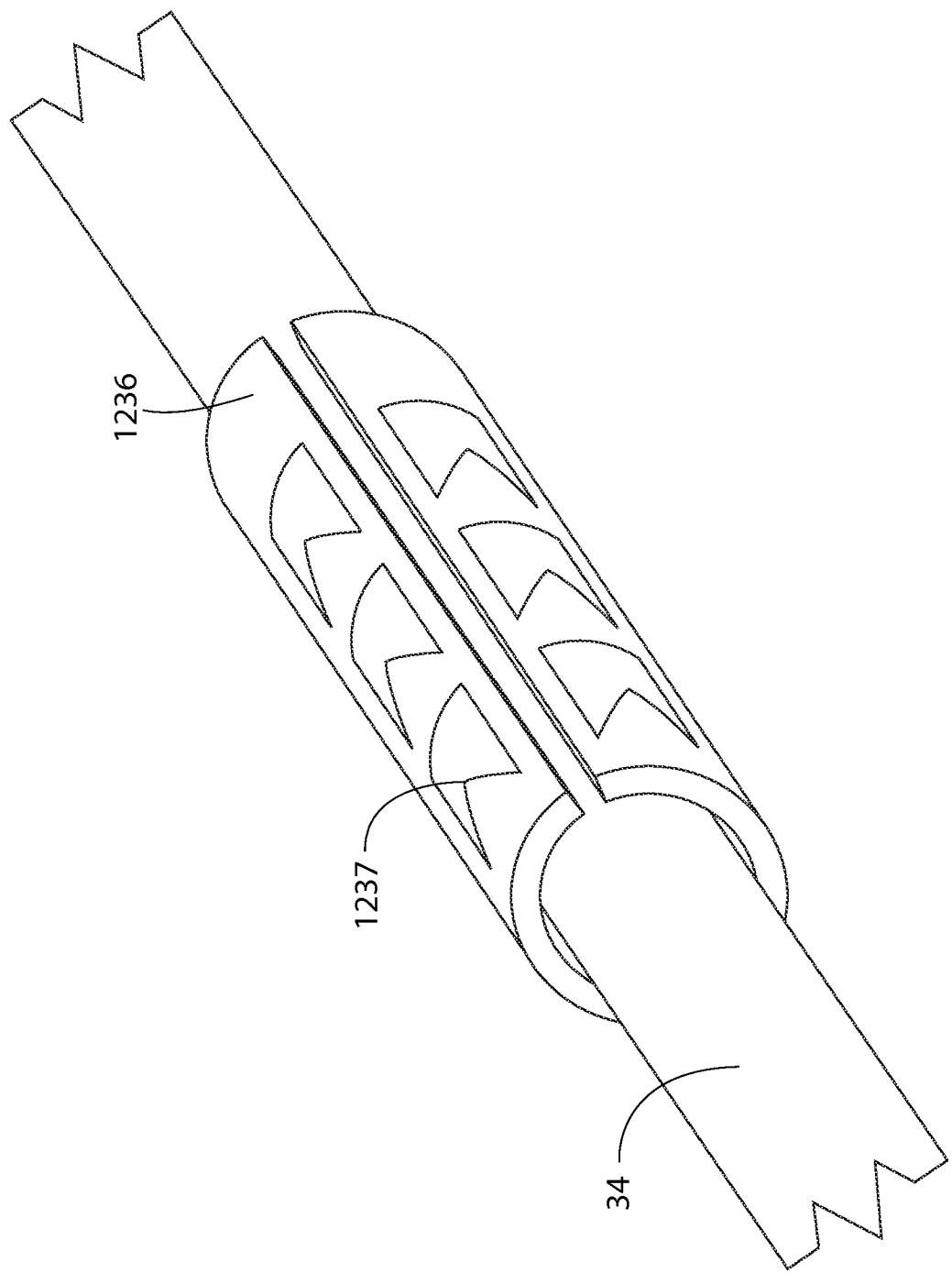
Figure 41:
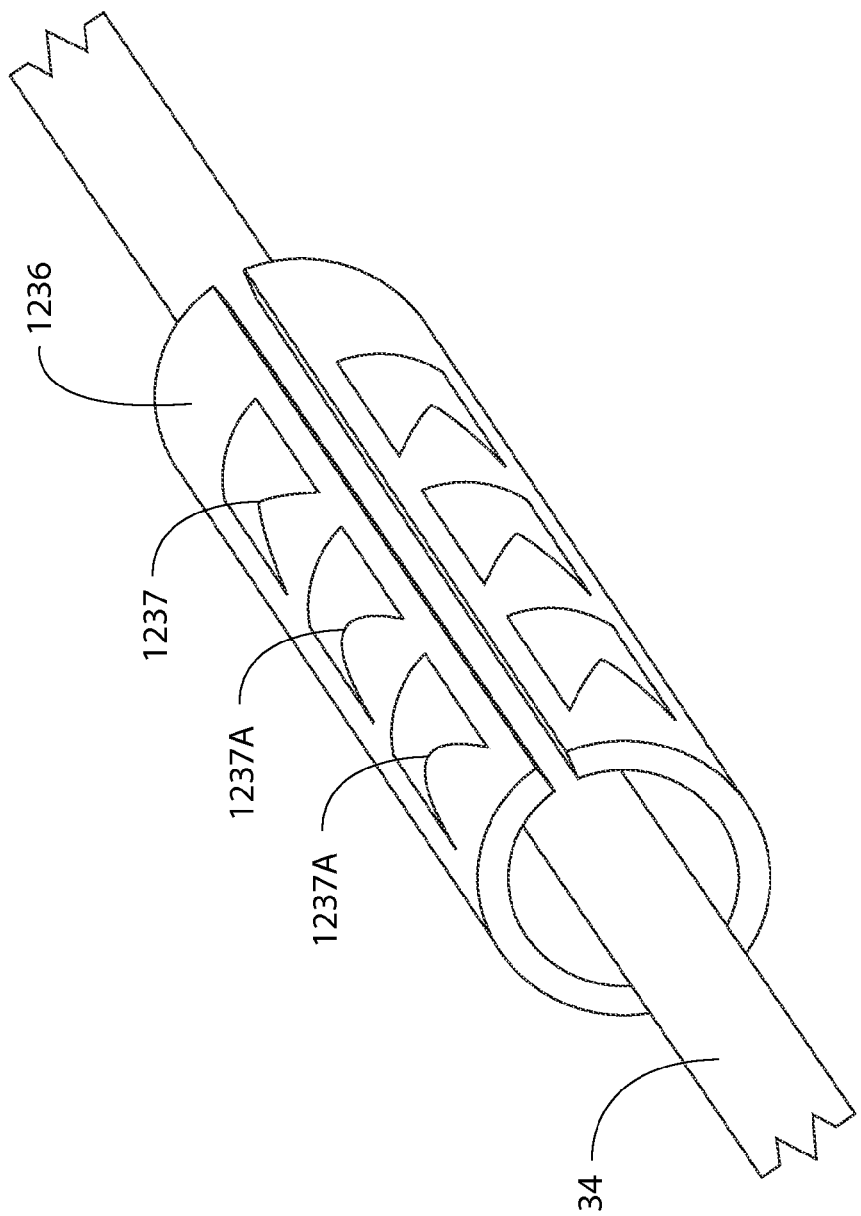
Figure 42:
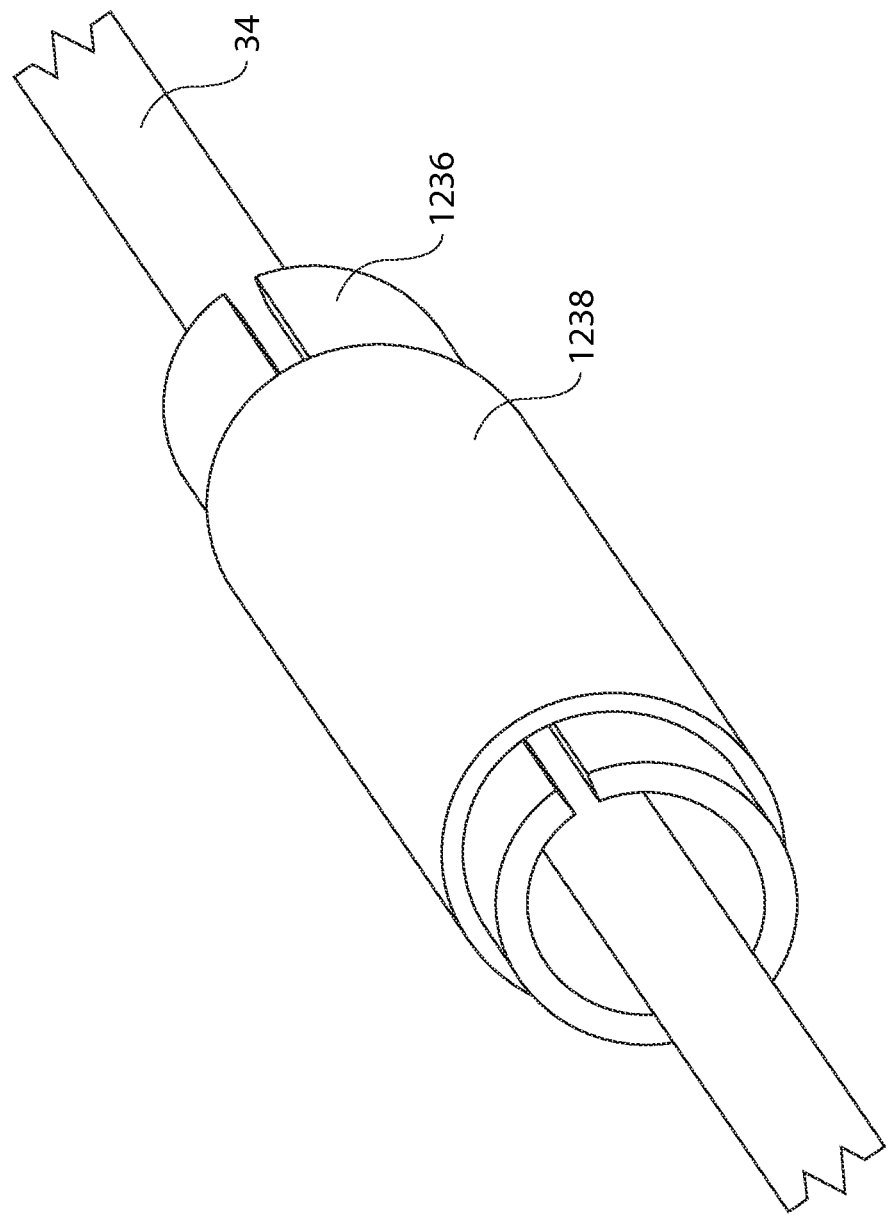

Next, the embryonic lock 1236 is rolled into the configuration seen in FIG. 39, after which a filament 34 is threaded through the resulting bore of the embryonic lock 1236 as depicted in FIG. 40. After this threading step, the embryonic lock 1236 is "armed" by bending/crimping at lest some of the pointed tabs 1237 inward, resulting in armed pointed tabs 1237A, as may be seen in FIG. 41. This arming step may be controlled to vary the resulting friction force between the resulting lock and the filament 34 as detailed above with respect to, for example, FIGS. 26A-26C. After the arming step, a cover 1238 may be placed around the rolled embryonic lock 1236 to maintain the rolled configuration of the embryonic lock 1236. This cover 1238 may be a stainless steel cylinder that creates an interference fit with the rolled embryonic lock 1236.

It is noted that the pointed tabs 1237 may instead be bent before the rolling step. Thus, the rolling step may be controlled to vary the resulting friction force between the resulting lock and the filament 34 in a manner analogous to that detailed above.

Figure 43:
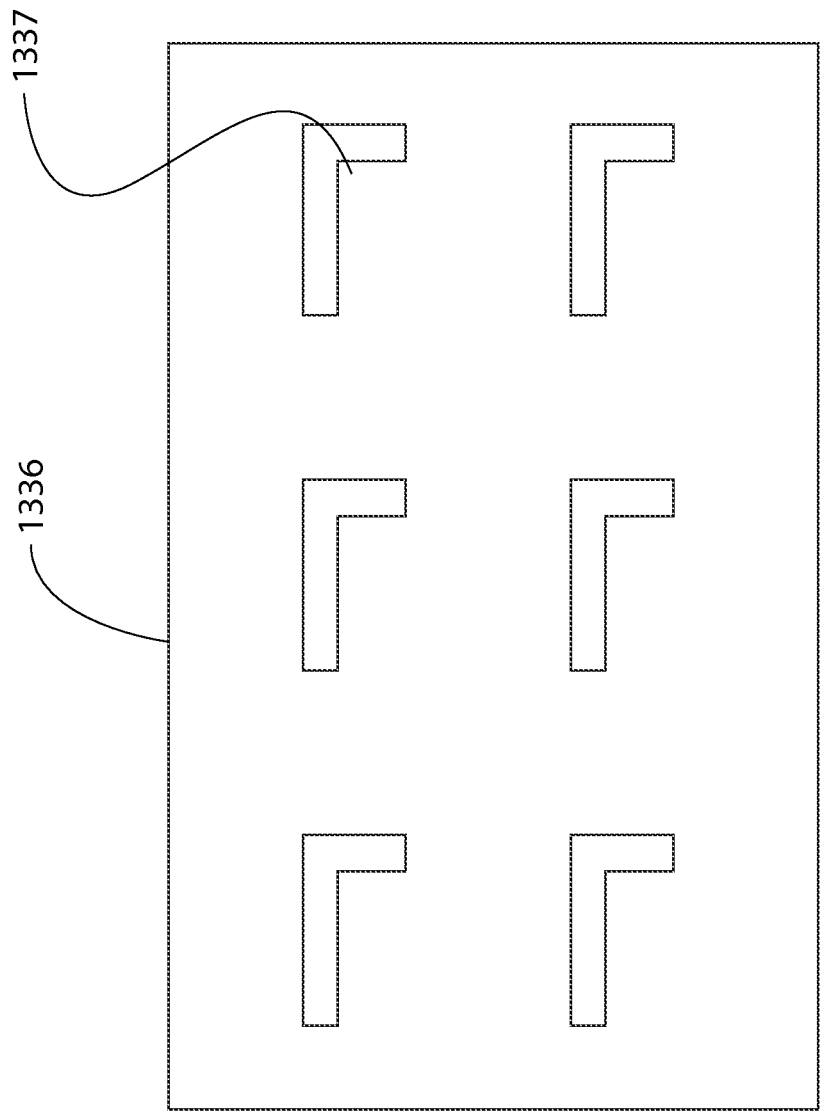
FIGS. 43-47 depict additional exemplary embodiments of embryonic locks.

FIG. 43 depicts an alternate embryonic lock 1336 that substantially parallels that of 1236 except that the pointed tabs 1337 have the configuration seen in the figure.

Figure 44:
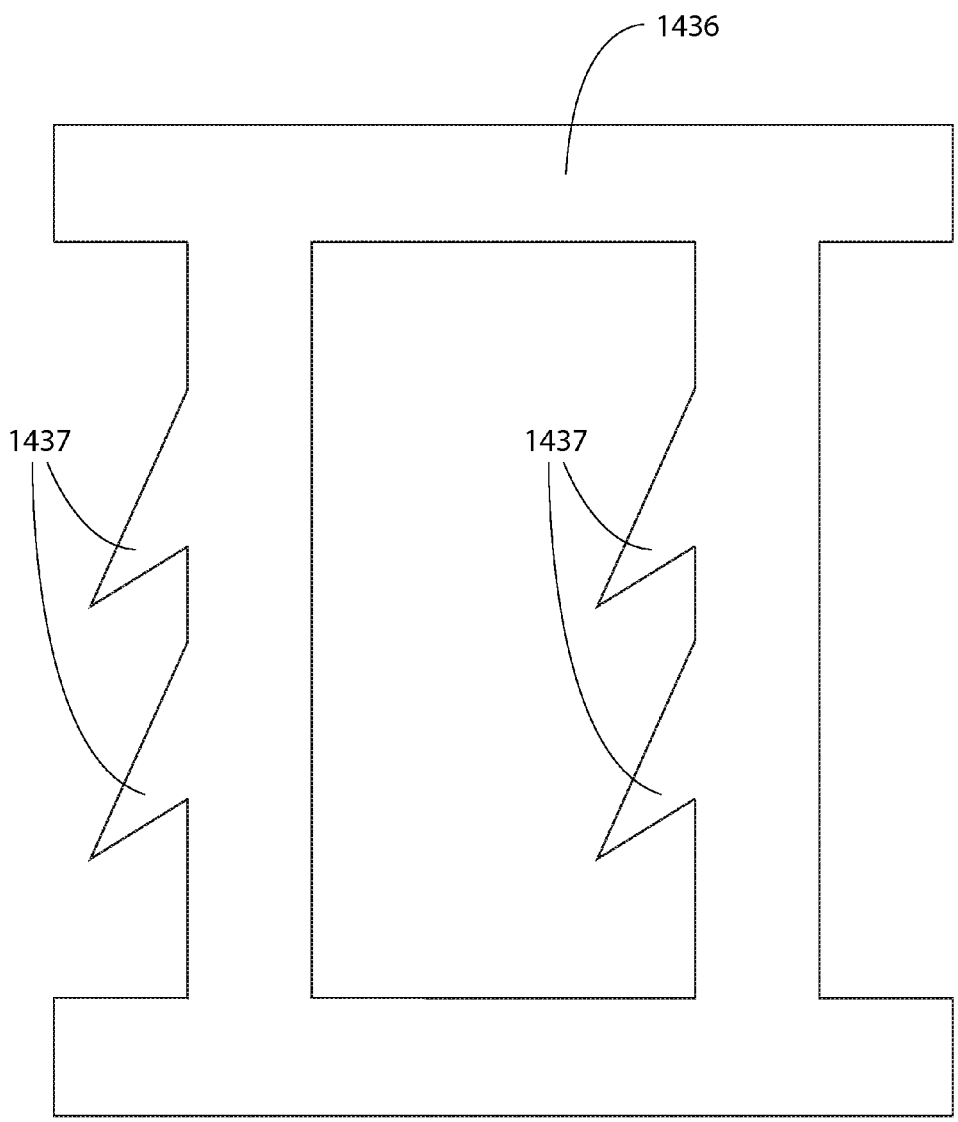

FIG. 44 depicts yet another alternate embryonic lock 1436 that may be incorporated into the closure device 20 detailed herein. As may be seen from FIG. 44, initially, the embryonic lock 1436 is in the form of a plate including one or more pointed tabs 1437 etched therein. In other embodiments, the embryonic lock 1436 may be formed with the tabs 1437 through stamping or through lithography. The embryonic lock 1436 may be incorporated into the closure device as detailed above with respect to the embryonic lock 1236.

Figure 45:
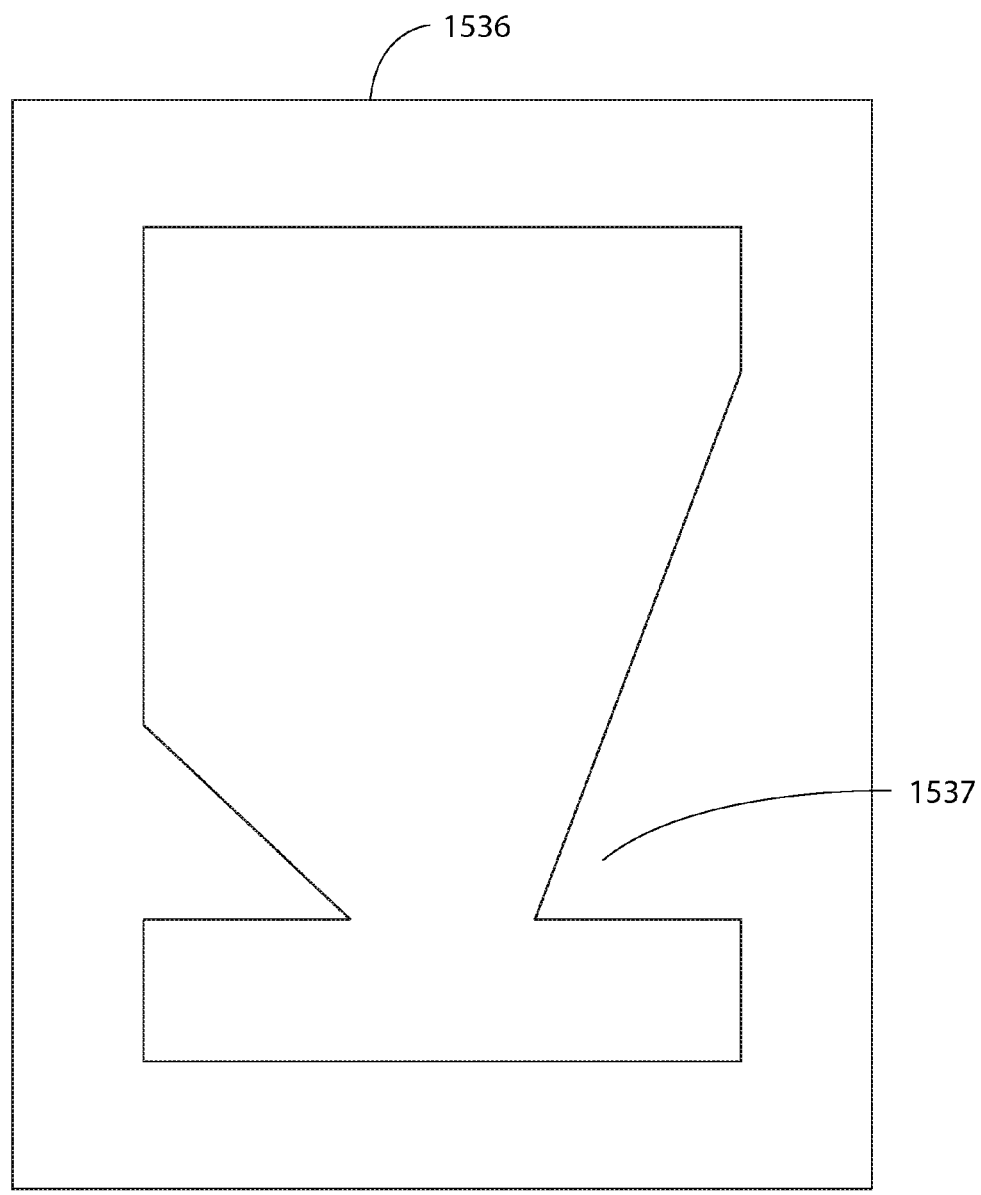

FIG. 45 depicts yet another alternate embryonic lock 1536 that may be incorporated into the closure device 20 detailed herein. As may be seen from FIG. 45, initially, the embryonic lock 1536 is in the form of a plate including one or more pointed tabs 1537 etched therein. In other embodiments, the embryonic lock 1536 may be formed with the tabs 1537 through stamping or through lithography. The embryonic lock 1536 may be incorporated into the closure device as detailed above with respect to the embryonic lock 1236.

In some embodiments, the plates of the embryonic locks presented herein with respect to FIGS. 38-45 may be 2 mm by 3 mm or 3 mm by 3 mm with a thickness of 2-5 mils. When rolled, the interior diameter (bore diameter) may be about 20-30 mils, and the outer diameter may be about 30-40 mils.

Figure 46:
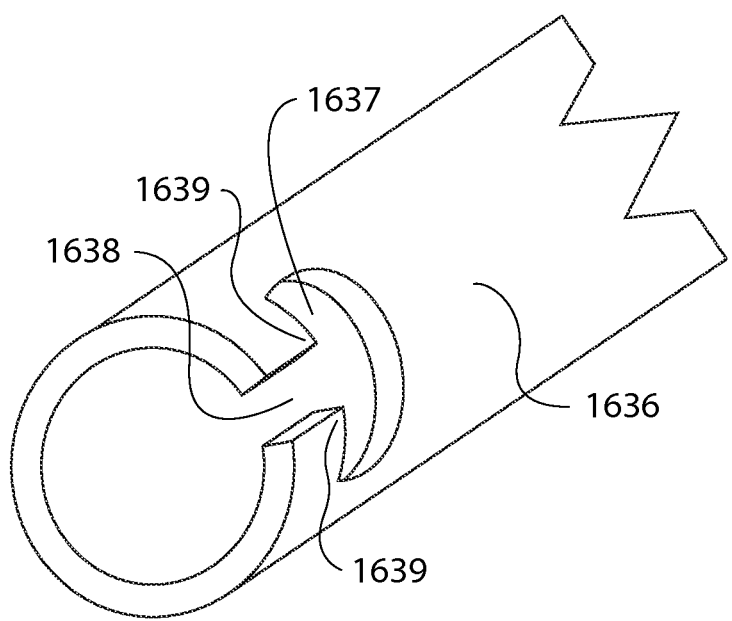
Figure 47:
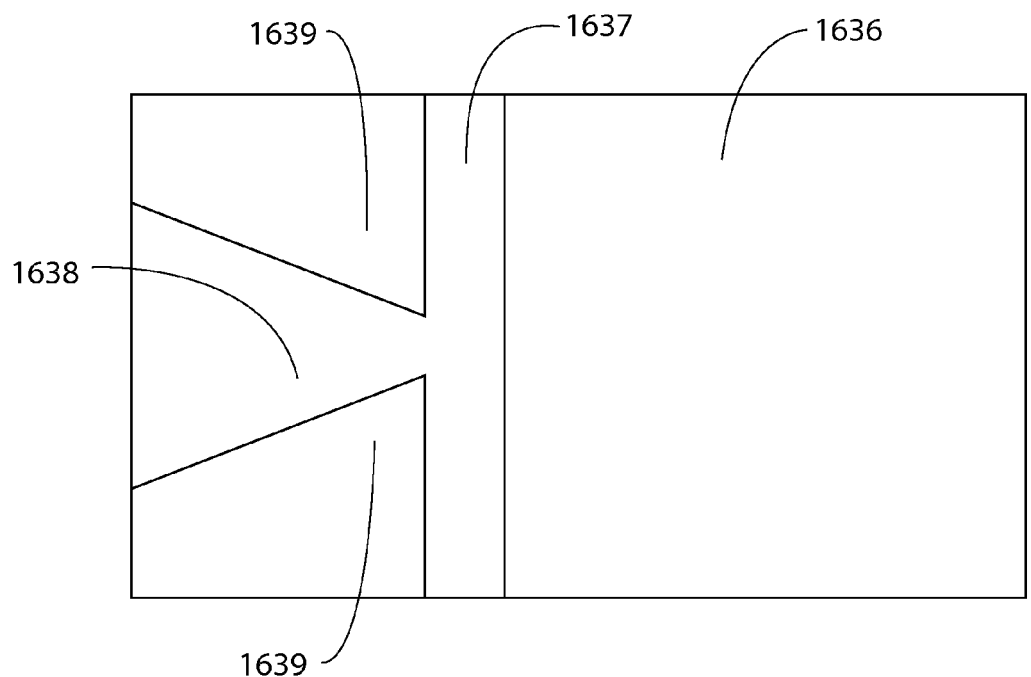
Figure 48:
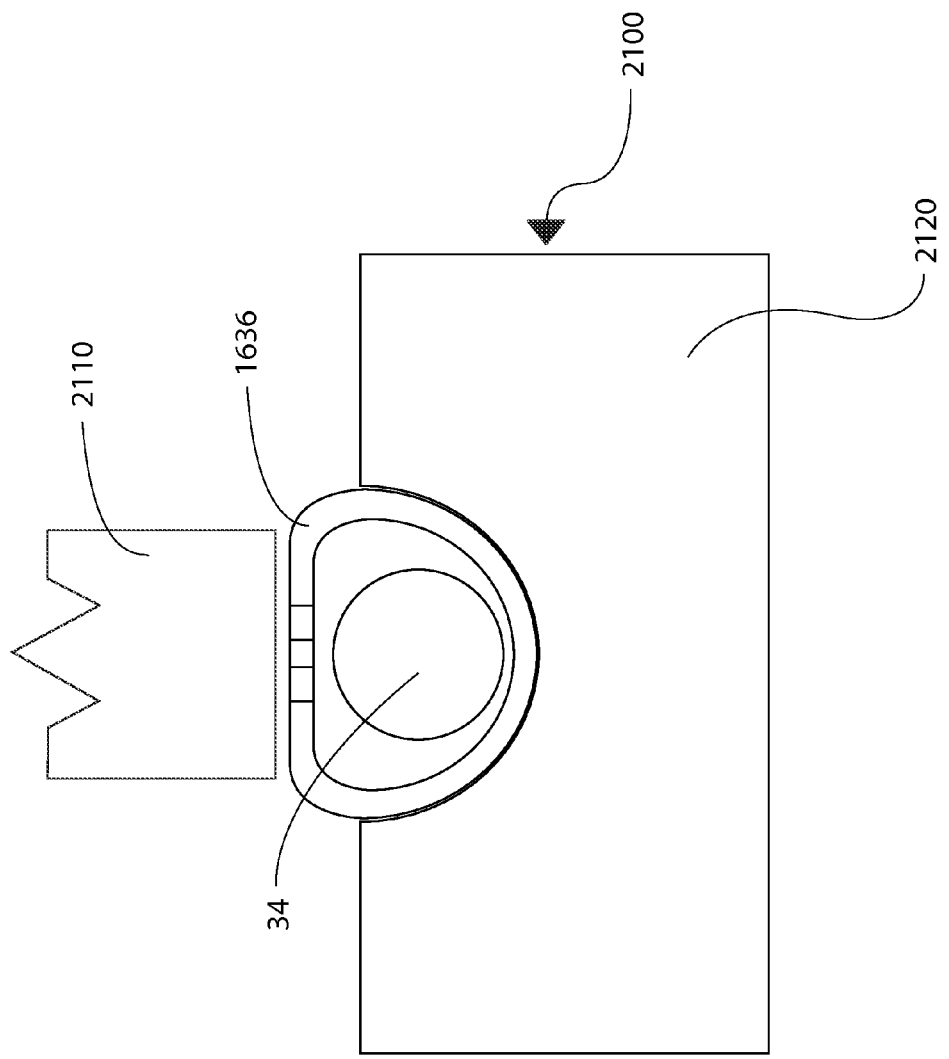
FIG. 48 depicts an exemplary embodiment in which the lock is deformed whereby the requisite friction force between the lock and the filament is controlled.
Figure 49:
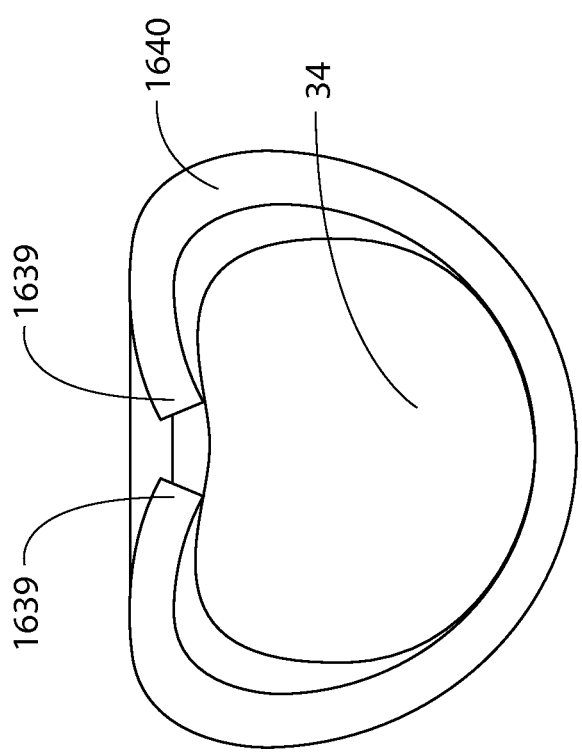

FIGs. 46 and 47 depict yet another alternate embryonic lock 1636 that may be incorporated into the closure device 20 detailed herein. As may be seen from FIGS. 46 and 47 (FIG. 47 being a top view of the embryonic lock 1636), initially, the embryonic lock 1636 has the form depicted in these figures. A slot 1637 and a slot 1638 is etched or laser cut, etc., into the embryonic lock 1636. Inner diameter (bore diameter) of the embryonic lock 1636 may be about 0.025 inches and the outer diameter of the embryonic lock 1636 may be about 0.040 inches. Next, the embryonic lock 1636 is placed into crimping fixture 2100 whereby mandrel 2110 is pressed downward onto the slots 1637 and 1638 as may be seen in FIG. 48 to bend the tabs 1639 inward towards the filament 34 as may be seen in FIG. 49. This results in the lock 1640 as may be seen in FIG. 49. As may be seen, cradle 2120 reacts against the force of mandrel 2110.

Similar to the embodiment detailed above with respect to FIG. 33, mandrel 2110 and the slots 1637 and 1638 may be dimensioned such that the slots 1637 and/or 1638 guide the mandrel 2110 during the crimping operation.

It is noted that in some embodiments, the tabs 1639 may be pre-bent inward before crimping. It is further noted that the wall thickness of the embryonic lock 1636 may be varied and/or the dimensions of the slots 1637 and 1638 (including angles seen in the FIGs.), and thus the resulting tabs 1639 may be varied as appropriate.

Figure 50:
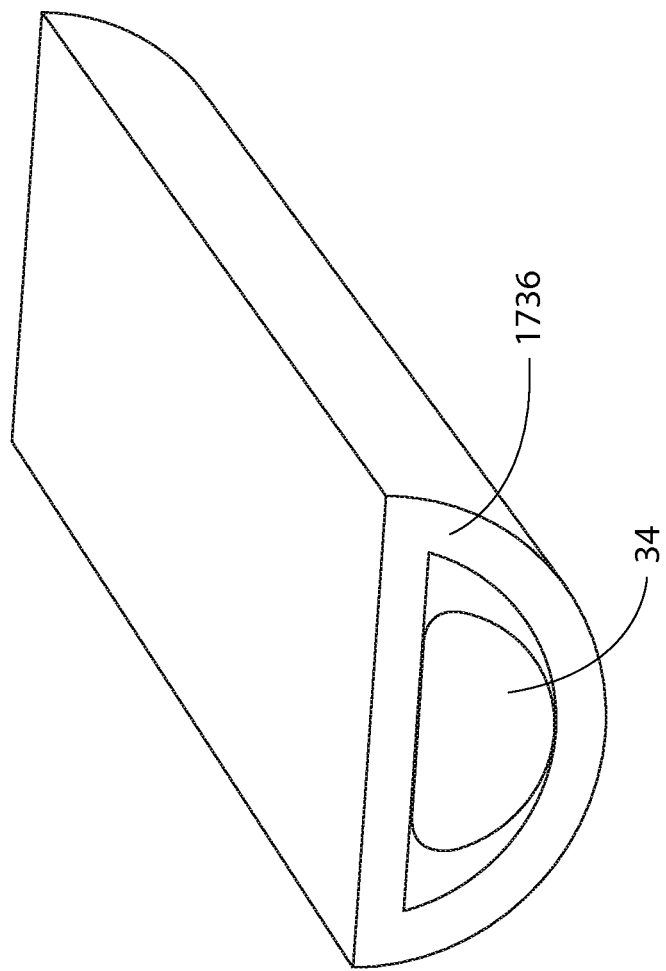
Figure 51:
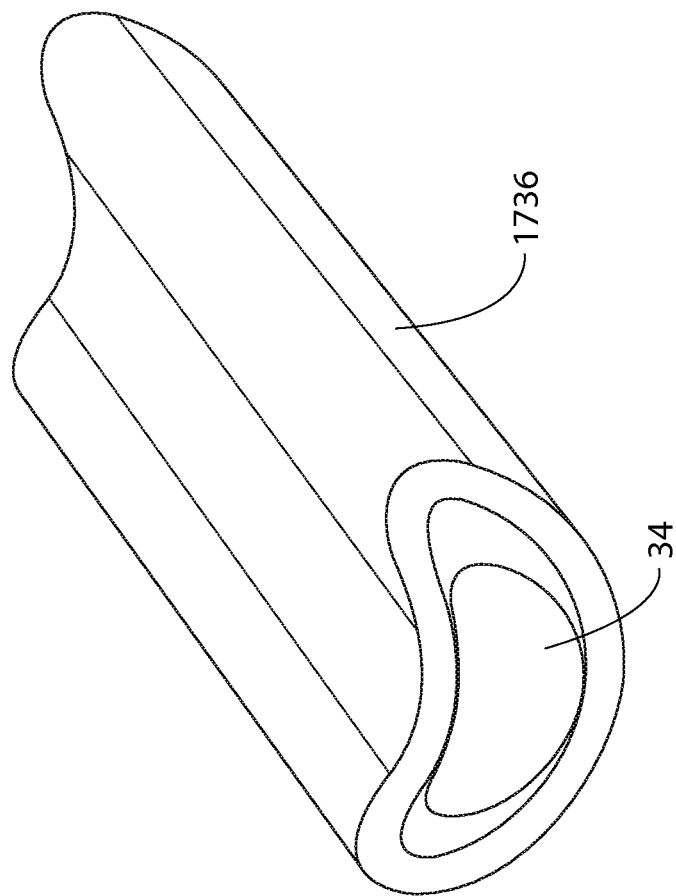

In yet another embodiment, the entire embryonic lock is crimped, as may be seen in FIGS. 50 and 51, where element 1736 is a crimped lock.

FIG. 52 depicts an alternate embodiment of a lock. Specifically, as may be seen, there is a lock 1836 in the form of a flexible elongated thin plate with various holes therethrough.

Figure 55:
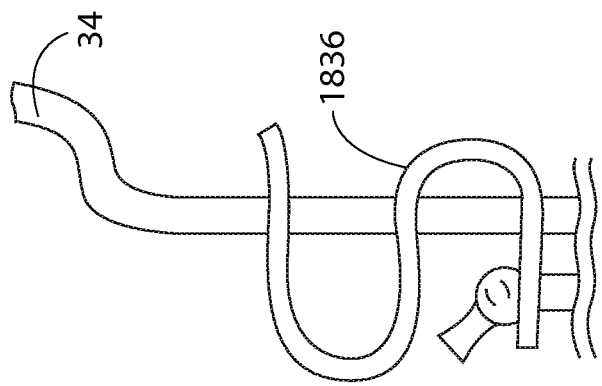
Figure 54:
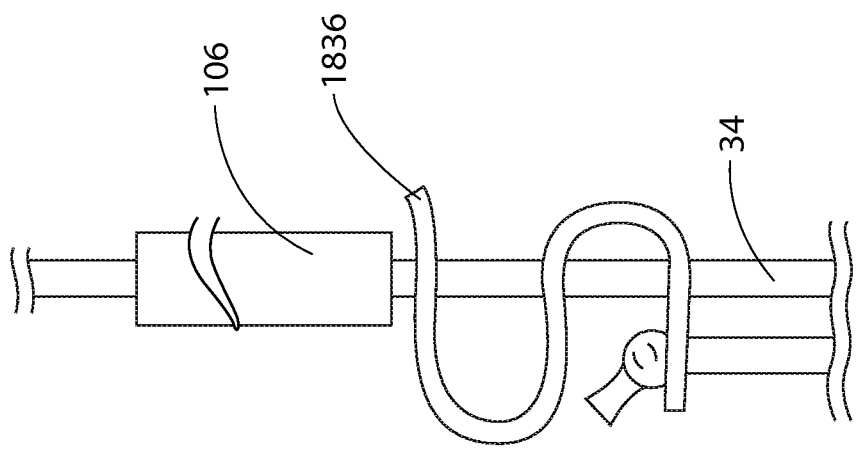

Filament 34 is woven through the holes of the lock 1836 as may be seen in FIG. 53, with sections 34B and 34C and 34D corresponding to sections 34B and 34C and 34D detailed above. As may be seen in FIG. 53, tensioning the filament 34 results in the lock 1836 deforming from its original flat position. Tamper 106 is used in conjunction with a tension force applied to the filament 34 as may be seen in FIG. 54 to further deform the lock 1836 to the configuration seen in FIG. 55. As may be seen, lock 1836 includes hole 1837 that has a section that is wider than another section, to holes 536C and 536D depicted in lock 536 above in FIGS. 14A-14C. Specifically, a portion of the hole 1836 is narrower than the natural outer diameter of filament 34, and thus provides a limited resistance to movement of filament 34 through the slot. The filament 34 locks into the lock 1836 in the same way that the filament 34 locks into the lock 536 detailed above. In an embodiment, hole 1837 becomes gradually narrower, thus locking the filament 34 in place. In another embodiment, hole 1837 has a relatively constant width.

Figure 56:
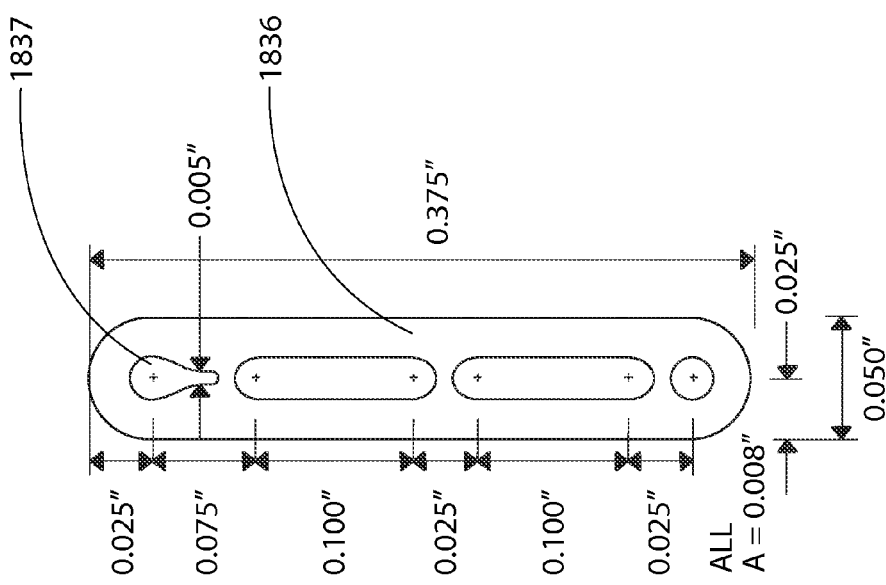
FIG. 56-58 depict additional exemplary embodiments of locks.

FIG. 56 depicts exemplary dimensions of the lock 1836. In an exemplary embodiment, the lock 1836 is 0.002, 0.003, 0.004 or 0.005 inches thick. The hole 1837 tapers to have a width of about 0.005 inches at its base. In an exemplary embodiment, the holes depicted in FIG. 56 are 0.016 inches wide, while in other embodiments, the holes are about 0.025 inches wide (i.e., the bottom hole has a radius of 0.0125 inches). In an exemplary embodiment, the lock 1836 is pre-bent into a slight "S" shape as may be seen in FIG. 53. This helps ensure that the ultimate bent shape of the lock 1836 takes the form as depicted in the figures and permits easier threading of the filament 34 through the holes. It is further noted that in some embodiments, one or more of the elongated holes depicted in FIG. 56 are shorter by about 0.040 inches than that depicted in FIG. 56.

In an exemplary embodiment, the hole 1837 may also be one-sided shuch that the interior of the hole 1836 favors locking in one direction of filament 34 movement and sliding in the other direction of filament 34 movement. This may, in some embodiments, prevent dragging of the hole 1836 with the filament 34 as the hole 1837 is bent as the lock 1836 is bent.

Figure 57:
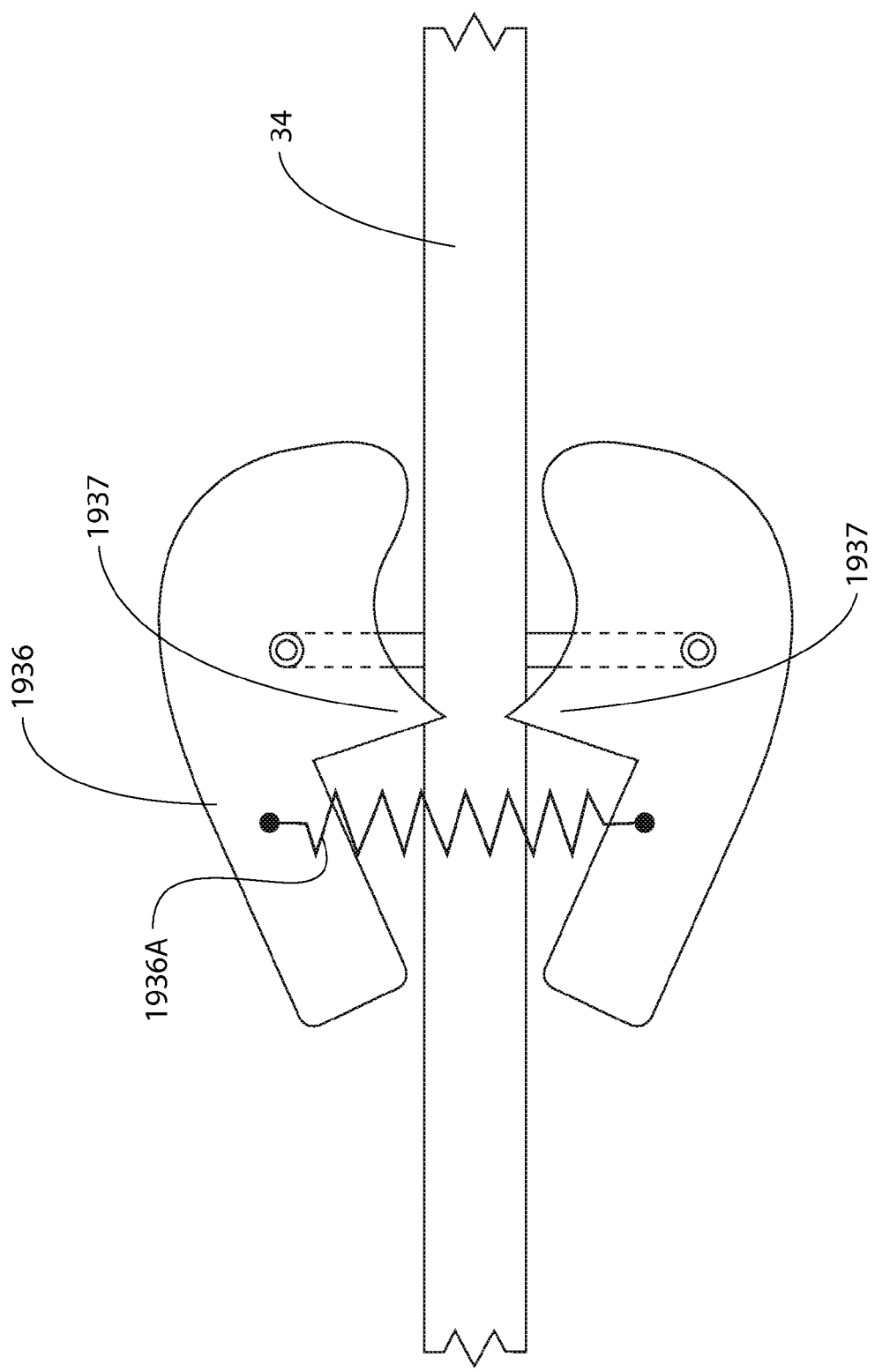
Figure 58:
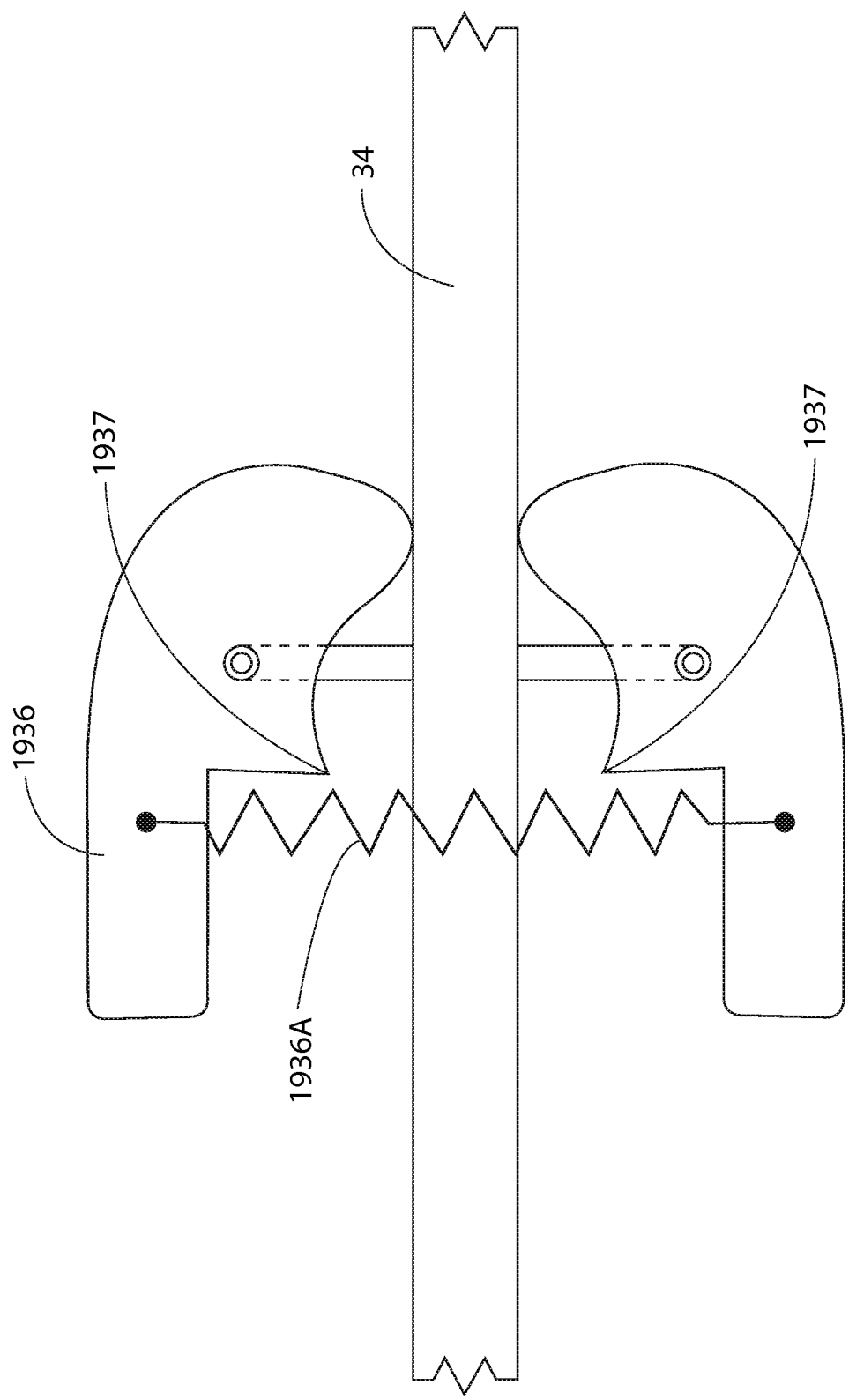
Figure 59:
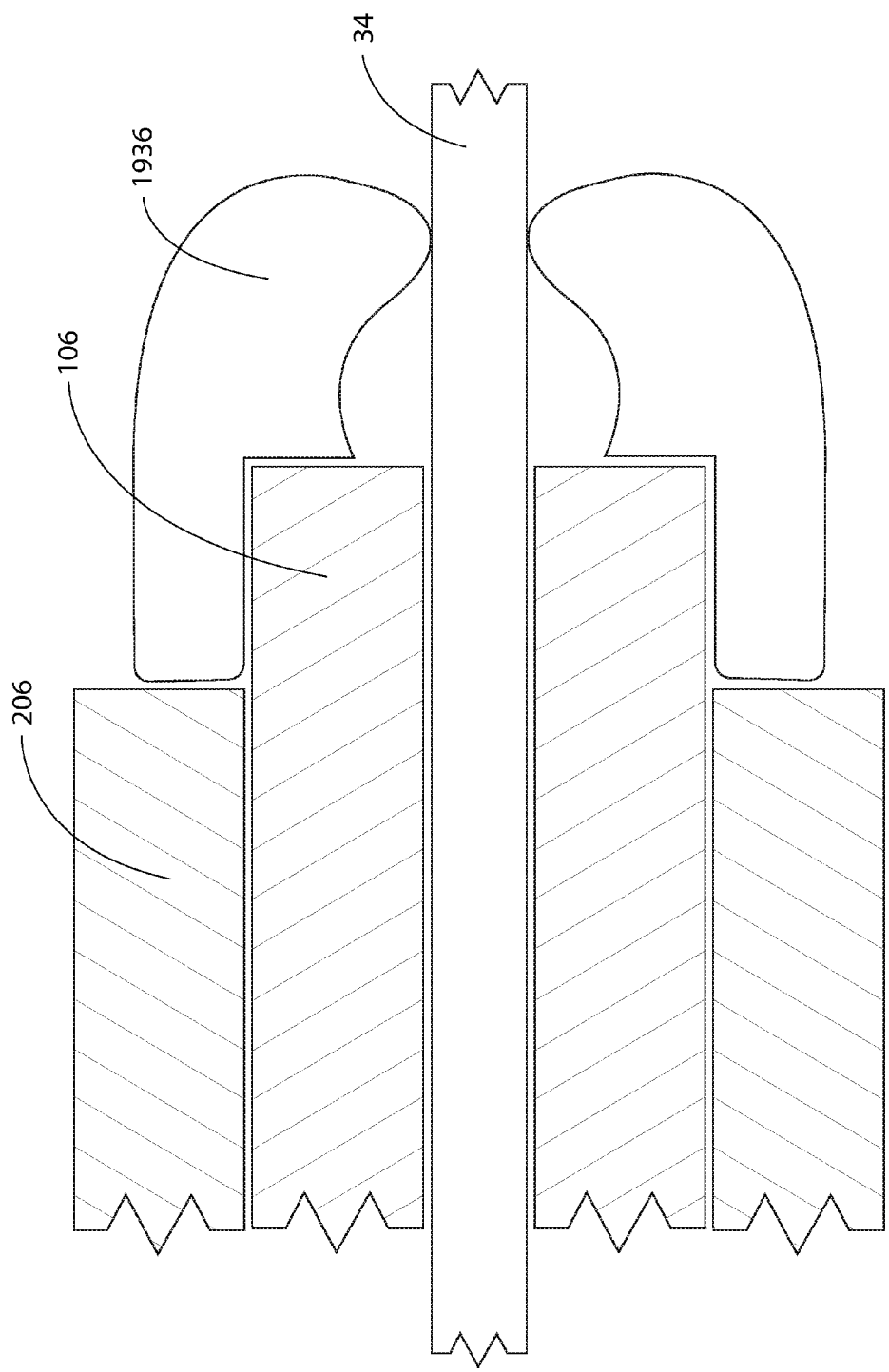
FIG. 59 depicts tampers used to position the lock of FIG. 58.

FIGS. 57 and 58 depict an alternate embodiment of a lock 1936 that clips onto the filament 34 upon release from tamper 106. Specifically, lock 1936 is configured to be biased to conform to the configuration depicted in FIG. 57 vis-à-vis the filament 34 from that depicted in FIG. 58. In an exemplary embodiment, the lock 1936 is spring-loaded by springs 1936A so that it springs to the configuration depicted in FIG. 57, whereby nips 1937 compress the filament 34, thereby increasing the friction force between the lock 1936 and the filament 34 required to be overcome to move the lock 1936 (relative to the friction force, if any, resulting from the configuration depicted in FIG. 58, where the filament easily slides through the lock 1936). In an exemplary embodiment of deploying the lock 1936, the lock 1936 is initially positioned on a tamper 106 as depicted in FIG. 59. As can be seen, tamper 106 holds the lock 1936 in the position depicted in FIG. 58, where little if any friction force must be overcome between the lock 1936 and the filament 34 to move the lock 1936 relative to filament 34. After the lock 1936 is positioned as desired by driving the tamper 106 towards the anchor 32 (i.e., to the right with respect to FIG. 59), the tamper 106 is withdrawn in the opposite direction. The little friction force between the lock 1936 and the filament 34 is sufficient to drag the lock 1936 from the tamper 106, thereby ejecting the lock 1936 from the tamper 106. Alternatively or in addition to this, a second tamper 206 is pushed along the first tamper 106 to drive the lock 1936 from the tamper 106, as depicted in FIG. 59, while applying a tension to filament 34 in the opposite direction of which the second tamper 206 is moved. After the lock 1936 is ejected from the tamper 106 (either through use of tamper 206 or via the little friction that exists between the lock 1936 and the filament before the lock 1936 takes the configuration depicted in FIG. 57), the lock springs to the configuration depicted in FIG. 57, thereby increasing the friction force that must be overcome between the filament 34 and the lock 1936 to move the lock 1936 relative to the filament 34. The tamper may then be advanced again towards the anchor 32 using the tamper 106 to push the lock 1936 along the filament 34 while applying tension to the filament 34 in the opposite direction in a manner analogous to the deployment of the other locks detailed herein.

Figure 60:
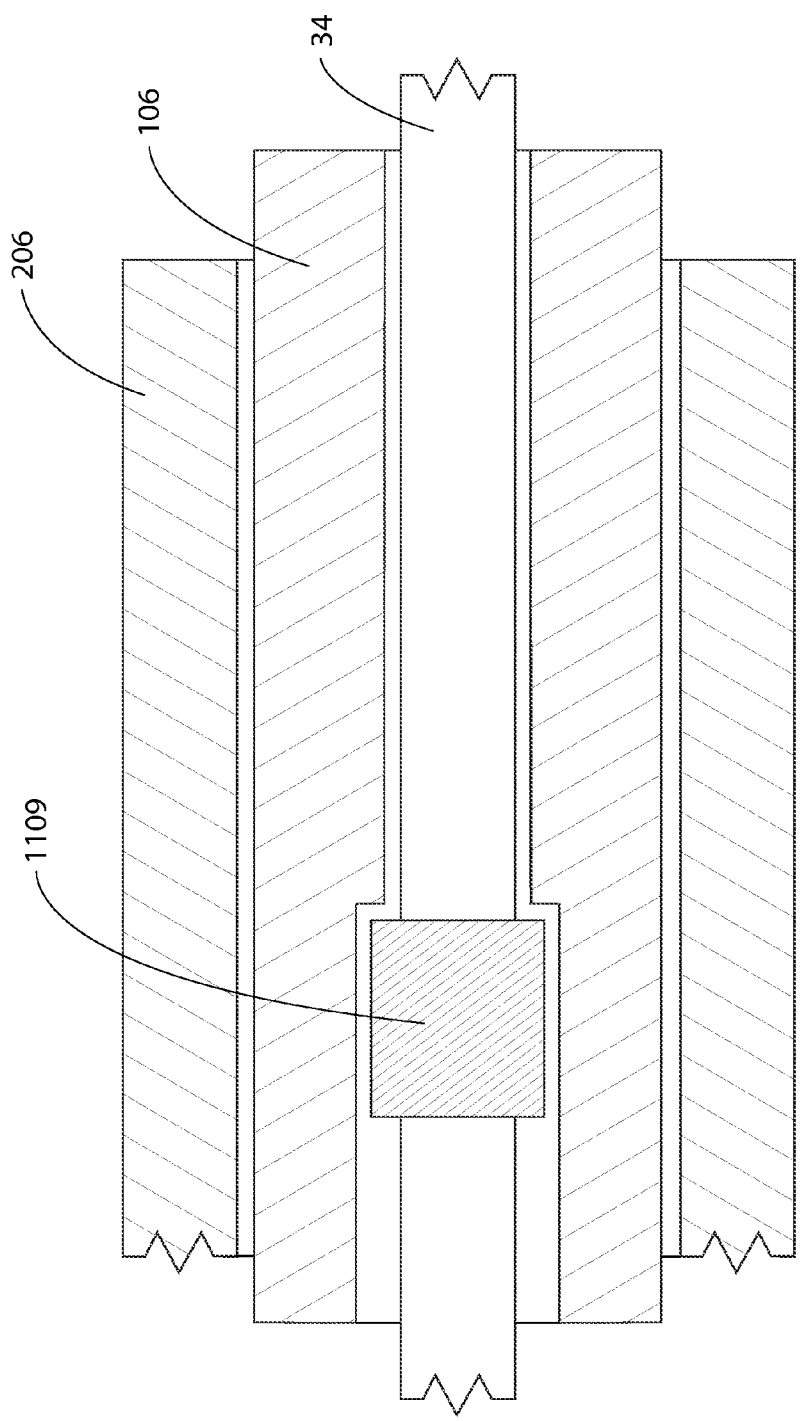
FIG. 60 depicts a portion of one of the tampers of FIG. 59.

In an exemplary embodiment utilizing the dual tampers 106 and 206, a crimp 1109 (or, in an alternative embodiment, a knot) is provided in filament 34 as depicted in FIG. 60 to prevent the tamper 106 from sliding as the tamper 206 is moved relative to the tamper 106 in the event that friction forces develop between the two tampers.

In yet an alternative exemplary embodiment, the lock 1936 is not spring loaded to conform from one configuration to another configuration. Instead, the lock 1936 is a static lock with a nip at the interface of the lock 1936 and the filament 34 that results in a friction force that must be overcome to move the lock 1936 relative to the filament 34 analogous to the friction forces that must be overcome with respect to other embodiments of locks as disclosed herein. Thus, in some embodiments, the lock 1936 functions and is positioned in an analogous manner to the locks detailed above.

While various embodiments of the present invention have been described above, it should be understood that they have been presented by way of example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with any future claims and their equivalents.

What is claimed is:

1. A closure device for sealing a percutaneous puncture in a wall of a body passageway, the closure device comprising:
an anchor configured to engage an interior surface of the body passageway;
an expandable plug;
a contiguous elongate filament, comprising a longitudinal axis, coupled to the anchor and the plug, including first and second sections and a collar, the first and second sections extending from the anchor with the first section extending through the collar connected to the second section such that a loop is formed by the first and second sections and the collar, wherein the loop extends through an orifice in the plug; and
a lock frictionally engaged to a portion of the first section extending beyond said loop, wherein the collar is located proximal to the plug and distal to the lock between a proximal end of the plug and a distal end of the lock, and wherein the filament extends through an orifice in the lock and the lock is movable along the filament, in either direction along the longitudinal axis of the filament, in response to application of a force on the lock that overcomes the frictional engagement, whereby as the lock is moved along the first section towards the anchor, the loop shrinks causing the plug to move toward the anchor, wherein the lock is configured to prevent the loop from expanding after said shrinkage of the loop.

2. The closure device of claim 1, wherein the loop is configured to shrink upon the application of a force on the first extending section in a direction away from the anchor that causes the collar to move relative to the first extending section towards the anchor.

3. The closure device of claim 1, wherein the lock comprises a resorbable material.

4. The closure device of claim 1, wherein the lock comprises iron.

5. The closure device of claim 1, wherein the lock includes a cylindrical hole extending through the lock, wherein the first section extends through the cylindrical hole, wherein a protrusion extends into the cylindrical hole, thereby forming an interference with the first extending section that results in the frictional engagement.

6. The closure device of claim 5, wherein the lock is crimped about the first section, wherein the crimp forms the interference with the first extending section.

7. The closure device of claim 1, wherein a force of about ¼ to ½ pounds applied to the lock is required to overcome the frictional engagement.

8. The closure device of claim 1, wherein a force of about ½ pounds to about 1 pound applied to the lock is required to overcome the frictional engagement.

9. The closure device of claim 1, wherein a force of about 1 pound applied to the lock is required to overcome the frictional engagement.

10. The closure device of claim 1, wherein the lock comprises a non-resorbable material.

11. The closure device of claim 1, wherein the lock comprises stainless steel and/or titanium.

12. The closure device of claim 1, wherein:
the lock includes a radio-opaque material and/or is connected to a radio-opaque material; and
the anchor includes a radio-opaque material and/or is connected to a radio-opaque material.

13. A method of sealing a percutaneous puncture in a body passageway of a living being, the method comprising:
providing a closure device for sealing a percutaneous puncture in a wall of a body passageway, the closure device comprising: an anchor configured to engage an interior surface of the body passageway; an expandable plug; a contiguous elongate filament, comprising a longitudinal axis, coupled to the anchor and the plug, including first and second sections and a collar, the first and second section extending from the anchor with the first section extending through the collar connected to the second section such that a loop is formed by the first and second sections and the collar, wherein the loop extends through an orifice in the plug; and a lock frictionally engaged to a portion of the first section extending beyond said loop, wherein the collar is located proximal to the plug and distal to the lock between a proximal end of the plug and a distal end of the lock, and wherein the filament extends through an orifice in the lock and the lock is movable along the filament, in either direction along the longitudinal axis of the filament, in response to application of a force on the lock that overcomes the frictional engagement, whereby as the lock is moved along the first section towards the anchor, the loop shrinks causing the plug to move toward the anchor, wherein the lock is configured to prevent the loop from expanding after said shrinkage of the loop; inserting the anchor coupled to a loop in the body passageway through the percutaneous puncture;
bringing the anchor into engagement with an interior wall of the body passageway;
applying a tension force to a portion of the filament so that a force is applied to the loop tending to decrease a circumference of the loop,
applying a tamping force to the lock in a direction towards the loop and in a direction away from the direction of the applied tension to the portion of the filament, wherein the tamping force is sufficient to overcome the frictional engagement forces so that the lock slides along the filament in a direction towards the anchor, wherein
the lock is configured to resist movement along the filament in a direction opposite the direction of the tamping force, thereby preventing the circumference of the loop from expanding relative to the circumference of the loop after application of the tamping force and the tension force.

14. The method of claim 13,
the method further comprising:
moving a proximal portion of the plug toward the anchor as a result of reducing the circumference of the loop.

15. The method of claim 13, wherein:
the tamping force applied to the lock is about ¼ to ½ pounds.

16. The method of claim 13, wherein:
the tamping force applied to the lock is about ½ pounds.

17. The method of claim 13, further comprising:
after applying the tamping force to the lock, obtaining a radiological image of the implanted anchor and the lock; and
analyzing the radiological image to evaluate a quality of the seal of the percutaneous puncture based on the relative position of the implanted anchor and the lock as depicted in the radiological image.

* * * * *